United States Patent
Stucky et al.

(10) Patent No.: US 7,176,245 B2
(45) Date of Patent: *Feb. 13, 2007

(54) BLOCK COPOLYMER PROCESSING FOR MESOSTRUCTURED INORGANIC OXIDE MATERIALS

(75) Inventors: Galen D. Stucky, Goleta, CA (US); Bradley F. Chmelka, Goleta, CA (US); Dongyuan Zhao, Shanghai (CN); Nick Melosh, Tucson, AZ (US); Qisheng Huo, Williamsville, NY (US); Jianglin Feng, Charlottesville, VA (US); Peidong Yang, Santa Barbara, CA (US); David Pine, Santa Barbara, CA (US); David Margolese, Montecito, CA (US); Wayne Lukens, Jr., Summerland, CA (US); Glenn H. Fredrickson, Santa Barbara, CA (US); Patrick Schmidt-Winkel, Bad Gams (AT)

(73) Assignee: The Regents of the University of California, Oakland, CA (US)

( * ) Notice: Subject to any disclaimer, the term of this patent is extended or adjusted under 35 U.S.C. 154(b) by 239 days.

This patent is subject to a terminal disclaimer.

(21) Appl. No.: 10/426,441

(22) Filed: Apr. 30, 2003

(65) Prior Publication Data

US 2003/0205528 A1    Nov. 6, 2003

Related U.S. Application Data

(63) Continuation of application No. 09/554,259, filed as application No. PCT/US98/26201 on Dec. 9, 1998, now Pat. No. 6,592,764.

(60) Provisional application No. 60/069,143, filed on Dec. 9, 1997, provisional application No. 60/097,012, filed on Aug. 18, 1998.

(51) Int. Cl.
*B01J 13/18* (2006.01)
*C01B 33/152* (2006.01)
*C01B 33/155* (2006.01)

(52) U.S. Cl. ............... 516/111; 210/660; 177/924; 428/402; 501/12; 523/209

(58) Field of Classification Search ............... 117/924; 210/660

See application file for complete search history.

(56) References Cited

U.S. PATENT DOCUMENTS

| | | | | |
|---|---|---|---|---|
| 5,770,275 A | * | 6/1998 | Raman et al. | 427/535 |
| 5,871,646 A | * | 2/1999 | Jones et al. | 210/500.21 |
| 6,503,382 B1 | * | 1/2003 | Bartlett et al. | 205/67 |
| 6,592,764 B1 | * | 7/2003 | Stucky et al. | 210/660 |
| 6,592,991 B1 | * | 7/2003 | Wiesner et al. | 428/404 |

FOREIGN PATENT DOCUMENTS

| | | | |
|---|---|---|---|
| GB | 2267486 A | * | 12/1993 |
| GB | 9713580 | * | 3/1997 |

OTHER PUBLICATIONS

Family List for US Patent 6,503,382 printed Feb. 9, 2006 from European Patent Office website at http://v3.espacenet.com/family?DB=EPODOC&IDX=US6503382&F=8&OREQ=0&textdoc=TRUE.*

* cited by examiner

*Primary Examiner*—Robert E. L. Sellers
*Assistant Examiner*—Timothy J. Kugel
(74) *Attorney, Agent, or Firm*—Berliner & Associates

(57) ABSTRACT

Mesoscopically ordered, hydrothermally stable metal oxide-block copolymer composite or mesoporous materials are described herein that are formed by using amphiphilic block polymers which act as structure directing agents for the metal oxide in a self-assembling system.

4 Claims, 62 Drawing Sheets

SUB-NANOPOROUS ZEOLITES : < 1nm
FAUJASITE 0.75 nm

MESOPOROUS MOLECULAR SIEVES: 2–10 nm

MCM-41      8 nm

ULTRA LARGE PORE MATERIALS 5 – 50 nm

SBA-15    20 nm

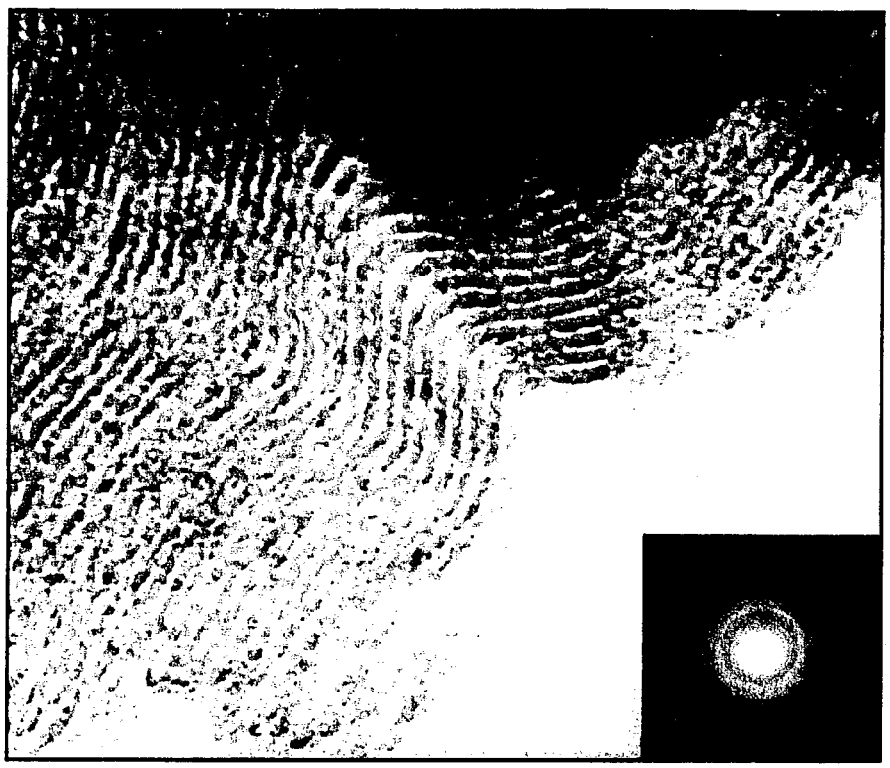
FIG. 17a   20 nm
FIG. 17b   20 nm

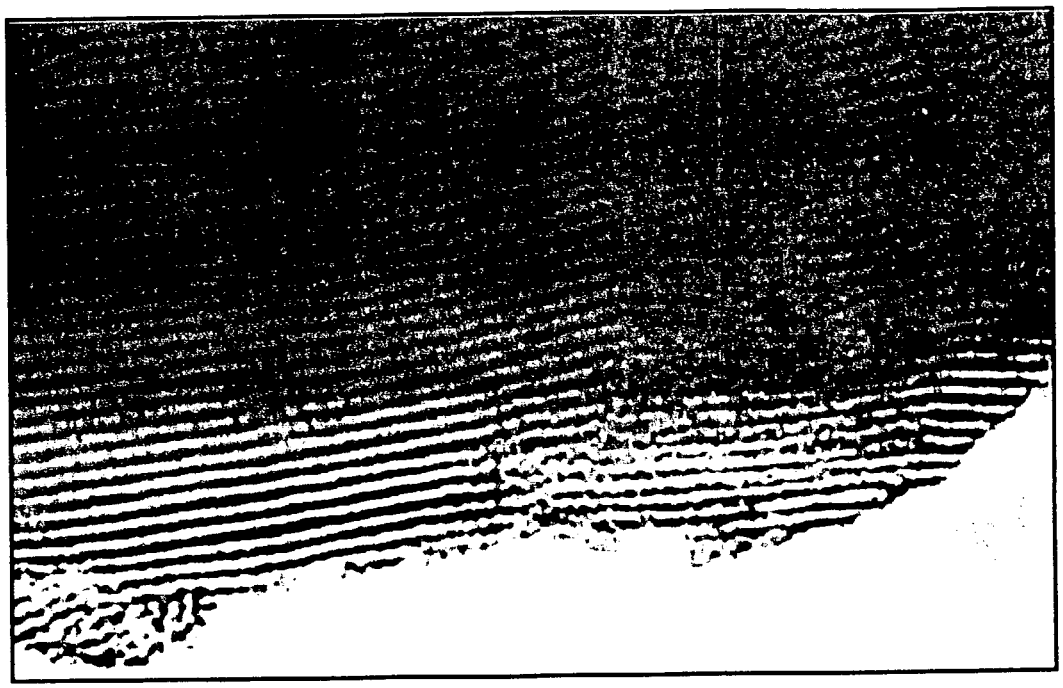
FIG. 19a   100 nm
FIG. 19b   50 nm

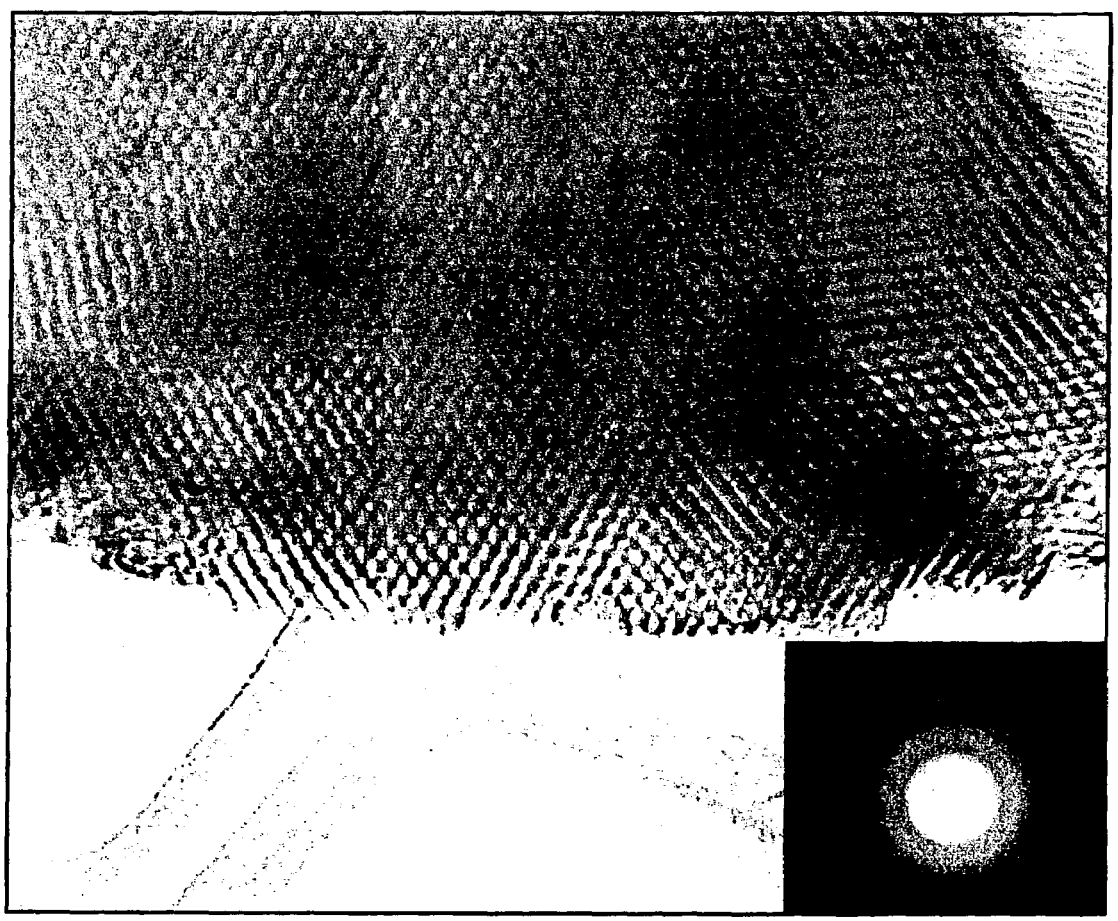
FIG. 20    20 nm

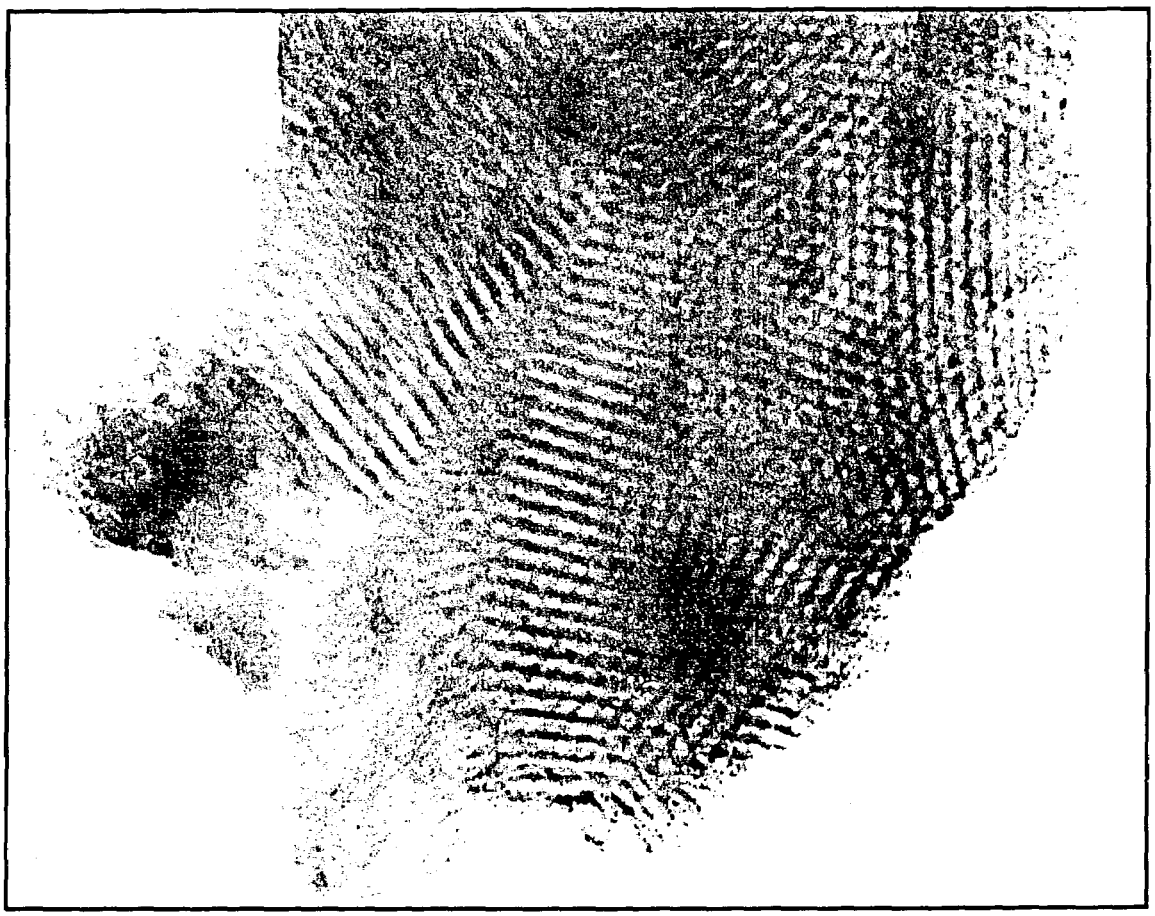

50 nm

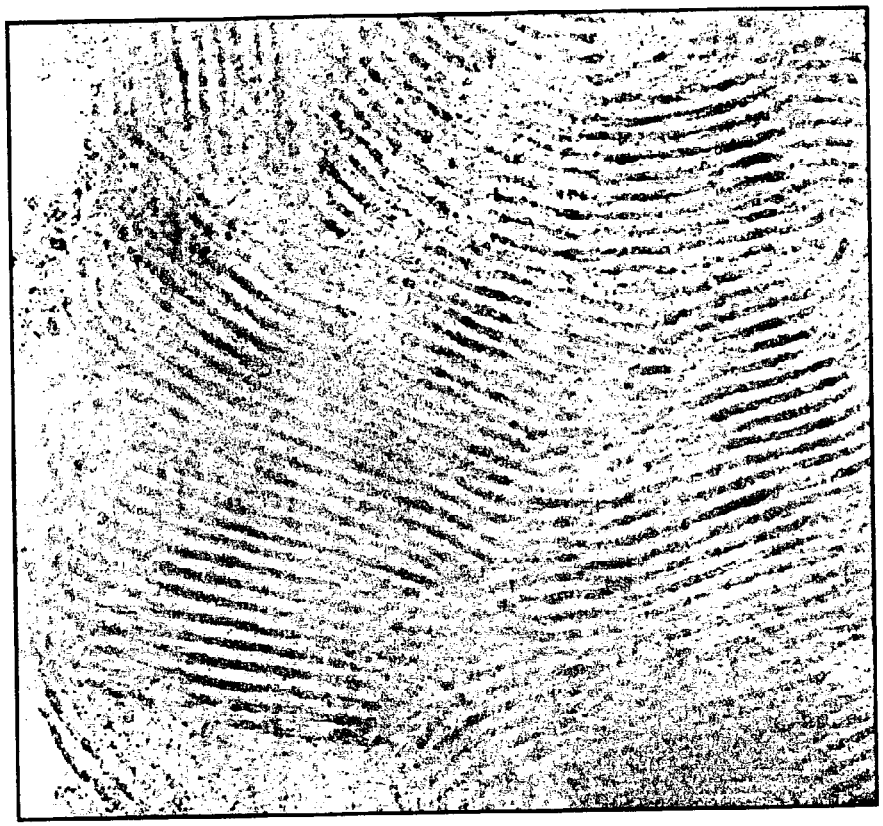
FIG. 22a   100 nm
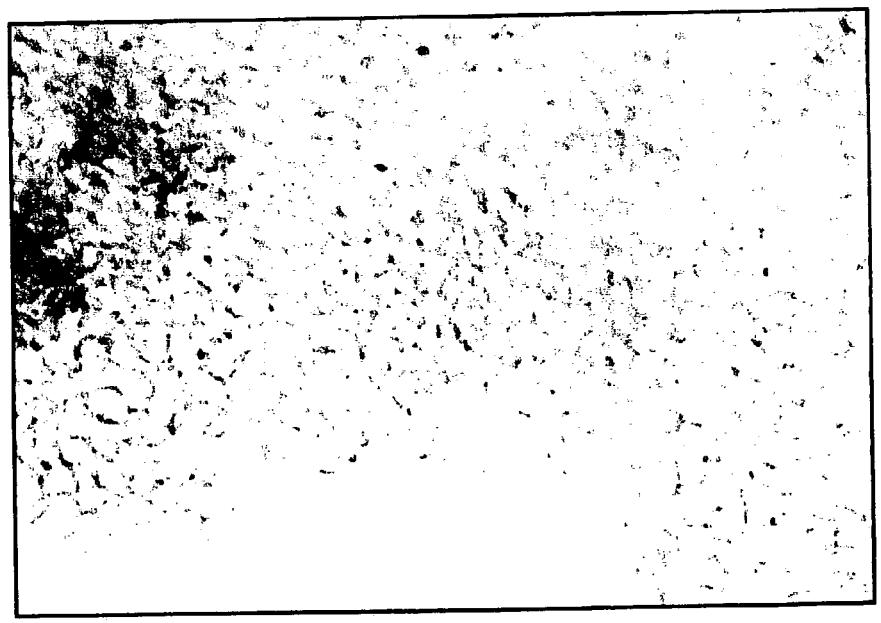
FIG. 22b   50 nm

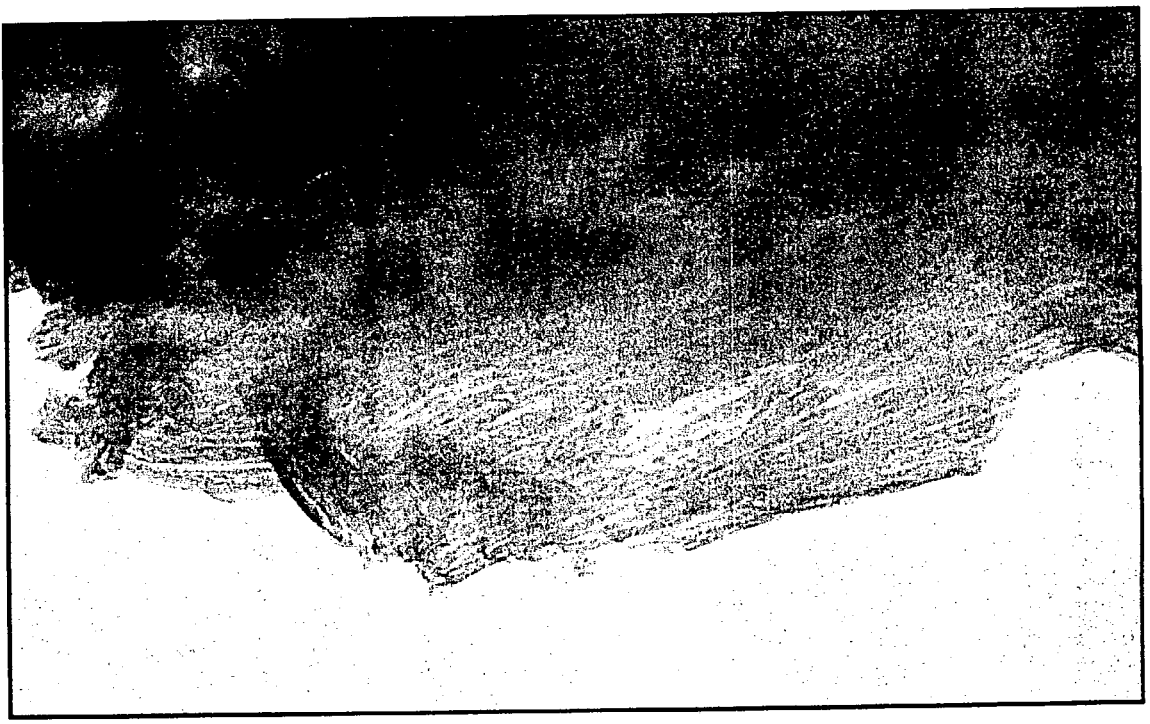
FIG. 23  50 nm

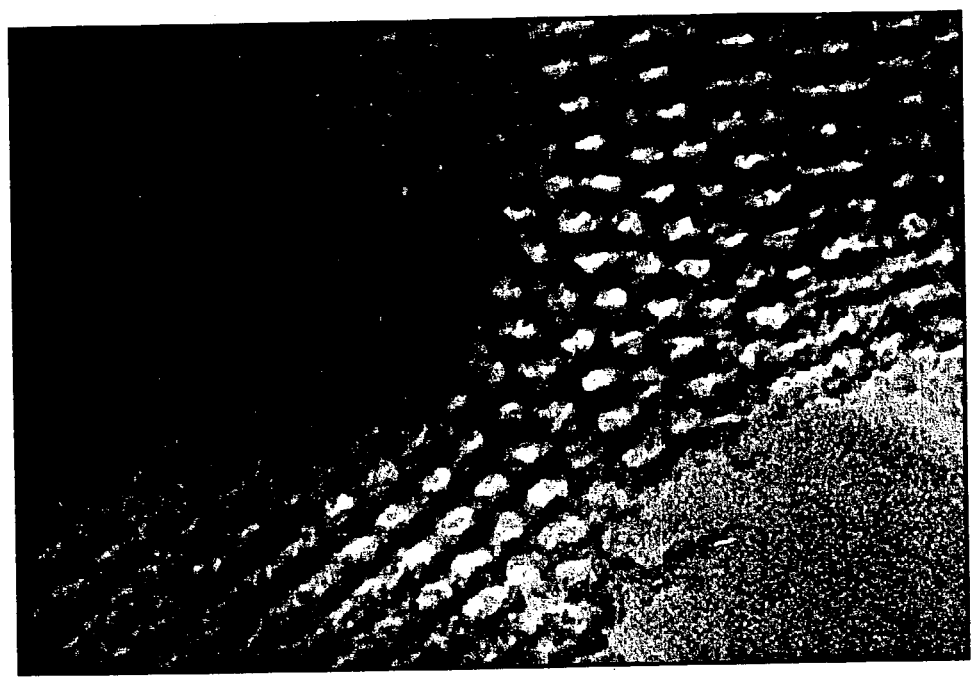
FIG. 24a  20 nm
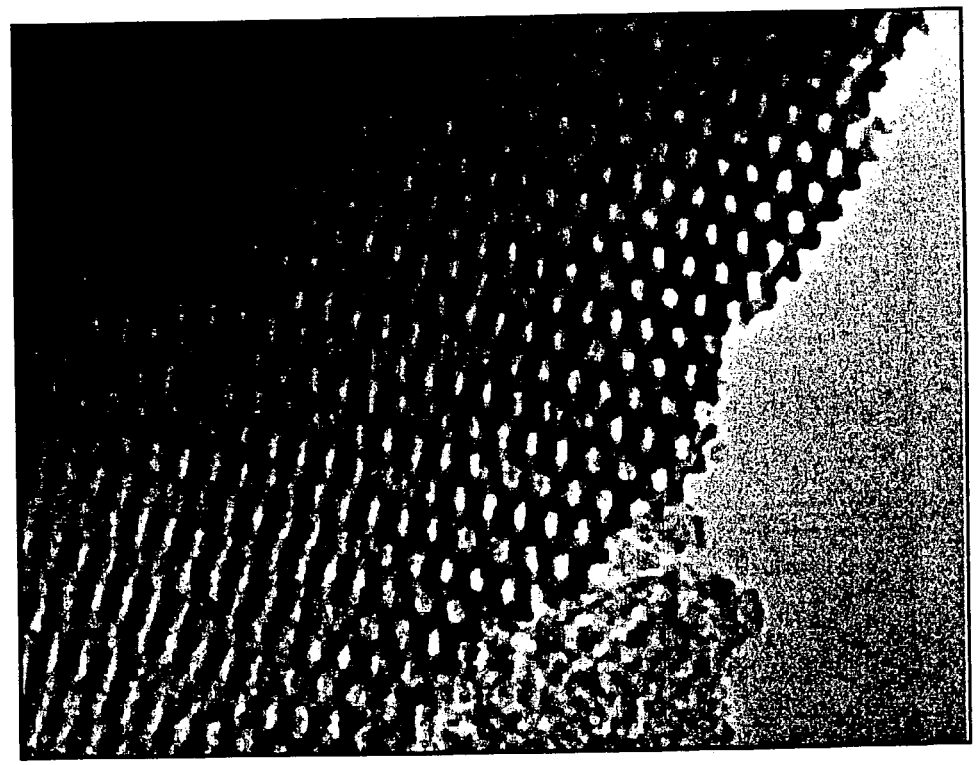
FIG. 24b  50 nm

FIG. 25a  50 nm
FIG. 25b  50 nm 20 nm

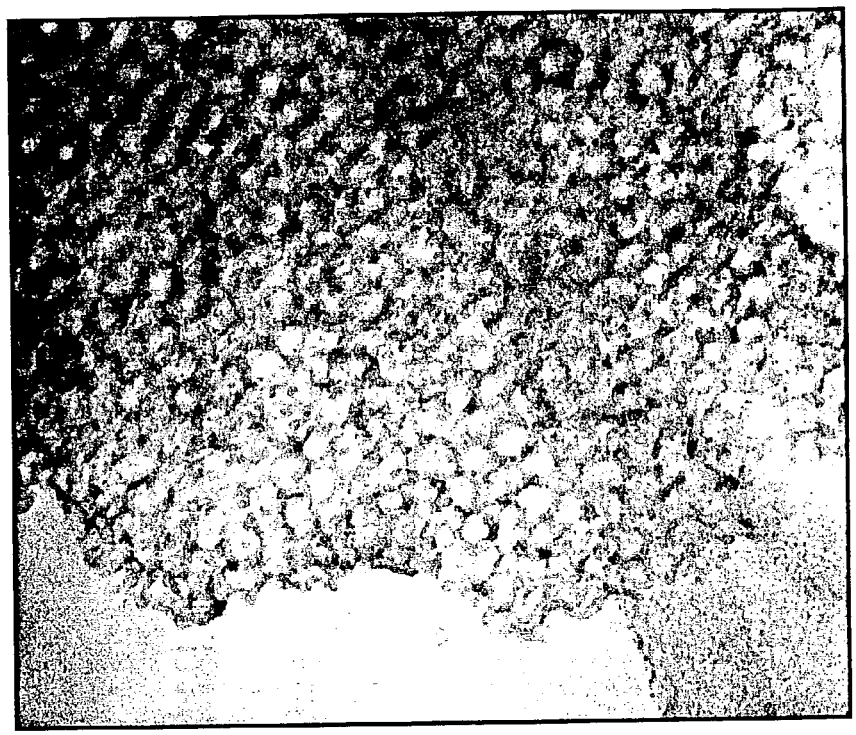
FIG. 27a  20 nm
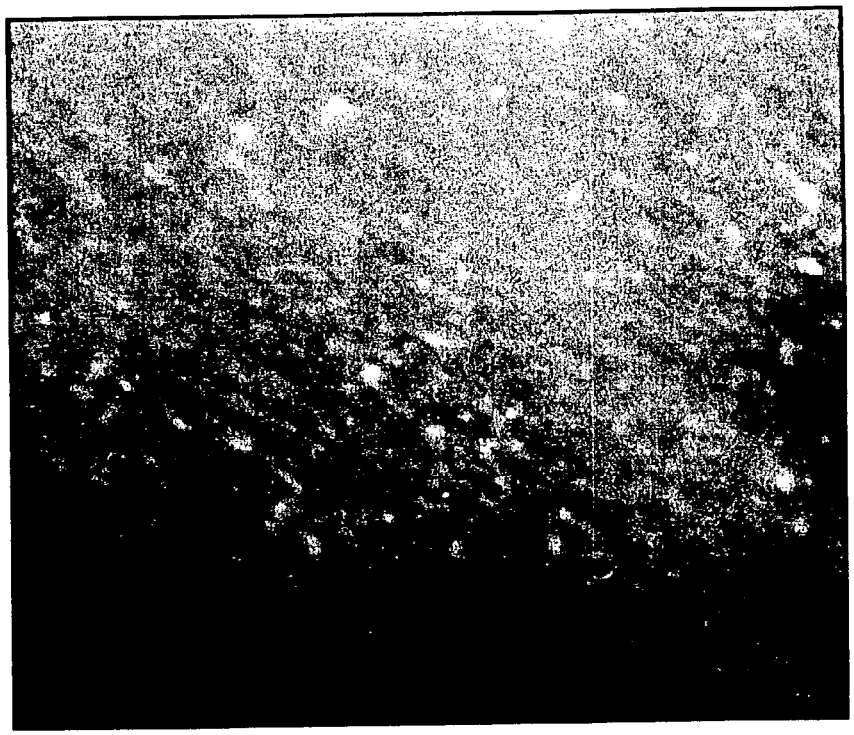
FIG. 27b  20 nm

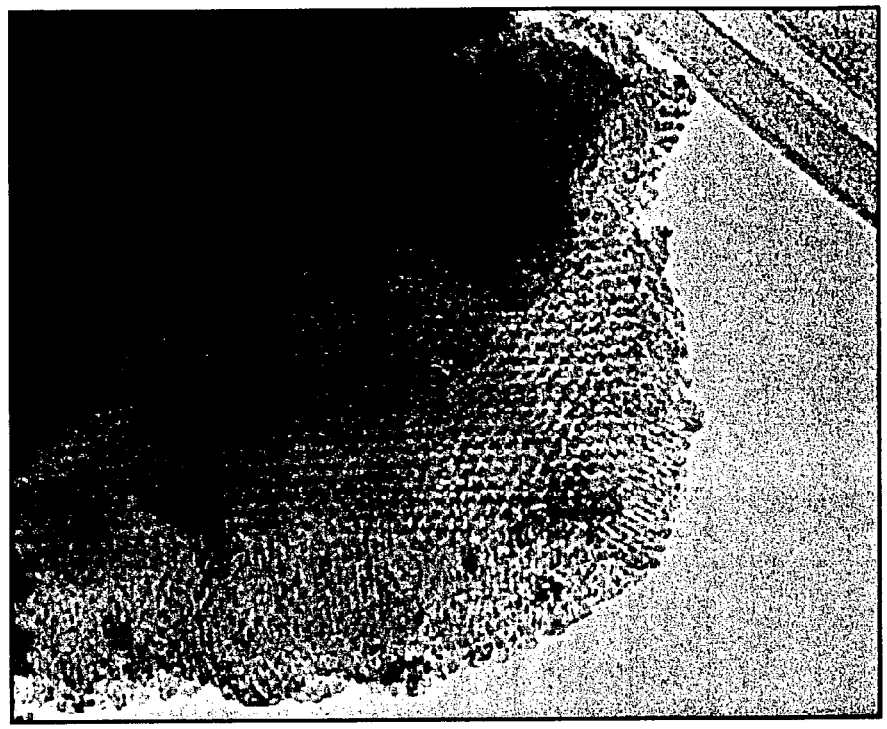
FIG. 28a  50 nm
FIG. 28b

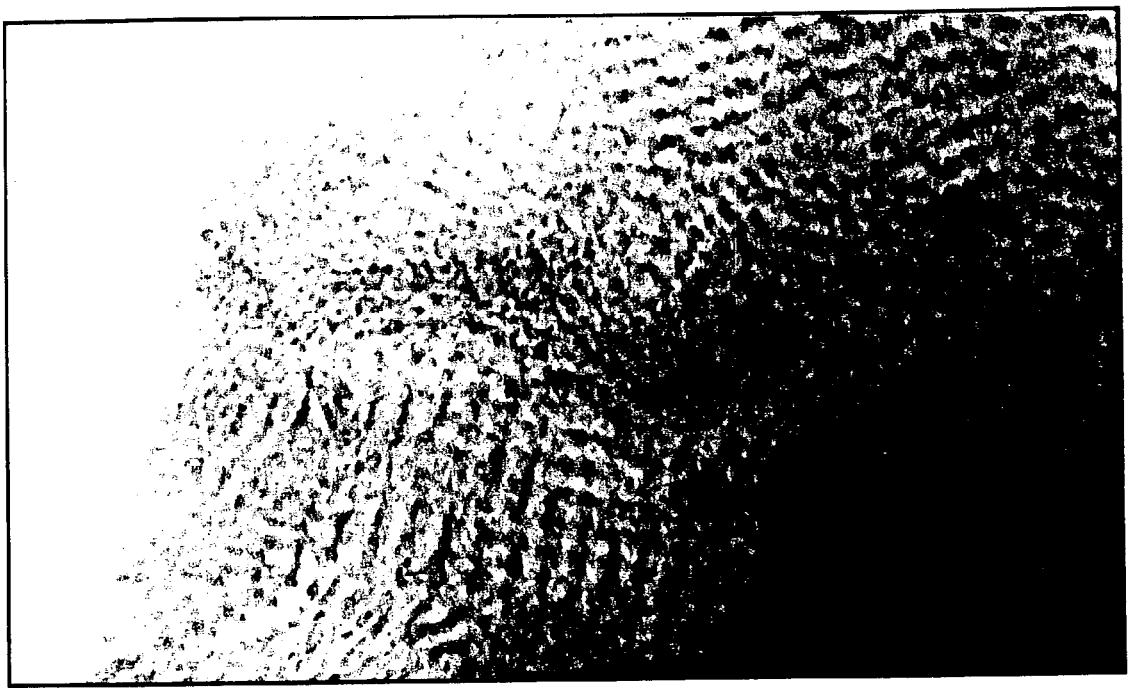
FIG. 38  20 nm

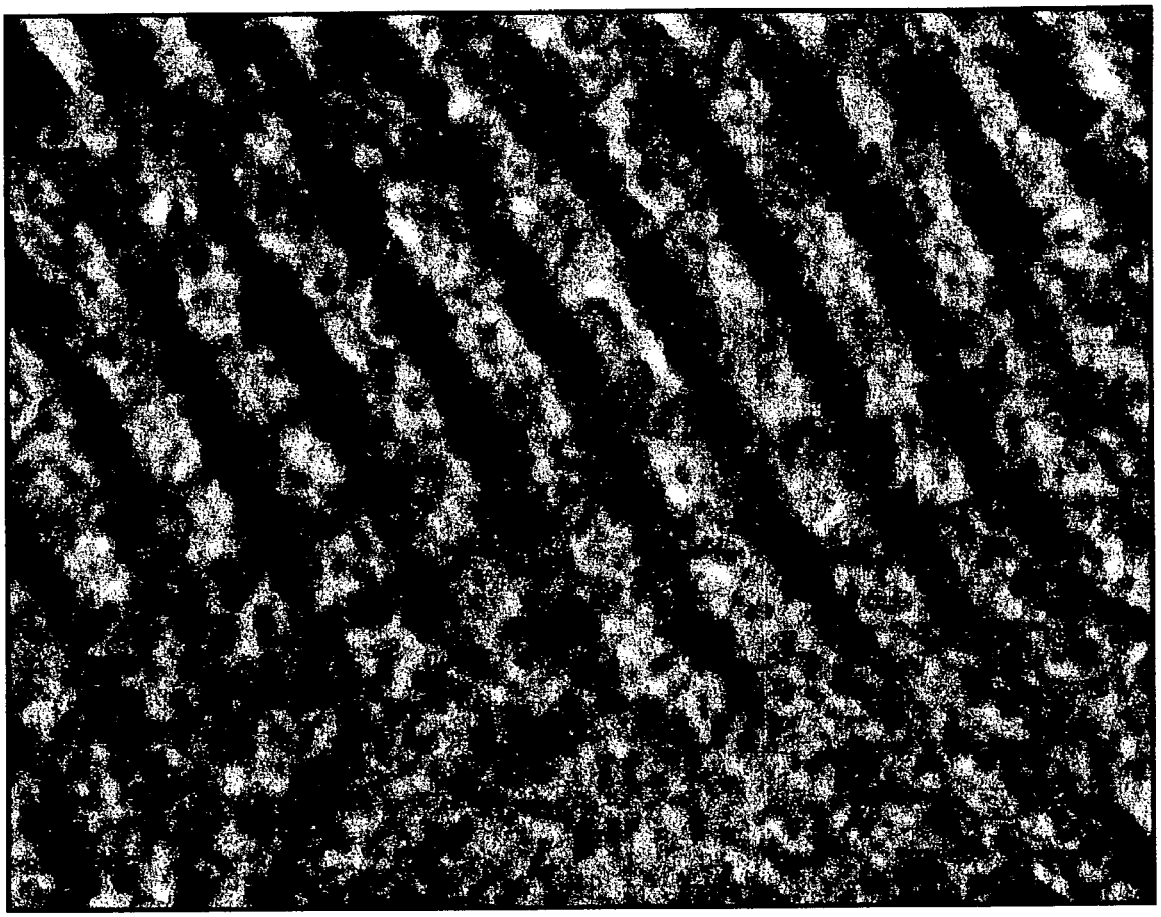
FIG. 39    20 nm

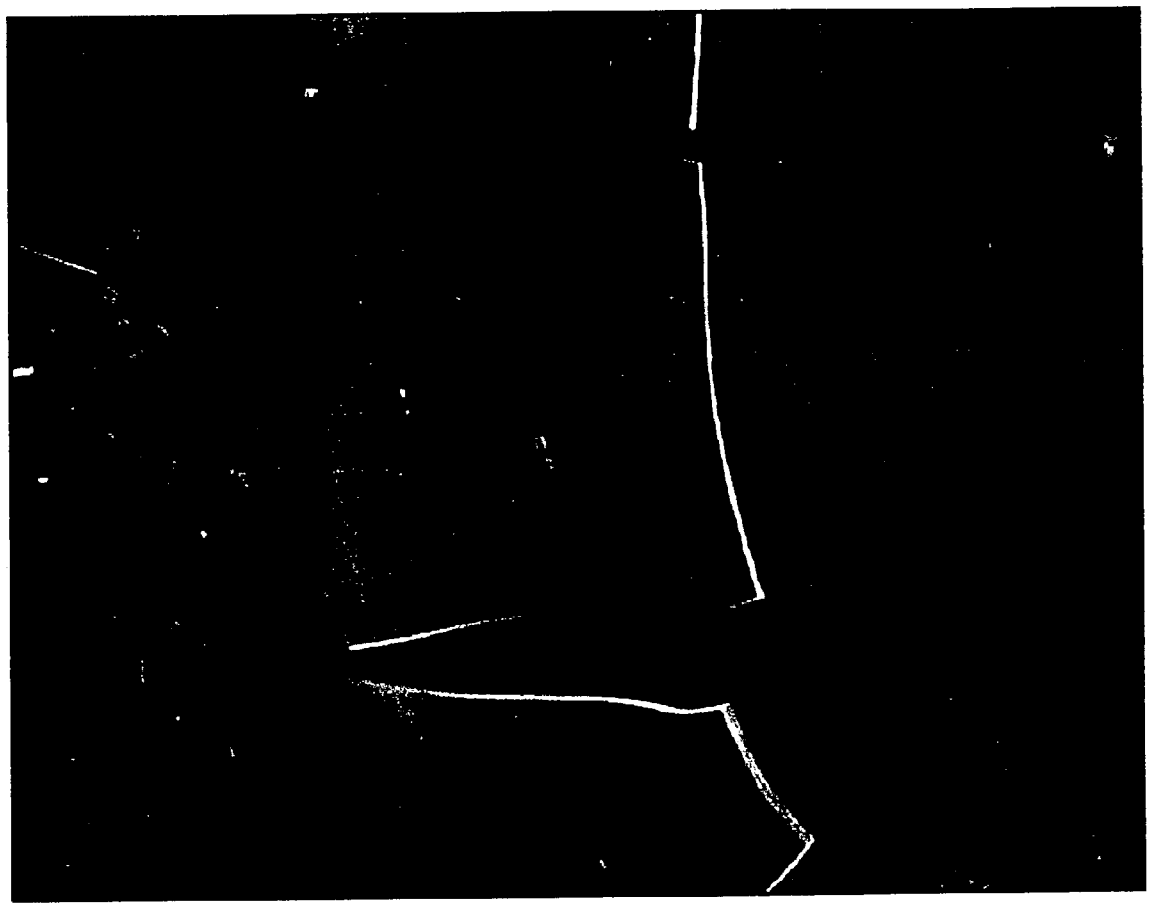
FIG. 40  10 μm

———— 10 μm
0 kV X 3.000  12mm

══
0.1 mm

══
1 nm

——— 10 μm
3.0 kV x 1,300  10mm

▭ 10 μm

— 1 μm
3.0 kV x 5,500  11mm

10 μm
JEOL    3.0 kV  X 2.530  12mm

— 1 μm
3.0 kV  X 5.000  12mm

10 μm
3.0 kV  X 2.700  11mm

100 μm
JEOL    3.0 kV  X 160  1.1mm

— 1 μm
3.0 kV  X  4,000  12mm

— 10 μm
3.0 kV  X  1,000  12mm

— 1 μm
3.0 kV  X  20,000  11mm

— 10 μm
3.0 kV  X  500  11mm

——— 100 μm
3.00 kV  X  250  12mm

——— 100 μm
3.00 kV  X  250  12mm

— 10 μm
3.00 kV  X  3.300  12mm

——— 10 μm
3.00 kV  X  3.300  12mm 0.1 mm

10 μm 3.0 kV X 3,000 12mm 50 nm

BLOCK COPOLYMER PROCESSING FOR MESOSTRUCTURED INORGANIC OXIDE MATERIALS

CROSS-REFERENCE TO CO-PENDING APPLICATION

This application is a continuation of U.S. Non-Provisional Application No. 09/554,259 filed on Dec. 11, 2000 now U.S. Pat. No. 6,592,764 which claimed the benefit of PCT/U.S. 98/26201, filed Dec. 9, 1998, and also claimed the benefit of U.S. Provisional Application Nos. 60/069,143, filed Dec. 9, 1997, and 60/097,012, filed Aug. 18, 1998.

STATEMENT REGARDING FEDERALLY FUNDED RESEARCH OR DEVELOPMENT

This invention was made with Government support under Grant Nos. DMR 9257064, DMR 9520971 and DMR 9632716 from the National Science Foundation, and Grant No. DAAH-04-96-1-0443 from the United States Army Research Office. The Government has certain rights in this invention.

BACKGROUND OF THE INVENTION

Large pore size molecular sieves are in high demand for reactions or separations involving large molecules and have been sought after for several decades. Due to their low cost, ease of handling, and high resistance to photoinduced corrosion, many uses have been proposed for mesoporous metal oxide materials, such as $SiO_2$, particularly in the fields of catalysis, molecular separations, fuel cells, adsorbents, patterned-device development, optoelectronic devices, and chemical and biological sensors. One such application for these materials is the catalysis and separation of molecules that are too large to fit in the smaller 3–5 Å pores of crystalline molecular sieves, providing facile separation of biomolecules such as enzymes and/or proteins. Such technology would greatly speed processing of biological specimens, eliminating the need for time consuming ultracentrifugation procedures for separating proteins. Other applications include supported-enzyme biosensors with high selectivity and antigen expression capabilities. Another application, for mesoporous $TiO_2$, is photocatalytic water splitting, which is extremely important for environmentally friendly energy generation. There is also tremendous interest in using mesoporous $ZrO_2$, $Si_{1-x}Al_xO_y$, $Si_{1-x}Ti_xO_y$, as acidic catalysts. Mesoporous $WO_3$ can be used as the support for ruthenium, which currently holds the world record for photocatalytic conversion of $CH_4$ to $CH_3OH$ and $H_2$. Mesoporous materials with semiconducting frameworks, such as $SnO_2$ and $WO_3$, can be also used in the construction of fuel cells.

Mesoporous materials in the form of monoliths and films have a broad variety of applications, particularly as thermally stable low dielectric coatings, non-linear optical media for optical computing and self-switching circuits, and as host matrices for electrically-active species (e.g. conducting and lasing polymers and light emitting diodes). Such materials are of vital interest to the semiconductor and communications industries for coating chips, as well as to develop optical computing technology which will require optically transparent, thermally stable films as waveguides and optical switches.

These applications, however, are significantly hindered by the fact that, until this invention, mesoscopically ordered metal oxides could only be produced with pore sizes in the range (15–100 Å), and with relatively poor thermal stability. Many applications of mesoporous metal oxides require both mesoscopic ordering and framework crystallinity. However, these applications have been significantly hindered by the fact that, until this invention, mesoscopically ordered metal oxides generally have relative thin and fragile channel walls.

Since mesoporous molecular sieves, such as the M41S family of materials, were discovered in 1992, surfactant-templated synthetic procedures have been extended to include a wide variety of compositions and conditions for exploiting the structure-directing functions of electrostatic and hydrogen-bonding interactions associated with amphiphilic molecules. For example, MCM-41 materials prepared by use of cationic cetyltrimethylammonium surfactants commonly have d(100) spacings of about 40 Å with uniform pore sizes of 20–30 Å. Cosolvent organic molecules, such as trimethylbenzene (TMB), have been used to expand the pore size of MCM-41 up to 100 Å, but unfortunately the resulting products possess less resolved XRD diffraction patterns. This is particularly the case concerning materials with pore sizes near the high-end of this range (ca. 100 Å) for which a single broad diffraction peak is often observed. Pinnavaia and coworkers, infra, have used non-ionic surfactants in neutral aqueous media ($S^0I^0$ synthesis at pH=7) to synthesize worm-like disordered mesoporous silica with somewhat larger pore sizes of 20–58 Å (the nomenclature $S^0I^0$ or $S^+I^-$ are shorthand notations for describing mesophase synthesis conditions in which the nominal charges associated with the surfactant species S and inorganic species I are indicated). Extended thermal treatment during synthesis gives expanded pore sizes up to 50 Å; see D. Khushalani, A. Kuperman, G. A. Ozin, *Adv. Mater.* 7, 842 (1995).

The preparation of films and monolithic silicates using acidic sol-gel processing methods is an active research field, and has been studied for several decades. Many studies have focused on creating a variety of hybrid organic-silicate materials, such as Wojcik and Klein's polyvinyl acetate toughening of TEOS monoliths (Wojcik, Klein; SPIE, *Passive Materials for Optical Elements II*, 2018, 160–166 (1993)) or Lebeau et al's organic-inorganic optical coatings (B. Lebeau, Brasselet, Zyss, C. Sanchez; *Chem Mater.*, 9, 1012–1020 (1997)). The majority of these studies use the organic phase to provide toughness or optical properties to the homogeneous (non-mesostructured) monolithic composite, and not as a structure-directing agent to produce mesoscopically ordered materials. Attard and coworkers have reported the creation of monoliths with ~40 Å pore size, which were synthesized with low molecular weight nonionic surfactants, but did not comment on their thermal stability or transparency; see G. S. Attard; J. C. Glyde; C. G. G6ltner, C. G. *Nature* 378, 366 (1995). Dabadie et al. have produced mesoporous films with hexagonal or lamellar structure and pore sizes up to 34 Å using cationic surfactant species as structure-directing species; see Dabadie, Ayral, Guizard, Cot, Lacan; *J. Mater Chem.*, 6, 1789–1794, (1996). However, large pore size (>50 Å) monoliths or films have not been reported, and, prior to our invention, the use of block copolymers as structure-directing agents has not been previously explored.(after our invention, Templin et al. reported using amphiphilic block copolymers as the structure-directing agents, aluminosilicate mesostructures with large ordering lengths (>15 nm); see Templin, M., Franck, A., Chesne, A. D., Leist, H., Zhang, Y., Ulrich, R., Schadler, V., Wiesner, U. Science 278, 1795 (Dec. 5, 1997)). For an overview of advanced hybrid organic-silica composites, see Novak's review article, B. Novak; *Adv. Mater.*, 5, 422–433 (1993).

While the use of low-molecular weight surfactant species have produced mesostructurally ordered inorganic-organic composites, the resulting materials have been in the form of powders, thin films, or opaque monoliths. Extension of prior art surfactant templating procedures to the formation of nonsilica mesoporous oxides has met with only limited success, although these mesoporous metal oxides hold more promise in applications that involve electron transport and transfer or magnetic interactions. The following mesoporous inorganic oxides have been synthesized with small mesopore sizes (<4 nm) over the past few years:

$MnO_2$ (Tian, Z., Tong, W., Wang, J., Duan, N., Krishnan, V. V., Suib, S. L. *Science*.

$Al_2O_3$ (Bagshaw, S. A., Pinnavaia, T. J. *Angew. Chem. Int. Ed. Engl.* 35, 1102 (1996)), $TiO_2$ (Antonelli, D. M., Ying, J. Y. *Angew. Chem. Int. Ed. Engl.* 34, 2014 (1995)), $Nb_2O_5$ (Antonelli, D. M., Ying, J. Y. *Chem. Mater.* 8, 874 (1996)), $Ta_2O_5$ (Antonelli, D. M., Ying, J. Y. *Chem. Mater.* 8, 874 (1996)), $ZrO_2$ (Ciesla, U., Schacht, S., Stucky, G. D., Unger, K. K., Schüth, F. *Angew. Chem. Int. Ed. Engl.* 35, 541 (1996)).

$HfO_2$ (Liu, P., Liu, J., Sayari, A. *Chem. Commun.* 557 (1997)), and reduced Pt (Attard, G. S., Barlett P. N., Coleman N. R. B., Elliott J. M., Owen, J. R., Wang, J. H. *Science*, 278, 838 (1997)).

However these often have only thermally unstable mesostructures; see Ulagappan, N., Rao, C. N. R. *Chem Commun.* 1685 (1996), and Braun, P. V., Osenar, P., Stupp, S. I. *Nature* 380, 325 (1996).

Stucky and co-workers first extended the surfactant templating strategy to the synthesis of non-silica-based mesostructures, mainly metal oxides. Both positively and negatively charged surfactants were used in the presence of water-soluble inorganic species. It was found that the charge density matching between the surfactant and the inorganic species is very important for the formation of the organic-inorganic mesophases. Unfortunately, most of these non-silica mesostructures are not thermally stable. Pinnavaia and co-workers, supra, used nonionic surfactants to synthesize mesoporous alumina in neutral aqueous media and suggested that the wormhole-disordered mesoporous materials are assembled by hydrogen-bonding interaction of inorganic source with the surfactants. Antonelli and Ying, supra, prepared stable mesoporous titanium oxide with phosphorus in a framework using a modified sol-gel method, in which an organometallic precursor was hydrolyzed in the presence of alkylphosphate surfactants. Mesoporous zirconium oxides were prepared using long-chain quaternary ammonium, primary amines, and amphoteric cocamidopropyl betaine as the structure-directing agents, see Kim, A., Bruinsma, P., Chen, Y., Wang, L., Liu, J. *Chem. Commun.* 161 (1997); Pacheco, G., Zhao, E., Garcia, A., Sklyaro, A., Fripiat, J. J. *Chem. Commun.* 491 (1997); and Pacheco G., Zhao, E., Garcia, A., Skylyarov, A., Fripiat, J. J. *J. Mater. Chem.* 8, 219 (1998).

A scaffolding process was also developed by Knowles et al. for the preparation of mesoporous $ZrO_2$ (Knowles J. A., Hudson M. J. *J. Chem. Soc., Chem. Commun.* 2083 (1995)). Porous $HfO_2$ has been synthesized using cetyltrimethylammonium bromide as the structure-directing agent; see Liu, P., Liu. J., Sayari, A. *Chem. Commun.* 557 (1997). Suib et al, supra, prepared mixed-valent semiconducting mesoporous maganese oxide with hexagonal and cubic structures and showed that these materials are catalytically very active. A ligand-assisted templating approach has been successfully used by Ying and co-workers, supra, for the synthesis of $Nb_2O_5$ and $Ta_2O_5$. Covalent bond interaction between inorganic metal species and surfactant was utilized in this process to assemble the mesostructure. More recently, the surfactant templating strategy has been successfully extended to platinum by Attard, Barlett et al, supra.

For all these mesoporous non-silica oxides (except Pinnavaia's alumina work, in which copolymers were used to produce mesoporous alumina in neutral aqueous conditions), low-molecular-weight surfactants were used for the assembly of the mesostructures, and the resulting mesoporous materials generally had small mesopore sizes (<4 nm), and thin (1–3 nm) and fragile frameworks. The channel walls of these mesoporous metal oxides were exclusively amorphous. There have been claims, based solely on the X-ray diffraction data, of mesoporous $ZrO_2$ and $MnO_2$ with crystalline frameworks; see Bagshaw and Pinnavaia, supra, and Huang, Y., McCarthy, T. J., Sachtler, W. M. *Appl. Catal. A* 148, 135 (1996). However, the reported X-ray diffraction patterns cannot exclude the possibility of phase separation between the mesoporous and crystalline materials, and therefore their evidence has been inconclusive. In addition, most of the syntheses were carried out in aqueous solution using metal alkyoxides as inorganic precursors. The large proportion of water makes the hydrolysis and condensation of the reactive metal alkyoxides and the subsequent mesostructure assembly extremely difficult to control.

For an overview of the non-silica mesoporous materials prior to this invention, see the Sayari and Liu review article, Sayari, A., Liu, P. *Microporous Mater.* 12, 149 (1997).

There has also been a need for porous inorganic materials with structure function on different length scales, for use in areas as diverse as large-molecule catalysis, biomolecule separation, the formation of semiconductor nanostructure, the development of medical implants and the morphogenesis of skeletal forms. The use of organic templates to control the structure of inorganic solid has proven very successful for designing porous materials with pore size ranging from angstroms to micrometers. For example, microporous aluminosilicate and aluminophosphate zeolite-type structures have been templated by organic molecules such as amines. Larger mesoporous (20~300 Å) materials have been obtained by using long-chain surfactant as structure-directing-agents. Recent reports illustrate that techniques such as surfactant emulsion or latex sphere templating have been used to create $TiO_2$, $ZrO_2$, $SiO_2$ structures with pore sizes ranging from 100 nm to 1 μm. Recently, Nakanishi used a process that combined phase separation, solvent exchange with sol-gel chemistry to prepare macroscopic silica structures with random meso and macro-porous structure; see K. Nakanishi, *J. Porous Mater.* 4, 67 (1997). Mann and coworkers used bacterial threads as the templates to synthesize ordered macrostructures in silica-surfactant mesophases; see Davis, S. L. Burkett, N. H. Mendelson, S. Mann, *Nature*, 385, 420 (1997)

Researchers have commented on the assembly of inorganic composites directed by protein or organic surfactants, but little on the effect of inorganic salts on the self-assembly of macroscopic silica or calcium carbonate structures with diatom, coral morphologies; see Davis, S. L. Burkett, N. H. Mendelson, S. Mann, *Nature*, 385, 420 (1997); A. M. Belcher, X. H. Wu, R. J. Christensen, P. K. Hansma. G. D. Stucky, *Nature*, 381, 56 (1996); and X. Y. Shen, A. M. Belcher, P. K. Hansma, G. D. Stucky, et al., *Bio. Chem.*, 272, 32472 (1997).

BRIEF SUMMARY OF THE INVENTION

The present invention overcomes the drawbacks of prior efforts to prepare mesoporous materials and mesoscopic structures, and provides heretofore unattainable materials having very desirable and widely useful properties. These materials are prepared by using amphiphilic block copolymer species to act as structure-directing agents for metal oxides in self-assembling systems. Aqueous metal cations partition within the hydrophilic regions of the self-assembled system and associate with the hydrophilic polymer blocks. Subsequent polymerization of the metalate precursor species under strongly acidic conditions (e.g., pH 1), produces a densely cross linked, mesoscopically ordered metal oxide network. Mesoscopic order is imparted by cooperative self-assembly of the inorganic and amphiphilic species interacting across their hydrophilic-hydrophobic interface.

By slowly evaporating the aqueous solvent, the composite mesostructures can be formed into transparent, crack-free films, fibers or monoliths, having two-dimensional hexagonal (p6 mm), cubic (Im3 m), or lamellar mesostructures, depending on choice of the block copolymers. Heating to remove the organic template yields a mesoporous product that is thermally stable in boiling water. Calcination yields mesoporous structures with high BET surface areas. Unlike traditional sol-gel films and monoliths, the mesoscopically ordered silicates described in this invention can be produced with high degrees of order in the 100–200 Å length scale range, extremely large surface areas, low dielectric constants, large anisotropy, can incorporate very large host molecules, and yet still retain thermal stability and the transparency of fully densified silicates In accordance with a further embodiment of this invention, inorganic oxide membranes are synthesized with three-dimension (3-d) meso-macro structures using simultaneous multiphase assembly. Self-assembly of polymerized inorganic oxide species/amphiphilic block copolymers and the concurrent assembly of highly ordered mesoporous inorganic oxide frameworks are carried out at the interface of a third phase consisting of droplet of strong electrolyte inorganic salts/water solution. The result is a 2-d or 3-d macroporous/mesoporous membranes which, with silica, are coral-like, and can be as large as 4 cm×4 cm with a thickness that can be adjusted between 10 μm to several millimeters. The macropore size (0.5–100 μm) can be controlled by varying the electrolyte strength of inorganic salts and evaporation rate of the solvents. Higher electrolyte strength of inorganic salts and faster evaporation result in a thicker inorganic oxide a framework and larger macropore size. The mesoscopic structure, either 2-d hexagonal (p6 mm, pore size 40~90 Å) or 3-d cubic array, can be controlled by amphiphilic block copolymer templates. The resulting membranes are thermally stable and have large surface areas up to 1000 m$^2$/g, and pore volume up to 1.1 cm$^3$/g. Most importantly, these meso-macroporous coral-like planes provide excellent access to the mesopore surfaces for catalytic, sorption, catalysis, separation, and sensor arrays, applications.

BRIEF DESCRIPTION OF THE DRAWINGS

FIG. 11 shows photographs of transparent SBA-15 silica-copolymer monoliths incorporating (a) 27 wt % and (b) 34 wt % of the PEO-PPO-PEO structure-directing copolymer PLURONIC F127.

FIG. 17 shows TEM micrographs of 2-dimensional hexagonal mesoporous $TiO_2$. (a) and (b) are recorded along the [110] and [001] zone axes, respectively. Inset in (a) is the selected-area electron diffraction pattern obtained on the image area.

FIG. 19 shows TEM micrographs of 2-dimensional hexagonal mesoporous $WO_3$. (a) and (b) are recorded along the [110] and [001] zone axes, respectively.

FIG. 20 shows TEM micrograph of 2-dimensional hexagonal mesoporous $Nb_2O_5$, recorded along the [001] zone axis. Inset is selected-area electron diffraction pattern obtained on the image area.

FIG. 22 shows TEM micrographs of disordered hexagonal mesoporous $Al_2O_3$.

FIG. 23 shows TEM micrographs of 2-dimensional hexagonal mesoporous $HfO_2$ recorded along the [110] zone axis.

FIG. 24 shows TEM micrographs of 2-dimensional hexagonal mesoporous $SiAlO_4$ recorded along the [001] zone axis.

FIG. 25 shows TEM micrographs of 2-dimensional hexagonal mesoporous $SiAlO_{3.5}$. (a) and (b) are recorded along the [110] and [001] zone axes, respectively.

FIG. 27 shows (a) Bright field TEM image of a thin slice of the mesoporous $TiO_2$ sample. (b) Dark field image obtained on the same area of the same $TiO_2$ sample. The bright spots in the image correspond to $TiO_2$ nanocrystals.

FIG. 28 shows (a) Bright field TEM image of a thin slice of the mesoporous $ZrO_2$ sample. (b) Dark field image obtained on the same area of the same $ZrO_2$ sample. The bright spots in the image correspond to $ZrO_2$ nanocrystals.

FIG. 38 shows TEM micrograph of cubic mesoporous $TiO_2$.

FIG. 39 shows TEM micrograph of cubic mesoporous $ZrO_2$.

FIG. 40 shows SEM image of calcined mesoporous $Al_2O_3$ monolithic thick film. The image was recorded on JEOL 6300 FX microscope.

DETAILED DESCRIPTION OF THE INVENTION

Figure 1A:
FIG. 1 shows a size comparison between two prior art porous inorganic materials, Faujasite and MCM-41, and SBA-15, prepared in accordance with this invention.

This invention provides a simple and general procedure for the syntheses of ordered large-pore (up to 14 nm) mesoporous metal oxides, including $TiO_2$, $ZrO_2$, $Nb_2O_5$, $Ta_2O_5$, $Al_2O_3$, $SiO_2$, $WO_3$, $SnO_2$, $HfO_2$ and mixed oxides $SiAlO_{3.5}$, $SiAlO_{5.5}$, $Al_2TiO_5$, $ZrTiO_4$, $SiTiO_4$. Commercially available, low-cost, non-toxic, and biodegradable amphiphilic poly(alkylene oxide) block copolymers can be used as the structure-directing agents in non-aqueous solutions for organizing the network forming metal species. Preferably the block copolymer is a triblock copolymer in which a hydrophilic poly(alkylene oxide) such as poly (ethylene oxide ($EO_x$) is linearly covalent with the opposite ends of a hydrophobic poly(alkylene oxide) such as polypropylene) oxide ($PO_y$) or a diblock polymer in which, for example, poly(ethylene oxide) is linearly covalent with poly(butylene oxide) ($BO_y$). This can variously be designated as follows:

poly(ethylene oxide)-poly(propylene oxide)-poly(polyethylene oxide)

PEO-PPO-PEO
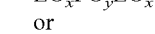

or poly(ethylene oxide)poly(butylene oxide)-poly(polyethylene oxide)

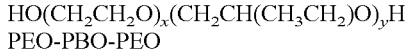
PEO-PBO-PEO

where x is 5 or greater and y is 30 or greater, with no theoretical upper limit to either value subject to practical considerations. Alternatively, for particular applications, one can use a reverse triblock copolymer or a star block amphiphilic poly(alkylene oxide block copolymer, for example, a star di-block copolymer or a reversed star di-block copolymer. Inexpensive inorganic salts rather than alkoxides or organic metal complexes are used as precursors. Both two-dimensional hexagonal (p6 mm) and cubic (Im3 m) mesostructures can be obtained, as well as lamellar mesostructures, depending on the choice of the block copolymers. Calcination at 400° C. yields mesoporous structures with high BET surface area (100–850 m² µg), porosity of 40–65%, large d spacings (60–200 Å), pore sizes of 30–140 Å, and wall thickness of 30–90 Å.

These novel mesoporous metal oxides are believed to be formed through a mechanism that combines block copolymer self-assembly with chelating complexation of the inorganic metal species. A unique aspect of these thermally stable mesoporous oxides is their robust inorganic framework and thick channel walls, within which a high density of nanocrystallite s can be nucleated during calcination without disrupting the mesoscopic ordering. In addition, variations of this simple sol-gel process yield mesoporous oxides with technologically important forms including thin films, monoliths and fibers. The nanocrystalline framework, periodic large-pore structures, and high versatility of the inexpensive synthetic methodology make these mesoporous materials an excellent choice for applications including catalysis, molecular separations, fuel cells, adsorbents, optoelectronic devices, and chemical and biological sensors. For example, due to its low cost, ease of handling, and high resistance to photoinduced corrosion, one application for mesoporous $TiO_2$ is photocatalytic water splitting, which is extremely important for environmentally friendly energy generation. There is also tremendous interest in using mesoporous $ZrO_2$, $Si_{1-x}Al_xO_y$, $Si_{1-x}Ti_xO_y$ as acidic catalysts. Mesoporous $WO_3$ can be used as the support for ruthenium, which currently holds the world record for photocatalytic conversion of $CH_4$ to $CH_3OH$ and $H_2$. Mesoporous materials with semiconducting frameworks, such as $SnO_2$ and $WO_3$, can be also used in the construction of fuel cells.

Many applications of mesoporous metal oxides require both mesoscopic ordering and framework crystallinity. The mesoporous metal oxides of this invention are thermally stable and retain their mesoscopic ordering and structural integrity even after the nucleation of the high density of nanocrystallites within thick, robust channel walls. Development of such thermally stable, large-pore mesoporous metal oxide materials with nanocrystalline frameworks using lowcost, non-toxic, and biodegradable polyalkylene oxide block copolymers has enormous potential for a variety of immediate and future industrial applications.

In practicing this invention, one can use any amphiphilic block polymer having substantial hydrophilic and hydrophobic components and can use any inorganic material that can form crown-ether-type complexes with alkylene oxide segments through weak coordination bonds. The inorganic material can be any inorganic compound of a multivalent metal species, such as metal oxides and sulphides, preferably the oxides. The metal species preferentially associates with the hydrophilic poly(ethylene oxide) (PEO) moieties. The resulting complexes then self-assemble according to the mesoscopic ordering directed principally by microphase separation of the block copolymer species. Subsequent crosslinking and polymerization of the inorganic species occurs to form the mesoscopically ordered inorganic/block-copolymer composites. The proposed assembly mechanism for these diverse mesoporous metal oxides uses PEO-metal complexation interactions, in conjunction with (for example) electrostatic, hydrogen bonding, and van der Waals forces to direct mesostructure formation.

As Indicated above, one can carry out the assembly process in non-aqueous media using metal halides as the inorganic precursors, which effectively slows the hydrolysis/condensation rates of the metal species and hinders subsequent crystallization. Restrained hydrolysis and condensation of the inorganic species appears to be important for forming mesophases of most of the non-silica oxides, because of their strong tendency to precipitate and crystallize into bulk oxide phases directly in aqueous media.

The procedures of the present invention enable close control of the porosity of the final structure by varying the proportions of PEO and PPO or PBO and by adding an organic solvent to swell the PPO or PBO.

Because of their low cost, widespread use, and ease of preparation, we will first describe and exemplify the preparation of mesoporous silica, followed by the preparation of other metal oxides. We will then describe the multiphase assembly of meso-macro membranes, which we will exemplify with silica membranes.

Mesoporous Silicas

In accordance with this invention, we have synthesized a family of high quality, hydrothermally stable and ultra large pore size mesoporous silicas by using amphiphilic block copolymers in acidic media. One member of the family, to which we have assigned the designation SBA-15, has a highly ordered, two-dimensional hexagonal (p6 mm) honeycomb, hexagonal cage or cubic cage mesostructures. Calcination at 500° C. yields porous structures with high BET surface areas of 690–1040 $m^2/g$, and pore volumes up to 2.5 $cm^3/g$, ultra large d(100) spacings of 74.5–450 Å, pore sizes from 46–500 Å and silica wall thicknesses of 31–64 Å. SBA-15 can be readily prepared over a wide range of specific pore sizes and pore wall thicknesses at low temperature (35–80° C.) using a variety of commercially available, low-cost, non-toxic, and biodegradable amphiphilic block copolymers, including triblock polyoxyalkylenes, as described below. In general, all microphase-separating, domain-partitioning copolymer systems can be considered as candidates for the synthesis of such mesostructured materials, depending on solution composition, temperature, processing conditions, etc. The pore size and thickness of the silica wall is selectively controlled by varying the thermal treatment of SBA-15 in the reaction solution and by the addition of cosolvent organic molecules, such as 1,3,5-trimethylbenzene (TMB). The organic template can be easily removed by heating at 140° C. for 3 h, yielding the mesoporous SBA-15 product, which is thermally stable in boiling water.

Transparent films, fibers, and monolithic materials with mesoscopic order can also be prepared by a similar process utilizing the same family of triblock polyoxyalkylene copolymers, yielding mesoporous structure in bulk. These materials are similarly synthesized in acidic media at low temperatures (20–80° C.), and display a variety of well-ordered copolymer phases with mesostructures of about 100–500 Å. They can be processed (e.g., molded) into a variety of bulk shapes, which are also transparent. In addition, it is possible to use polymer processing strategies, such as shear alignment, spin casting, and fiber drawing to induce orientational order in these materials. After calcination at 350° C. these monoliths and films retain their macroscopic shape and mesoscopic morphology. To our knowledge, these are the first reported thermally stable, transparent, monolithic, large pore-size materials with well-ordered mesostructure. Their dielectric constants can be varied to low values via the Lorentz-Lorenz relationship by tuning the pore volume fraction from 0.6 to as much as 0.86. The fluid sol processability, extraordinary periodic pore and cage structures, high pore volume fraction and inexpensive synthesis make them excellent low dielectric materials for inter-level dielectrics (LID) for on-chip interconnects to provide high speed, low dynamic power dissipation and low cross-talk noise.

To produce the highly ordered, ultra large pore silica mesostructures we adopted an $S^+I^-X^-I^+$ synthesis processing strategy. This synthesis methodology is distinctly different from the $S^+I^-$ route (pH>3) used to make the M41S family of mesoporous materials: the two methods employ conditions that are on opposite sides of the isoelectric point of aqueous silica (pH=2). For example, mesoporous silica SBA-15 can be synthesized using block copolymers, which that have a polyoxyethylene-polyoxypropylene-polyoxyethylene (PEO-PPO-PEO) sequence centered on a (hydrophobic) polypropylene glycol nucleus terminated by two primary hydroxyl groups; see Table 1 The synthesis is carried out in acidic (e.g., HCl, HBr, $H_2SO_4$, $HNO_3$, $H_3PO_4$) media at 35-80° C. using either tetraethylortho-silicate (TEOS), tetramethylorthosilicate (TMOS), or tetrapropoxysilane (TPOS) as the silica source.

Hexagonal SBA-15 has a wheat-like macroscopic morphology, a highly ordered (four to seven peaks in the X-ray diffraction pattern), two-dimensional hexagonal (p6 mm) mesostructure, BET surface areas up to 1040 $m^2/g$, pore volumes to 2.5 $cm^3/g$, and thick silica walls (31–64 Å) The thick silica walls in particular are different from the thinner-walled MCM-41 mesostructures made with conventional low molecular weight cationic surfactants. The pore size and the thickness of the silica wall can be adjusted by varying the heating temperature (35–140° C.) or heating time (11–72 h) of the SBA-15 in the reaction solution and by adding organic swelling agents such as 1,3,5-trimethylbenzene The thick walls of the hexagonally ordered pores of these materials produce a novel combination of a high degree of both mesoscopic organization and hydrothermal stability. Based on the above properties, SBA-15 materials have potential applications in catalysis, separations, chemical sensors, and adsorbents.

Transparent films and monoliths have been synthesized with similar PEO-PPO-PEO copolymers as structure-directing agents in an acidic sol-gel reaction. These materials can be synthesized with various amounts of water, acid, silicate source, and polymer to yield different mesophase structures depending upon the polymer and processing conditions used. The materials consist of a collection of aggregates of an organic polymer component, such as the amphiphilic copolymer PLURONIC F127, which for a hexagonal array that organizes a polymerized silica matrix in the interstices between the polymer aggregates. Such morphologies are formed by interactions among the block copolymer and the oligomeric silicate species, and solidified as the silica polymerizes to form a monolithic structure. The polymer is not strongly incorporated into the silica walls, as inferred from the remarkably low temperature (150° C.) needed to remove the polymer, and supporting $^1$H nuclear magnetic resonance (NMR) relaxation measurements. These structures possess characteristic length scales of 100–200 Å and have very large domain sizes (>1 μm), yet retain good transparency. Upon calcination the monoliths become opaque, though retain their bulk shape and possess mesoscopically ordered, hexagonally arranged pores (100–200 Å diameter), which impart high internal surface areas to the materials (ca. 1000 m$^2$/g).

Synthesis of Highly Mesoscopically Ordered Ultra-large-pore, and Hydrothermally Stable Mesoporous Silica.

Figure 1B:
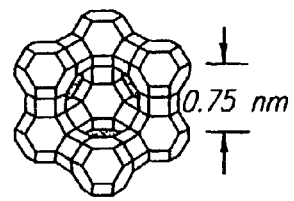
Figure 1C:
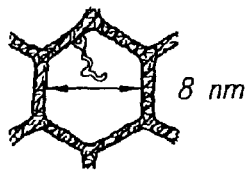
Figure 1D:
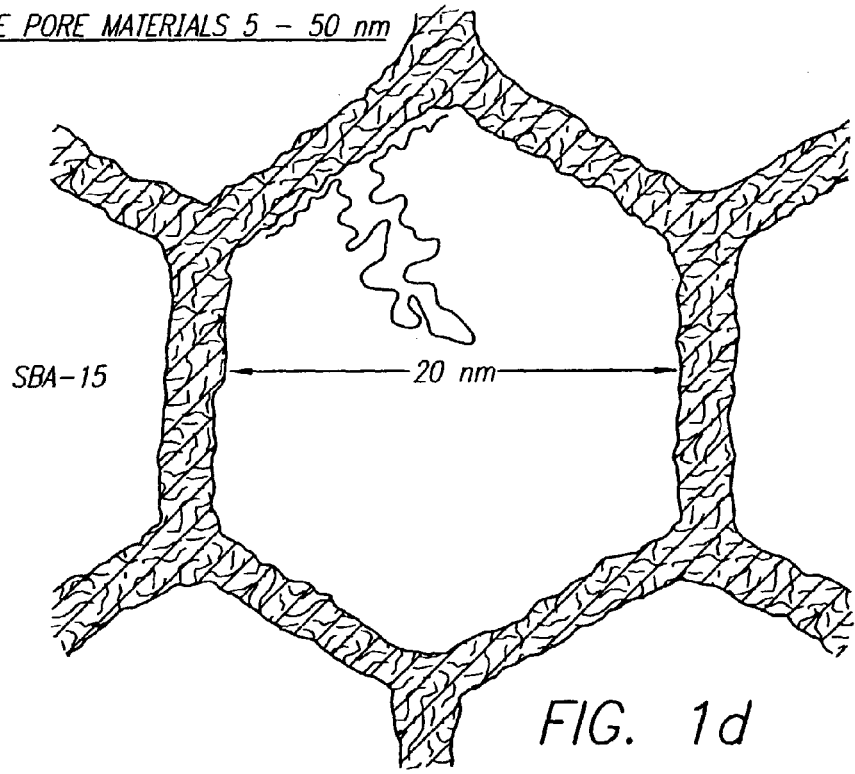

Referring to FIGS. 1a,b,c and d, there is shown, approximately to scale, two prior art inorganic oxide porous structures and the SBA-15 produced in accordance with this invention. As shown in FIGS. 1a and 1b Faujasite, a sub-nanoporous zeolite has a pore size of less than 1 nm. MCM-41, a mesoporous molecular sieve material, shown at FIG. 1c, has a pore size of about 8 nm. In contrast, as shown in FIG. 1d, SBA-15, the ultra large pore mesoporous silica material produced by this invention, has a pore size of about 20 nm, in this particular example.

Mesoporous silica SBA-15 was synthesized at 35–80° C. using a hydrophilic-hydrophobic-hydrophilic PEO-PPO-PEO triblock copolymer as the structure-directing-agent. 4.0 g of PLURONIC P123 (PEO$_{20}$PPO$_{70}$PEO$_{20}$) was dissolved in 30 g water and 120 g (2 M) HCl solution while stirring at 35° C. To the resulting homogeneous solution 8.50 g TEOS was added while stirring at 35° C. for 22 h. The mixture was then aged at 100° C. without stirring for 24 h. The solid product was filtered, washed, and air-dried at room temperature. Calcination was carried out in air by slowly increasing the temperature (from room temperature to 500° C. over 8 h) and heating at 500° C. for 6 h.

Figure 2A:
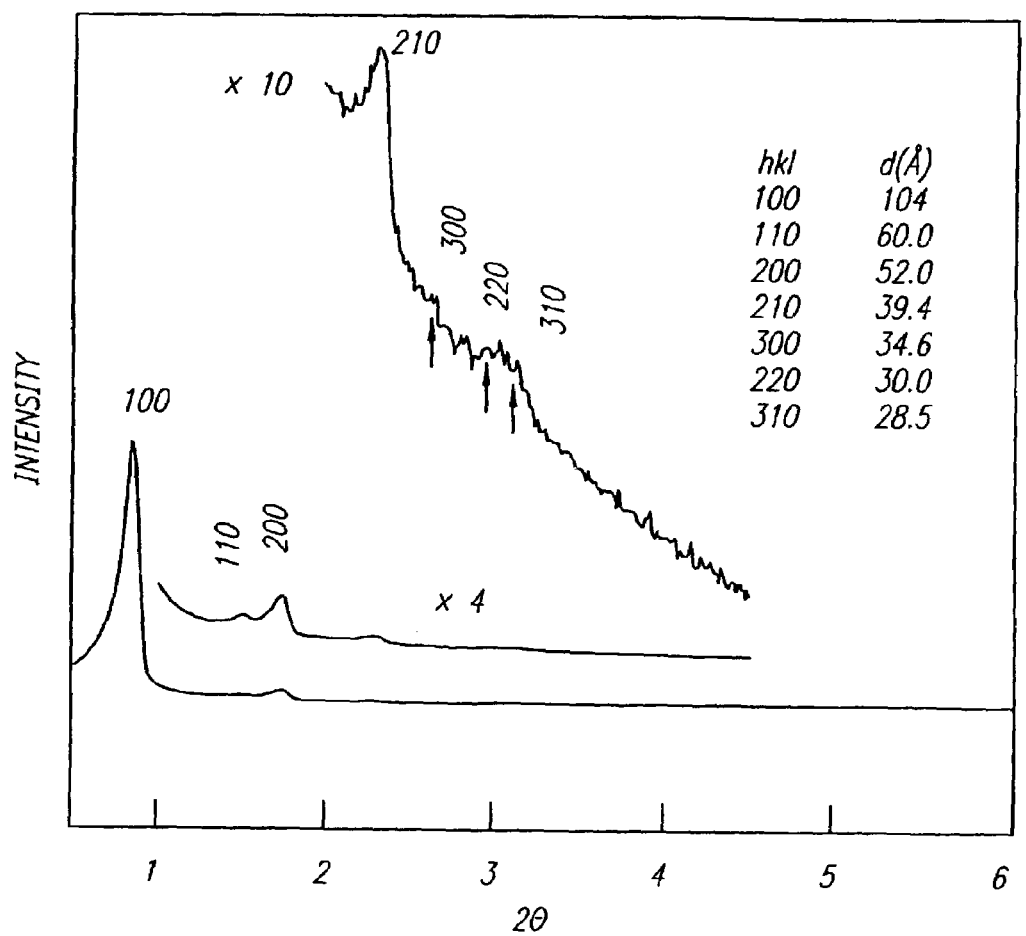
FIG. 2 shows powder X-ray diffraction (XRD) patterns of as-synthesized and calcined mesoporous silica (SBA-15) prepared using the amphiphilic polyoxyalkylene block copolymer $PEO_{20}PPO_{70}PEO_{20}$.
Figure 2B:
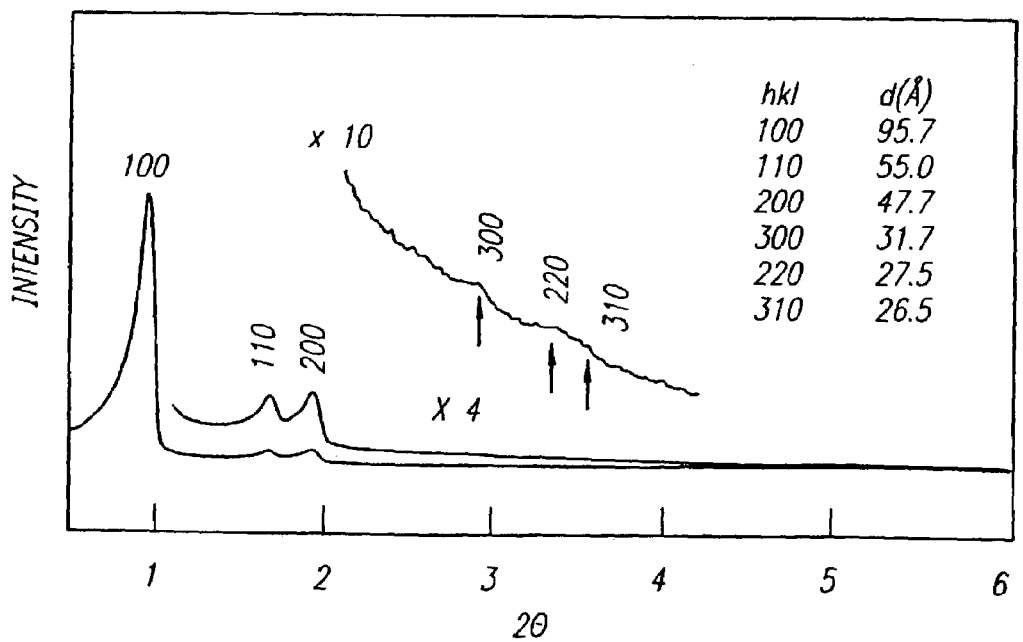

X-ray diffraction is an important means for characterizing the SBA-15 family of materials. FIGS. 2a and 2b show small-angle XRD patterns for as-synthesized and calcined hexagonal mesoporous silica SBA-15 prepared by using the polyoxyalkylene triblock copolymer PEO$_{20}$PPO$_{70}$PEO$_{20}$ (PLURONIC P123). The chemical composition of the reaction mixture was 4 g of the copolymer: 0.041 M TEOS: 0.24 M HCl: 6.67 M H$_2$O. The XRD patterns were acquired on a Scintag PADX diffractometer equipped with a liquid nitrogen cooled germanium solid-state detector using Cu Kα radiation. The X-ray pattern of as-synthesized hexagonal SBA-15 (FIG. 2a) shows four well-resolved peaks that are indexable as (100), (110), (200), and (210) reflections associated with p6 mm hexagonal symmetry. The as-synthesized SBA-15 possesses a high degree of hexagonal mesoscopic organization indicated by three additional weak peaks that are present in the 2Θ range of 1–350 corresponding to the (300), (220), and (310) scattering reflections, respectively. The intense (100) peak reflects a d-spacing of 104 Å, corresponding to a large unit cell parameter (a=120 Å). After calcination in air at 500° C. for 6 h, the XRD pattern (FIG. 2b) shows that the p6 mm morphology has been preserved, although the peaks appear at slightly higher 2Θ values with d(100)=95.7 Å and a cell parameter (a$_0$) of 110 Å. Six XRD peaks are still observed, confirming that hexagonal SBA-15 is thermally stable. A similarly high degree of mesoscopic order is observed for hexagonal SBA-15 even after calcination to 850° C.

Figure 3A:
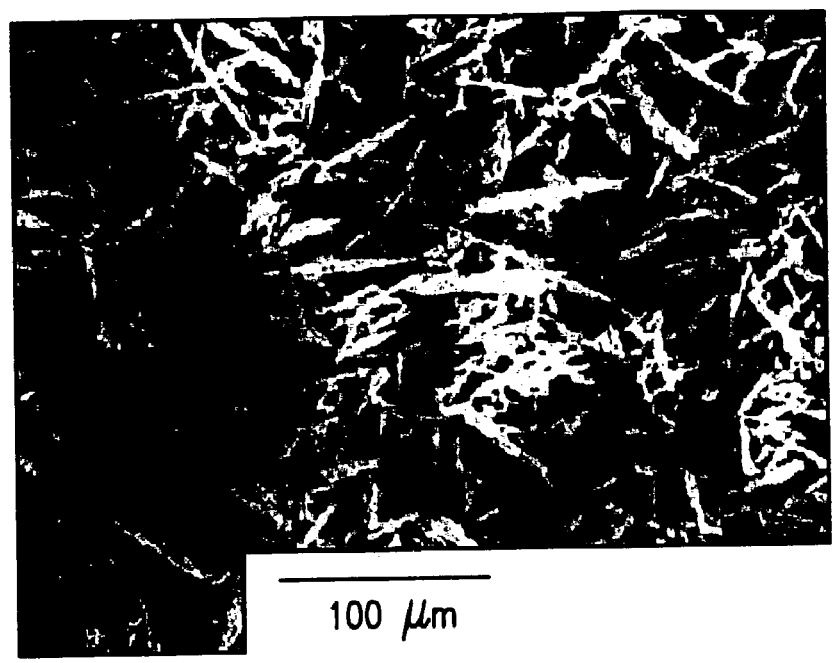
FIG. 3 shows scanning electron micrographs (SEM's) (a, b) of as-synthesized SBA-15 and transmission electron micrographs (TEM's) (c, d) with different orientations of calcined hexagonal mesoporous silica SBA-15 prepared using the block copolymer $PEO_{20}PPO_{70}PEO_{20}$.
Figure 3B:
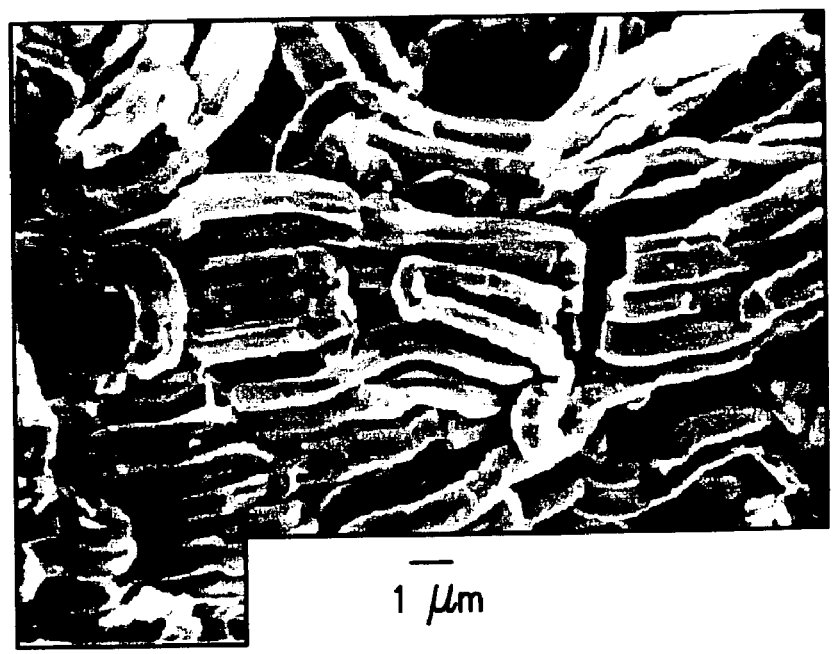
Figure 3C:
Figure 3D:
Figure 4A:
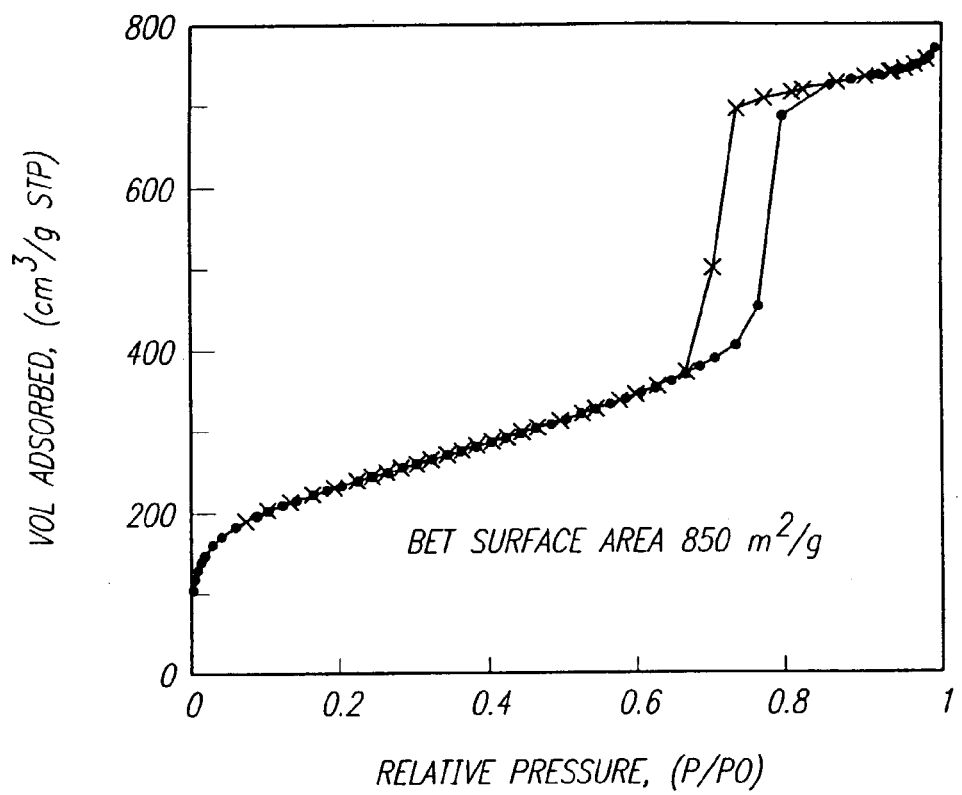
FIG. 4 shows nitrogen adsorption-desorption isotherm plots (top) and pore size distribution curves (bottom) measured using the adsorption branch of the isotherm for calcined mesoporous silica SBA-15 prepared using the block copolymer $PEO_{20}PPO_{70}PEO_{20}$ (a, b) without and (c, d) with TMB as an organic additive.
Figure 4B:
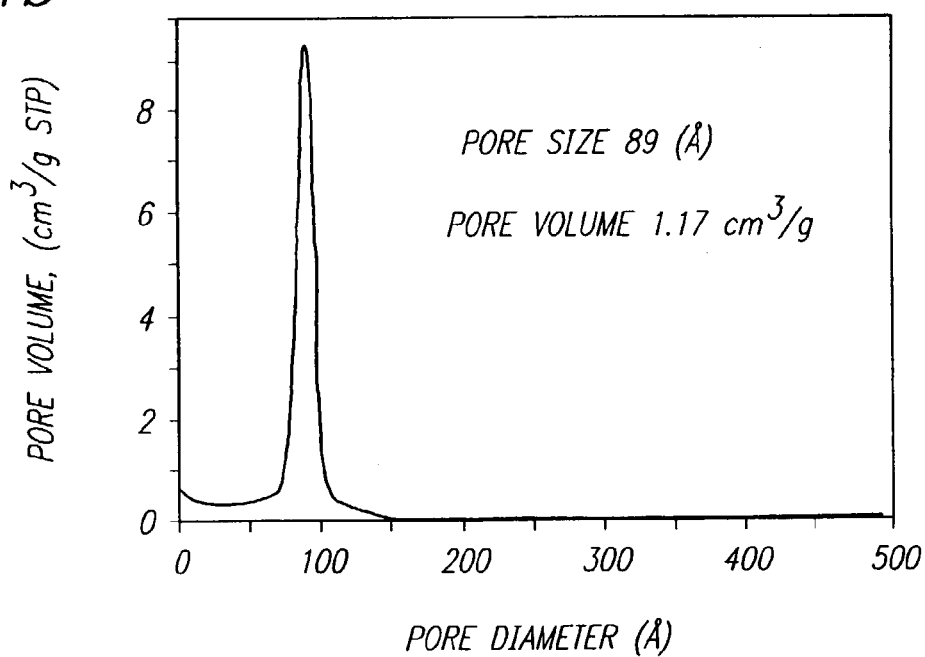
Figure 4C:
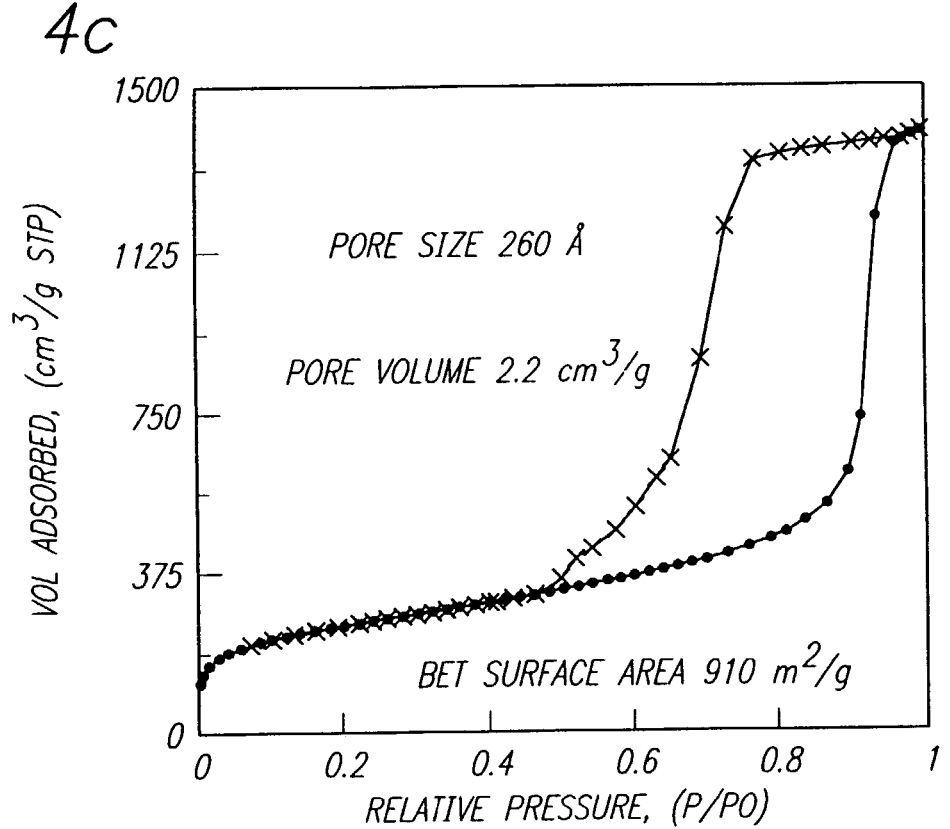
Figure 4D:
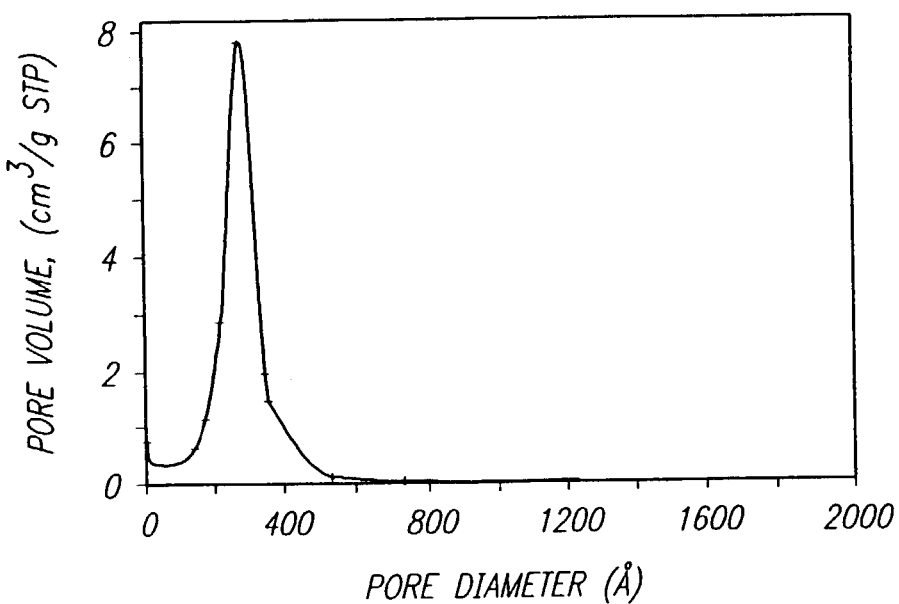

SEM images (FIGS. 3a, 3b) reveal that as-synthesized hexagonal SBA-15 has a wheat-like morphology with uniform particle sizes of about −80 μm, and that these consist of many rope-like macrostructures. The SEM's were obtained on a JEOL 6300-F microscope. Calcined hexagonal SBA-15 at 500° C. in air shows a similar particle morphology, reflecting the thermal stability of the macroscopic shape and structure. TEM images (FIGS. 3c, 3d) of calcined SBA-15 with different sample orientations show well ordered hexagonal arrays of mesopores (one-dimensional channels) and further confirm that SBA-15 has a two-dimensional p6 mm hexagonal structure. The TEM's were acquired using a 2000 JEOL electron microscope operating at 200 kV. For the TEM measurements, samples were prepared by dispersing the powder products as a slurry in acetone and subsequently deposited and dried on a holey carbon film on a Ni grid. From high-dark contrast in the TEM images, the distance between mesopores is estimated to be about 110 Å, in agreement with that determined from XRD data.

Nitrogen adsorption-desorption isotherm plots and the corresponding pore-size distribution curves are shown in FIG. 4 for calcined hexagonal SBA-15 samples that were prepared using the copolymer PEO$_{20}$PPO$_{70}$PEO$_{20}$. The sample corresponding to the measurements shown in FIGS. 4a and 4b was prepared by reaction at 35° C. for 20 h, heating at 100° C. for 48 h, and subsequent calcination in air at 500° C., yielding a hexagonal SBA-15 product material with a mean pore size of 89 Å, a pore volume of 1.17 cm$^3$/g, and a BET surface area of 850 m$^2$/g. The sample corresponding to the measurements shown in FIGS. 4c and 4d was prepared under identical conditions but additionally used TMB as an organic swelling agent to increase the pore size of the subsequent product material. Using TMB yields hexagonal mesoporous SBA-15 silica with a mean pore size of 260 Å, a pore volume of 2.2 cm$^3$/g, and a BET surface area of 910 m$^2$ μg. The isotherms were measured using a Micromeritics ASAP 2000 system. Data were analyzed by the BJH (Barrett-Joyner-Halenda) method using the Halsey equation for multilayer thickness. The pore size distribution curve was obtained from an analysis of the adsorption branch of the isotherm. The pore volumes were taken at P/P$_0$=0.983 signal point. Prior to the BET measurements, the samples were pretreated at 200° C. overnight on a vacuum line. In both FIGS. 4a and 4c, three well-distinguished regions of the adsorption isotherm are evident: (1) monolayer-multilayer adsorption, (2) capillary condensation, and (3) multilayer adsorption on the outer particle surfaces. In contrast to N2 adsorption results for MCM-41 mesoporous silica with pore sizes less than 40 Å, a clear type H$_1$ hysteresis loop in the adsorption-desorption isotherm is observed for hexagonal SBA-15 and the capillary condensation occurs at a higher relative pressure (P/P$_0$–0.75). The approximate pore size calculated using the BJH analysis is significantly smaller than the repeat distance determined by XRD, because the latter includes the thickness of the pore wall. Based on these results, the thickness of the pore wall is estimated to be ca. 31 Å (Table 1) for hexagonal SBA-15 prepared using the PEO$_{20}$PPO$_{70}$PEO$_{20}$ copolymer.

Figure 5A:
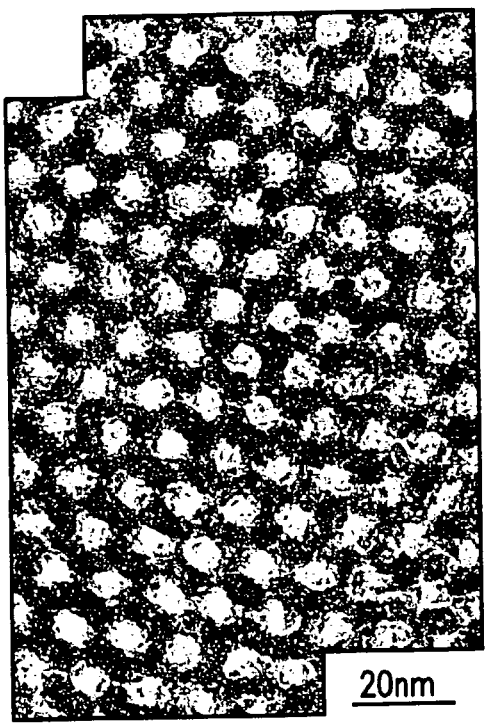
FIG. 5 shows transmission electron micrographs with different pore sizes and silica wall thicknesses for calcined hexagonal mesoporous silica SBA-15 prepared using the block copolymer $PEO_{20}PPO_{70}PEO_{20}$. (a) pore size of 47 Å, silica wall thickness of 60 Å; (b) pore size of 89 Å, silica wall thickness of 30 Å; (c) pore size of 200 Å; (d) pore size of 260 Å.
Figure 5B:
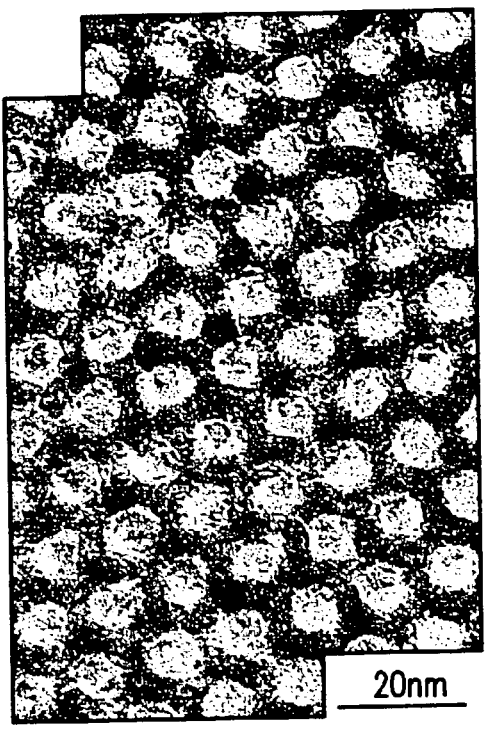

Heating as-synthesized SBA-15 in the reaction solution at different temperatures (80–140° C.) and for different lengths of time (11 72 h) resulted in a series of structures with different pore sizes (47–89 Å) and different silica wall thicknesses (31–64 Å) (as presented in Table 1). The pore sizes and the wall thicknesses determined for hexagonal SBA-15 from TEM images (such as shown in FIGS. 5a, 5b) are in agreement with those estimated from X-ray and $N_2$ adsorption measurements. The walls are substantially thicker than those typical for MCM-41 (commonly 10–15 Å) prepared using alkylammonium ion surfactant species as the structure directing-agents. Higher temperatures or longer reaction times result in larger pore sizes and thinner silica walls, which may be caused by the high degree of protonation of the long hydrophilic PEO blocks of the copolymer under the acidic $S^+X^-I^+$ synthesis conditions. EOH moieties are expected to interact strongly with the silica species and to be closely associated with the inorganic wall. Increasing the reaction temperature results in increased hydrophobicity of the PEO block group, and therefore on average smaller numbers of the EOH groups that are associated with the silica wall (see below) and thus increased pore sizes.

The pore size of hexagonal mesoporous SBA-1 5 can be increased to ~300 Å by the addition of cosolvent organic molecules such as 1,3,5-trimethylbenzene (TMB). In a typical preparation, 4.0 g of PLURONIC P123 was dissolved in 30 g water and 120 g (2 M) HCl solution with stirring at room temperature. After stirring to dissolve completely the polymer, 3.0 g TMB was added with stirring for 2 h at 35° C. 8.50 g TEOS was then added to the above homogeneous solution with stirring at 35° C. for 22 h. The mixture was then transferred to a Teflon autoclave and heated at 100–140° C. without stirring for 24 h. The solid product was subsequently filtered, washed, and air-dried at room temperature.

Figure 5C:
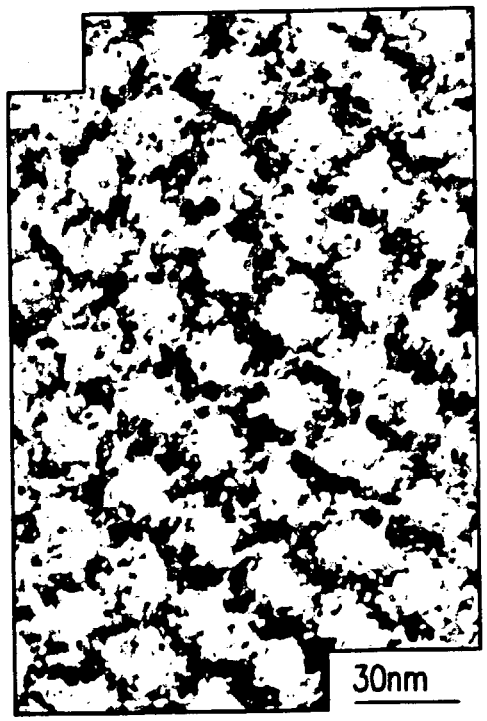
Figure 5D:
Figure 6:
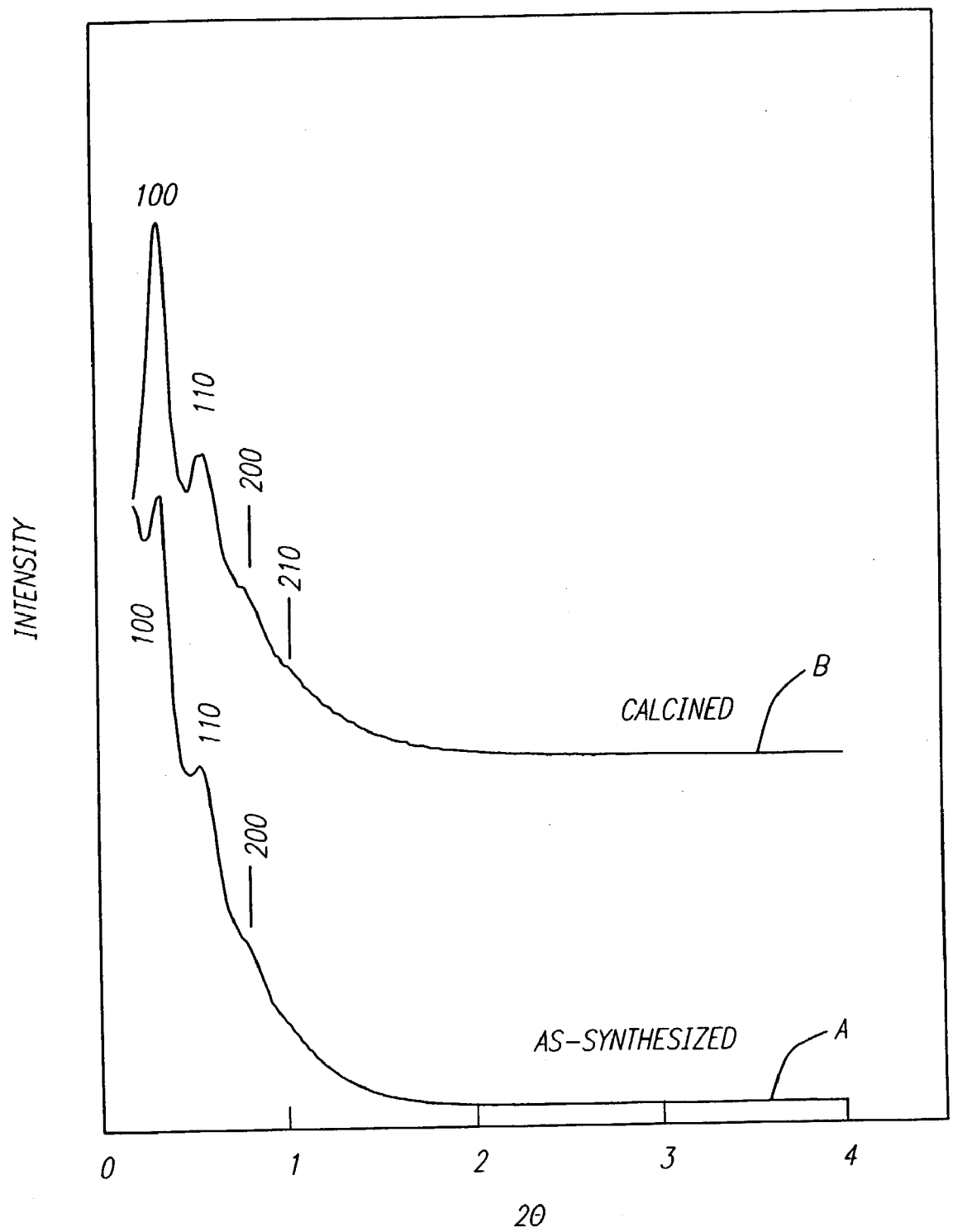
FIG. 6 shows powder X-ray diffraction (XRD) patterns of as-synthesized and calcined mesoporous silica SBA-15.

FIG. 6 shows the typical XRD patterns of hexagonal SBA-15 prepared by adding an organic swelling agent. The chemical composition of the reaction mixture was 4 g of the copolymer: 3 g TMB: 0.041 M TEOS: 0.24 M HCl: 6.67 M $H_2O$. The X-ray pattern of as-synthesized product (FIG. 6a) shows three well-resolved peaks with d spacings of 270, 154, and 133 Å at very low angle (2$\hat{}$ range of 0.2–1°), which are indexable as (100), (110), and (200) reflections associated with p6 mm hexagonal symmetry. The (210) reflection is too broad to be observed. The intense (100) peak reflects a d-spacing of 270 Å, corresponding to an unusually large unit cell parameter (a=310 Å). After calcination in air at 500° C. for 6 h, the XRD pattern (FIG. 6b) shows improved resolution and an additional broad (210) reflection with d spacing of 100 Å. These results indicate that hexagonal SBA-15 is thermally stable, despite its unusually large lattice parameter. The $N_2$ adsorption-desorption results show that the calcined product has a BET surface area of 910 $m^2/g$, a pore size of 260 Å, and a pore volume of 2.2 $cm^3/g$. TEM images confirm that the calcined products have highly ordered, hexagonal symmetry with unusually large pore sizes (FIGS. 5c, 5d).

Figure 7:
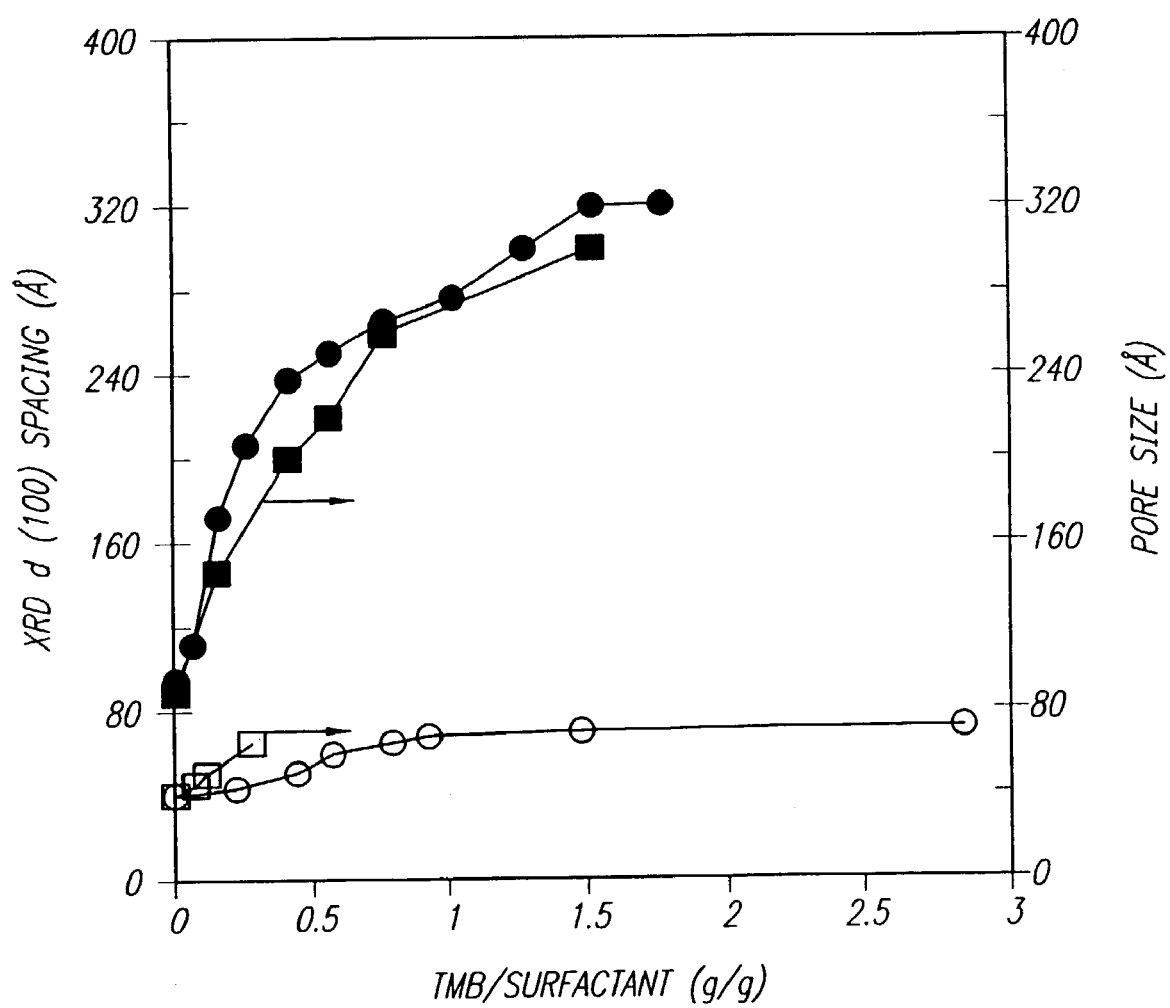
FIG. 7 shows variation of the d(100) spacing (solid) and pore size (open) for mesoporous hexagonal SBA-15 calcined at 500° C. for 6 h in air (circles) and for mesoporous MCM-41 (squares) as functions of the TMB/amphiphile (copolymer or surfactant) ratio (g/g).

FIG. 7 shows the change of the pore size and the d-spacing of the XRD d(100) peak as a function of the TMB/copolymer mass ratio for calcined hexagonal SBA-15. The pore sizes of calcined SBA-15 were measured from the adsorption branch of the $N_2$ adsorption-desorption isotherm curve by the BJH (Barrette-Joyner-Halenda) method using the Halsey equation for multilayer thickness. The pore size data for the MCM-41 sample were taken from ref. 4. The chemical compositions of the reaction mixture were 4 g of the copolymer: xg TMB: 0.041 M TEOS: 0.24 M HCl: 6.67 M $H_2O$ for SBA-15 and $NaAlO_2$: 5.3 $C_{16}$TMACl: 2.27 TMAOH: 15.9 $SiO_2$:xg TMB: $1450H_2O$ for the MCM-41 ($C_{16}$TMACl=cetyltrimethylammonium chloride, TMAOH=tetramethyl-ammonium hydroxide). The ratios used in this study ranged from 0 to 3, with the d(100) spacing and pore size increasing significantly, up to 320 Å and 300 Å, respectively, with increasing TMB/copolymer ratio. The increased pore size is accompanied by retention of the hexagonal mesostructure, with the X-ray diffraction patterns of each of these materials exhibiting 3–4 peaks.

To the best of our knowledge, hexagonal SBA-15 has the largest pore dimensions thus far demonstrated for mesoscopically ordered porous solids. As shown in FIG. 7, the d(100) spacing and pore size of calcined MCM-41 prepared by using cationic surfactant species can also be increased, but compared to SBA-15, the change is much less. In addition, although MCM-41 pore sizes of ca. 100 Å can be achieved by adding auxiliary organic species (e.g., TMB), the resulting materials have significantly reduced mesostructural order. The XRD diffraction patterns for such materials are substantially less resolved, and TEM micrographs reveal less ordering, indicating that the materials possess lower degrees of mesoscopic order. This is particularly the case near the high-end of this size range (~100 Å) for which a broad single peak is often observed. These materials also tend to suffer from poor thermal stability as well, unless additional treatment with wellTEOS (which reduces the pore size) is carried out. From our results, a family of highly ordered mesoporous SBA-15 silica can be synthesized with large uniform and controllable pore sizes (from 89–500 Å) by using PEO-PPO-PEO copolymer species as amphiphilic structure-directing agents, augmented by the use of organic swelling agents in the reaction mixture. The pore size for hexagonal SBA-15 determined by TEM images (FIGS. 5c, 5d) is in agreement with that established from separate $N_2$ adsorption measurements.

Figure 8:
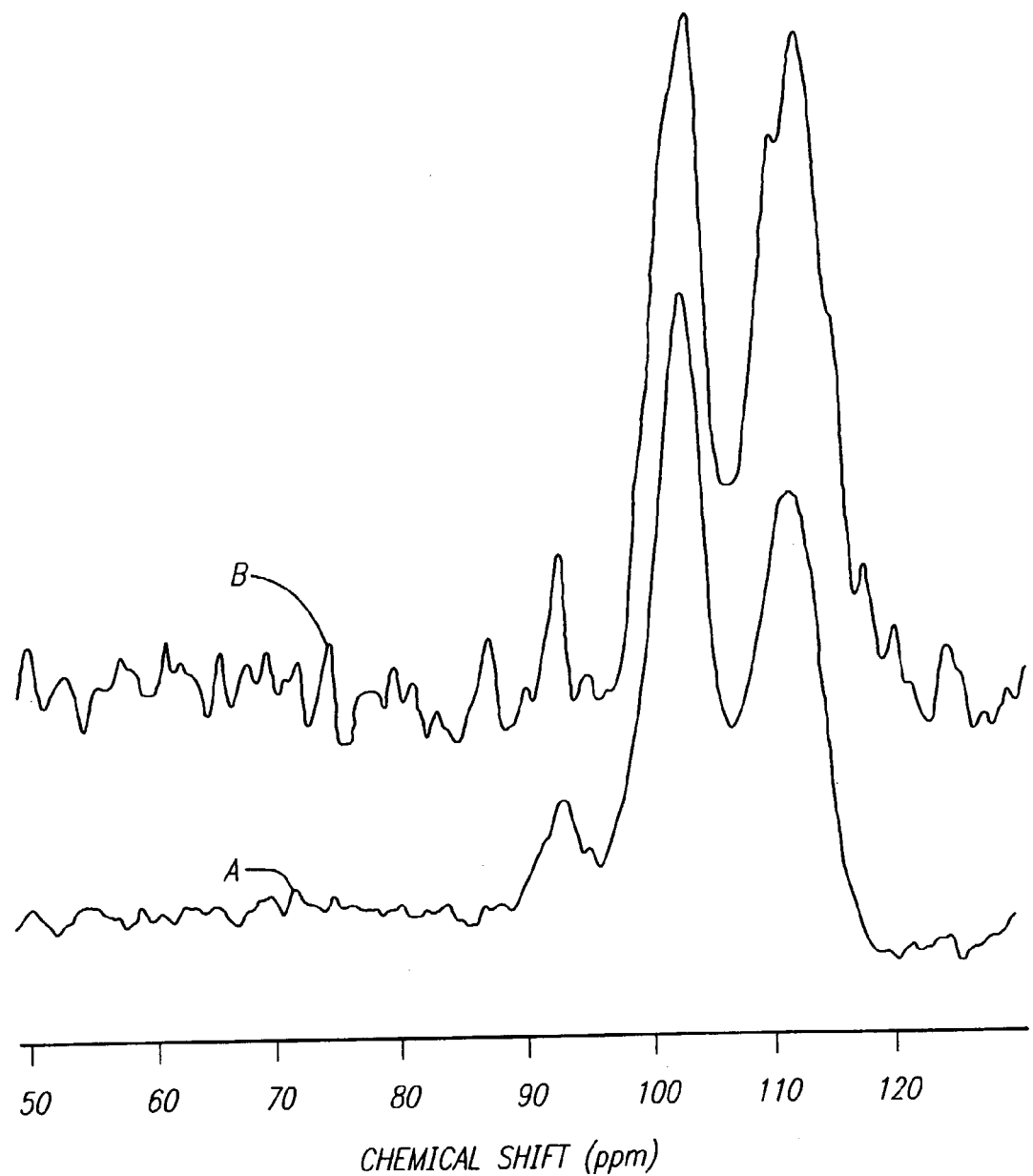
FIG. 8 shows $^{29}Si$ MAS NMR spectra of as-synthesized silica-copolymer mesophase materials; (a) SBA-11 prepared by using Brij $C_{16}EO_{10}$ surfactant; (b) SBA-15 prepared using $PEO_{20}PPO_{70}PEO_{20}$ block copolymer.

Magic-Angle Spinning $^{29}Si$ NMR spectra (FIG. 8) of as-synthesized hexagonal SBA-15 show three broad peaks at 92, 99, and 109 ppm, corresponding to $Q^2$, $Q^3$, and $Q^4$ silica species, respectively. From the relative peak areas, the ratios of these species are established to be $Q^2:Q^3:Q^4=0.07:0.78:1$. These results indicate that hexagonal SBA-15 possesses a somewhat less condensed, but similarly locally disordered, silica framework compared to MCM-41.

Figure 9:
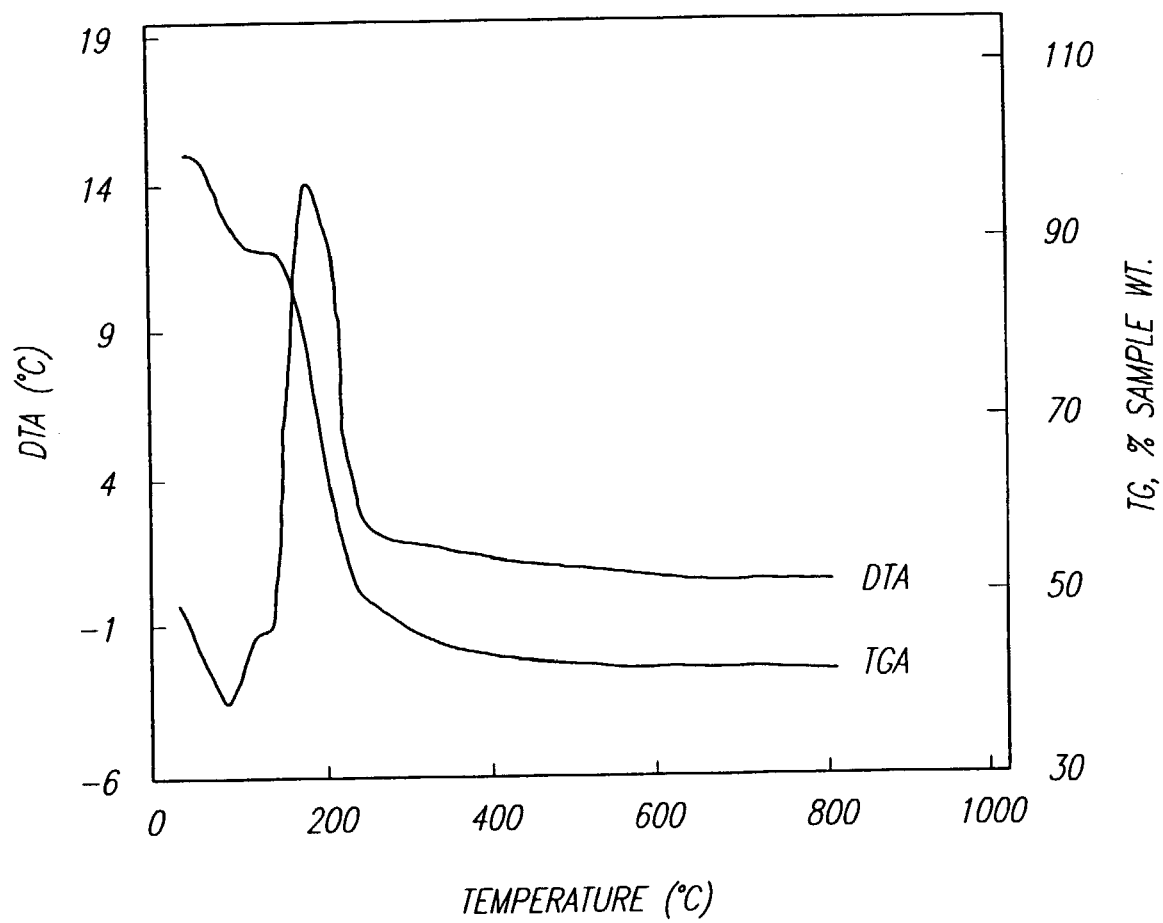
FIG. 9 shows thermogravimetric analysis (TGA) and differential thermal analysis (DTA) traces for the as-synthesized SBA-15 prepared by using the block copolymer $PEO_{20}PPO_{70}PEO_{20}$.

TGA and DTA analyses (FIG. 9) of hexagonal SBA-15 prepared using $PEO_{20}PPO_{70}PEO_{20}$ show total weight losses of 58 wt % apparently consisting of two apparent processes: one at 80° C. (measured using TGA) yields a 12 wt % loss, accompanied by an endothermic DTA peak due to desorption of water, followed by a second 46 wt % weight loss at 145° C. with an exothermic DTA peak due to desorption of the organic copolymer. A Netzsch Thermoanalyzer STA 409 was used for thermal analysis of the solid products, simultaneously performing TGA and DTA with heating rates of 5 $Kmin^{-1}$ in air.

The desorption temperature of the large block copolymer (~150° C.) is much lower than that of cationic surfactants (~360° C.), so that the organic copolymer species can be completely removed and collected without decomposition by heating SBA-15 in an oven (air) at 140° C. for 3 h. (The possibility to recover and reuse the relatively expensive triblock copolymer structure-directing species is an important economic consideration and benefit to these materials.) It should be noted that the pure block copolymer $PEO_{20}PPO_{70}PEO_{20}$ decomposes at 270 OC, which is substantially lower than that of cationic surfactants (~360° C.) during calcination. For comparison, the TGA of the copolymer $PEO_{20}PPO_{70}PEO_{20}$ impregnated in $SiO_2$ gel shows that the copolymer can be desorbed at 190° C., which is ~50° C. higher than required for hexagonal SBA-15. Removal of the organic species from as-synthesized SBA-15 at these relatively low temperatures (e.g., 140° C.) suggests the absence of strong electrostatic or covalent interactions between the copolymer species and the polymerized silica wall, together with facile mass transport through the pores. The possibility to recover and reuse the relatively expensive triblock copolymer structure-directing species is an important economic consideration and advantage of these materials.

Hexagonal SBA-15 can be synthesized over a range of copolymer concentrations from 2–6 wt % and temperatures from 35–80° C. Concentrations of the block copolymer higher than 6 wt % yielded only silica gel or no precipitation of silica, while lower copolymer concentrations produced only dense amorphous silica. At room temperature, only amorphous silica powder or products with poor mesoscopic order can be obtained, and higher temperatures (>80° C.) yield silica gel. Like TEOS, tetramethylorthosilicate (TMOS) and tetrapropoxysilane (TPOS) can also be used as the silica sources for the preparation of hexagonal SBA-15.

SBA-15 can be formed in acid media (pH<1) using HCl, HBr, HI, $HNO_3$, $H_2SO_4$, or $H_3PO_4$. Concentrations of HCl (pH 2–6) above the isoelectric point of silica (pH 2) produce no precipitation or yield unordered silica gel. In neutral solution (pH 7), only disordered or amorphous silica is obtained. We also measured the precipitation time (t) of the silica as a function of the concentration of HCl and $Cl^-$. The $[Cl^-]$ concentration was varied by adding extra NaCl, while keeping the $H^+$ concentration constant. From these measurements, log (t) is observed to increase linearly with log C (where C is the concentration of HCl or $Cl^-$). Slopes of 0.31 for $[Cl^+]$ and 0.62 for HCl indicate that $Cl^-$ influences the synthesis of SBA-15 to a lesser extent than does $H^+$. Based on these results, we propose that the structure-directed assembly of SBA-15 by the polyoxyalkylene block copolymer in acid media occurs by a $S^+X^-I^+$ pathway. While both the EO and PO groups of the copolymer are positively charged in acidic media, the PO groups are expected to display more hydrophobicity upon heating to 35–80° C., thereby increasing the tendency for mesoscopic ordering to occur. The protonated polyoxyalkylene ($S^+$), the anionic inorganic ($X^-$) bonding, $S^+X^-$, and the positive silica species ($I^+$) are cooperatively assembled by hydrogen bonding interaction forces. Assembly of the surfactant and inorganic species, followed by condensation of silica species, results in the formation of hexagonal SBA-15 mesophase silica. At high pH values (2–7), the absence of sufficiently strong electrostatic or hydrogen bonding interactions leads to the formation of amorphous or disordered silica.

Figure 10B:
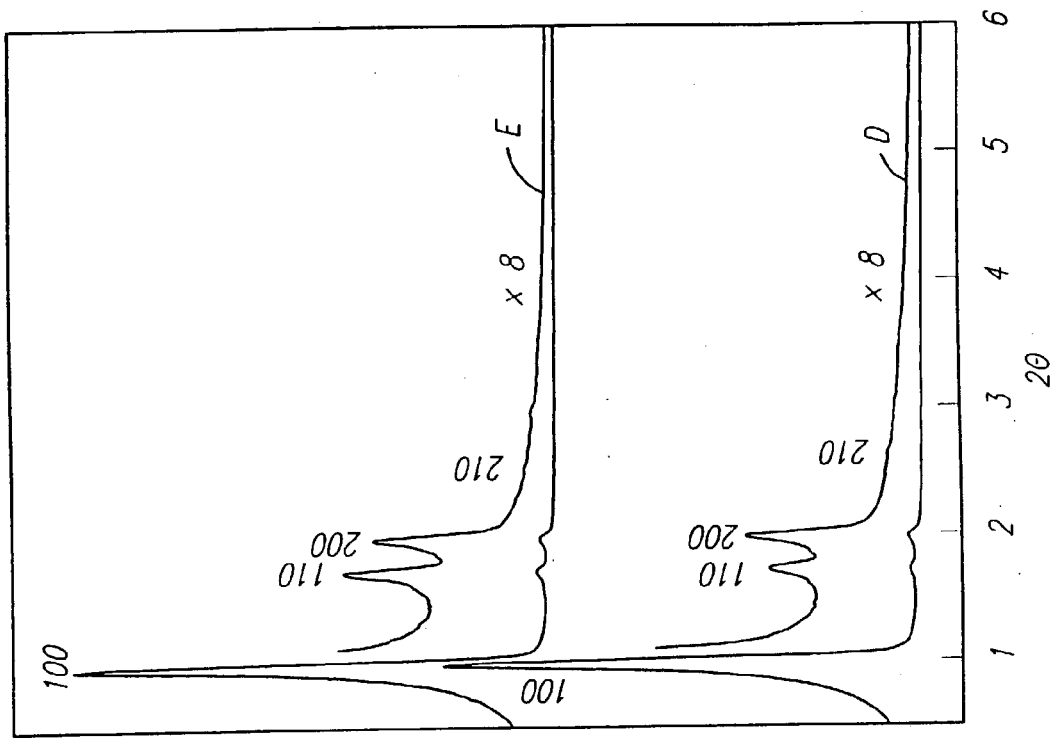
FIG. 10 shows powder X-ray diffraction (XRD) patterns of (a), as-synthesized and, (b) calcined MCM-41 silica prepared using the cationic surfactant $C_{16}H_{33}N(CH_3)_3Br$, and (c), calcined MCM-41 after heating in boiling water for 6 h; Calcined SBA-15 (d, e) prepared by using the block copolymer $PEO_{20}PPO_{70}PEO_{20}$ after heating in boiling water for (d), 6 h; (e), 24 h.
Figure 10A:
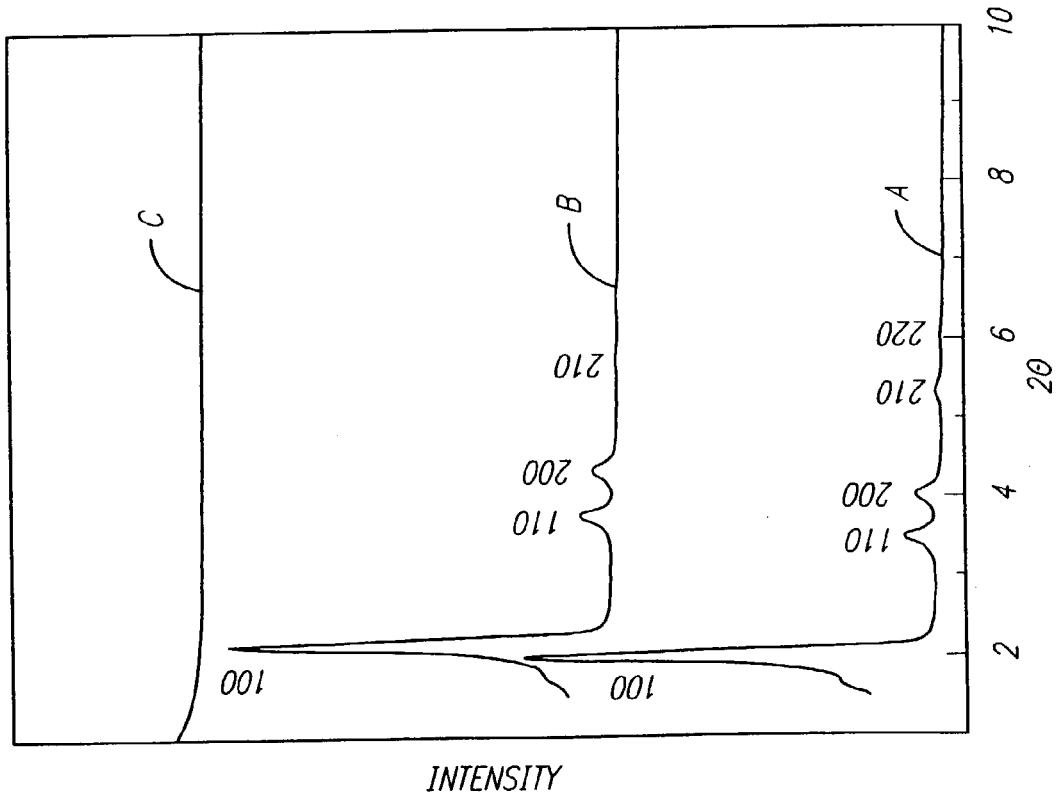

One of the limitations of calcined MCM-41 materials prepared without additional treatment with TEOS is their poor hydrothermal stability. As shown in FIG. 10, both as-synthesized and calcined (500° C. for 6 h) MCM-41, prepared with $C_{18}H_{33}N(CH_3)_3Br$ as previously described, show well resolved hexagonal XRD patterns (FIGS. 10a, 10b). However, after heating in boiling water for 6 h, the structure of calcined MCM-41 is destroyed and the material becomes amorphous, as evidenced by the absence of XRD scattering reflections in FIG. 10c. By contrast, all of the calcined hexagonal SBA-15 samples prepared using the PEO-PPO-PEO block copolymers are stable after heating in boiling water for 24 h under otherwise identical conditions. For calcined hexagonal SBA-15 prepared by using the $PEO_{20}PPO_{70}PEO_{20}$ copolymer and after calcination in air at 500° C. and subsequent heating in boiling water for 6 h, the (210) reflection becomes broader, the (300), (220), and (310) peaks become weaker, while the (100) peak is still observed with similar intensity (FIG. 10d). After heating in boiling water for 24 h, the intensity of the (100) Bragg peak (FIG. 10e) is still unchanged. Nitrogen BET adsorption isotherm measurements carried out after such hydrothermal treatment shows that the monodispersity of the pore size, surface area, and pore volume are retained. The results confirm that calcined hexagonal SBA-15 silica is significantly more hydrothermally stable than calcined hexagonal MCM-41 silica, most likely because SBA-15 has a thicker silica wall. This is an improved one-step alternative to two-step post-synthesis treatments that use tetraethylorthosilicate (TEOS) to stabilize mesoporous MCM-41 by reforming and structuring the inorganic wall with additional silica.

Preparation of Mesoscopically Ordered Silica-copolymer Monoliths and Films.

Figures 11A, 11B:
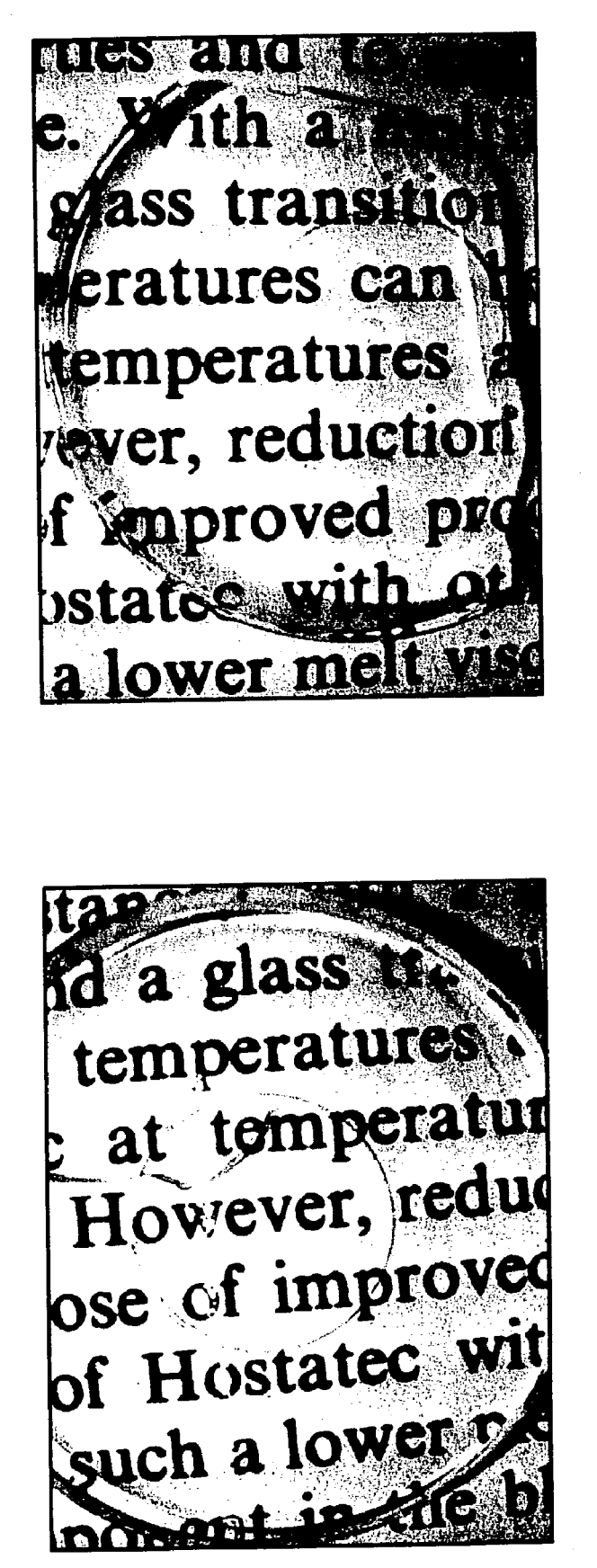

A typical preparation of monolithic silica-copolymer mesostructures is outlined below. All monolith block copolymer weight percents are calculated with respect to initial TEOS added, e.g. wt %=[mass F127/(mass F127+mass TEOS)]×100. A series of samples was made with varying amounts of PLURONIC F127 $PEO_{100}PPO_{65}PEO_{100}$ triblock copolymer, while holding other processing conditions constant. A calculated amount of a 20 wt % PLURONIC F127/EtOH solution (between 0.7 and 3.5 ml) is transferred into a 30 ml vial. 0.72 ml of an acidic solution of HCl (pH 1.5) is added to the polymer solution while stirring, followed by addition of 1.0 ml of tetraethylorthosilicate (TEOS). The solution is stirred until homogeneous, and allowed to gel uncovered under ambient conditions. After gelation (~2 days) the samples are covered for 2 weeks at room temperature. At the end of this period the gels have shrunk, yet done so uniformly to retain the shape of the container. Further research has shown that addition of a small amount of 3-glycidoxypropyltrimethoxysilane can prevent shrinkage. The cover is removed and the materials are dried at room temperature to eliminate excess solvent. The F127 series materials produced are transparent up to 38 wt % polymer, after which the polymer macro-phase separates creating a white opaque material. FIGS. 11a and 11b show optical photographs of two of the monoliths produced. These monoliths were produced using a 2:1 ratio of water to TEOS at pH 1.4 and room temperature, with aging for approximately 1 month. Note the high degree of transparency and only one crack in the 34 wt % sample. Subsequent research has allowed us to produce crack-free monoliths by varying the aging time and temperature. The monoliths pictured are approximately 3-mm thick; although thicker monoliths can be produced, the aging time for these samples increases significantly to eliminate cracking.

These monoliths were analyzed using XRD, TEM, and NIVIR to determine mesostructural morphology, as well as the mechanism of the structure formation. The F127 polymer series above showed an aggregation point of roughly 25 wt % F127, below which the polymer was disordered and homogeneously dispersed within the matrix and above which aggregation of the polymers led to silica-copolymer mesophases. The copolymer weight percents required to produce specific phases vary depending upon the exact conditions and copolymer used, however this example may be considered representative, though by no means all inclusive, of the results observed.

Figure 12:
FIG. 12 shows a 200-keV TEM image of a 38 wt % SBA-15 silica-copolymer monolith prepared with PLURONIC F127.

XRD patterns of powdered samples obtained from the monoliths show a single diffraction peak with increasing intensity for increasing polymer concentration with a maximum at 38 wt %. Below 27 wt % F127, no XRD intensity is observed. The d(100) peak is centered at 112 Å for 27–34 wt % and increases to 120 Å for the 38 wt % sample. The change in the location of the peak is due to phase changes in the material, as observed by TEM and NMR. TEM reveals well ordered silica-copolymer mesophases in the samples with higher copolymer concentration, such as the lamellar phase in the 38 wt % sample shown in FIG. 12. The image shows that the material has an extremely well ordered lamellar mesoscopic structure with a repeat distance of ~105 nm. The image region is 990×1200 nm. The large background stripes are artifacts produced by the microtome cutting process and are otherwise unrelated to the morphology of the material. Lower concentrations of copolymer produced hexagonal, gyroid, or micellar phases with spacings of about 110 Å. The domain sizes for these structures is quite large, well over 1 μm² for the lamellar phase, which makes it surprising that only one XRD peak is observed, although others have shown that single XRD patterns do not always imply poorly ordered materials (F. Schüth). Below 27 wt % no mesostructural ordering is observed.

NMR spectroscopy was utilized to provide information about copolymer-silicate interactions on the molecular level. $^1H$ $T_{1p}$ relaxation and two-dimensional $^{29}Si$—$^1H$ and $^{13}C$—$^1H$ heteronuclear correlation NMR experiments reveal that the polymer is rigidly incorporated in the silicate at 11 wt % and begins to microphase separate at 20 wt %. At 27 wt % the PEO and PPO are 80% separated from the silicate, and at 38 wt % the PPO is fully separated (>10 Å) from the matrix. This indicates that a phase change has occurred in progressing from copolymer concentrations of 27 to 34 wt % in the samples, where some PPO-$^{29}Si$ correlation intensity is still observed. Some PEO was observed to be associated with the matrix at all concentrations, implying that the polymerizing silica and PEO blocks are compatible. This suggests that the material is produced by polymerization of silicate oligomers that selectively swell the PEO block of the composite mesostructure.

Figure 13A:
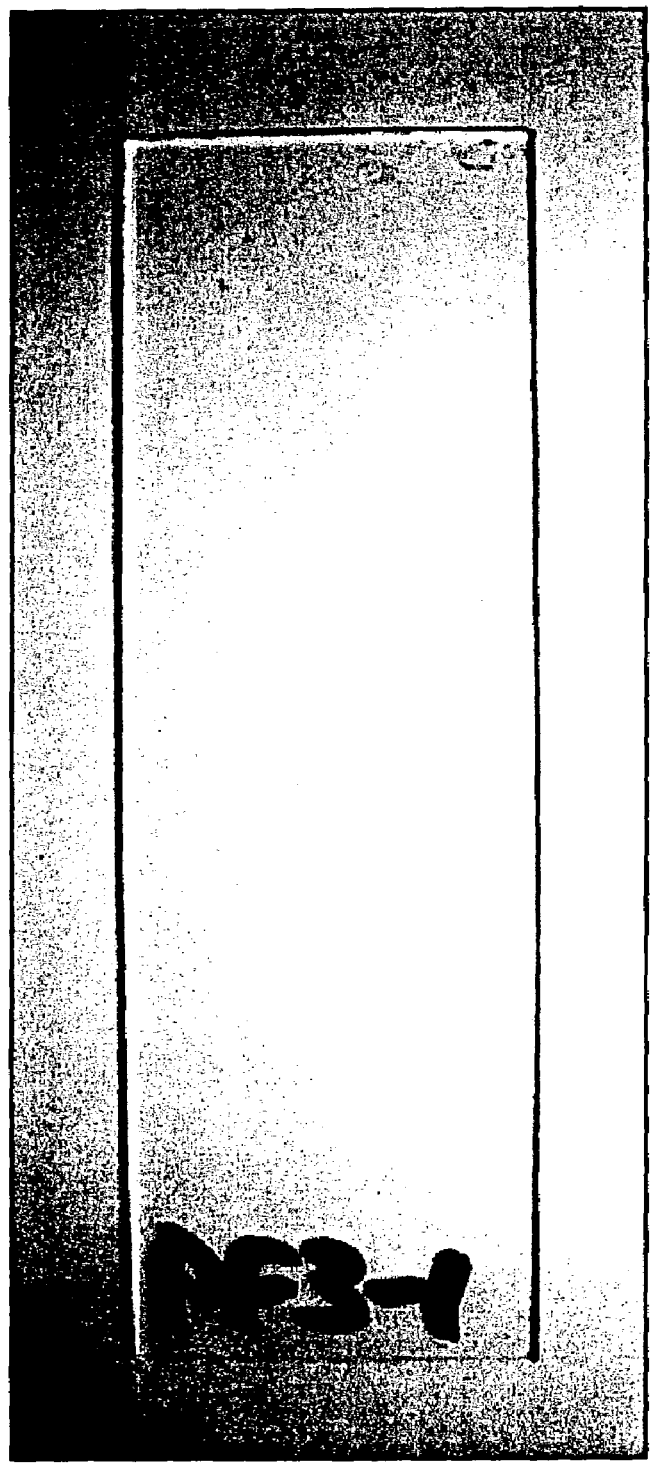
FIG. 13 shows (a) a photograph of a transparent 50-μm-thick SBA-15 silicacopolymer film prepared with PLURONIC P104. (b) an X-ray diffraction pattern of this film showing well resolved peaks that are indexable as (100), (110), (200), and (210) reflections associated with p6 mm hexagonal symmetry in which the one-dimensional axes of the aggregates lie horizontally in the plane of the film.
Figure 13B:
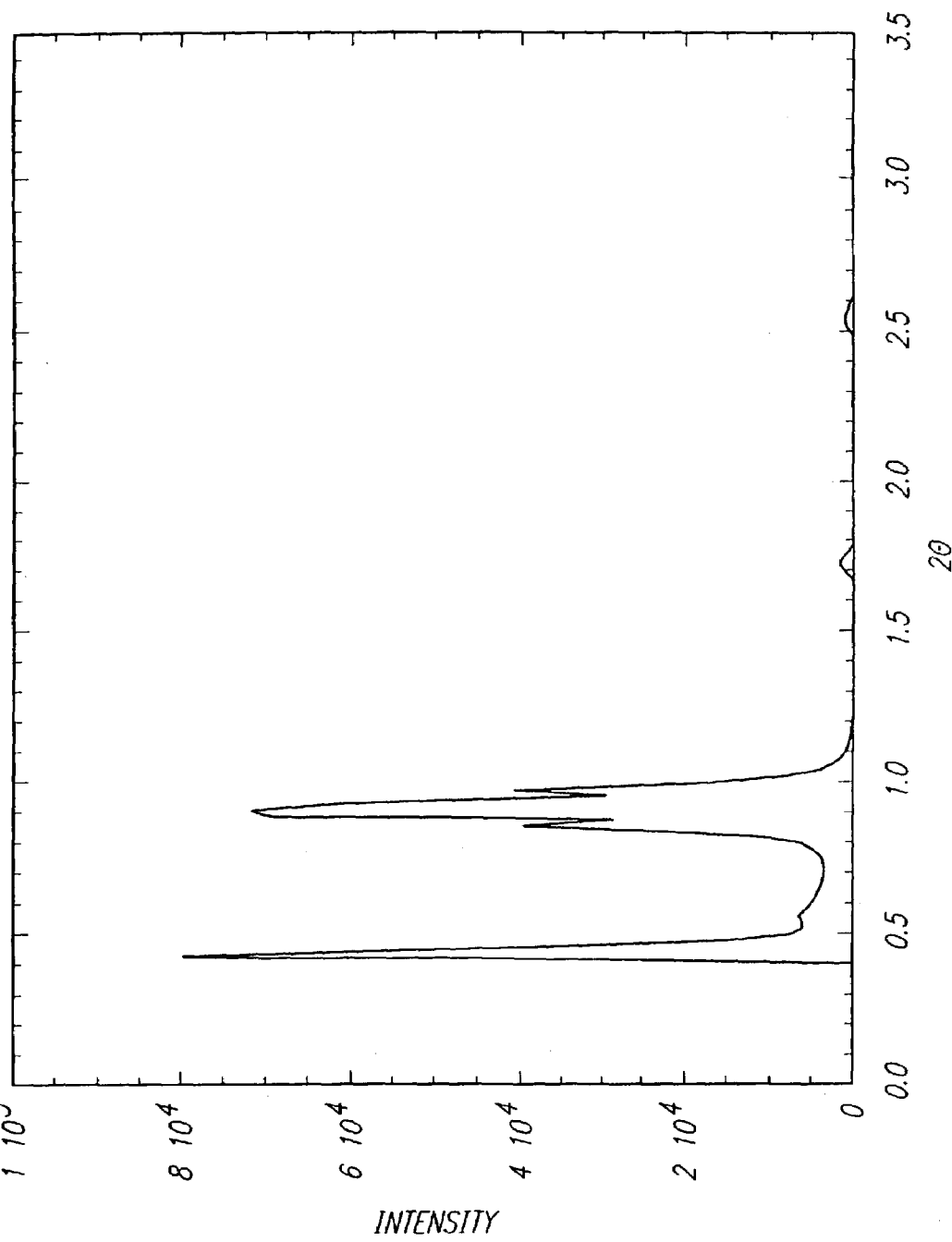

It is possible to use this chemistry and processing to produce thin SBA-15 silica-copolymer films by either spin-, drop-, or dip-casting. Such films can serve as robust permeable coatings for use in separation or chemical sensing applications or as host matrices for optically or electrically active guest molecules for use in optoelectronic devices. FIG. 13 shows a photograph and X-ray diffraction pattern of an optically transparent hexagonal SBA-15-copolymer film formed by drop-casting the reaction solution (2 ml TEOS, 0.6 ml $H_2O$, 0.80 g PLURONIC P104, 1 ml dimethylformamide) onto a glass slide and drying at room temperature. The film is 50-μm thick, crack-free and transparent. The X-ray diffraction pattern of this film shows well resolved peaks that are indexable as (100), (110), (200), and (210) reflections associated with p6 mm hexagonal symmetry in which the one-dimensional axes of the ca. 200 Å aggregates are highly ordered horizontally in the plane of the film.

High quality films can be produced generally as follows. A mixture of 5 ml tetraethylorthosilicate and 0.75–3.0 ml H20 (pH=1.4) is stirred for approximately 30 min or until the silicate has hydrolyzed sufficiently to become miscible with water and thereby form a homogeneous solution. An appropriate amount (generally between 10–40 wt %) of block copolymer, such as PLURONIC P104 polyethyleneoxide-polypropyleneoxide-poly-ethyleneoxide copolymer, is dissolved in the solution. An additive such as ethanol, dimethylformamide, or tetrahydrofuran can be added to vary the viscosity and coating properties. The mixture is allowed to age, then is dip-, drop-, or spin-coated onto a glass or Si wafer substrate. Thin films with variable thicknesses can also be produced using spin coating.

The XRD patterns confirm that these thin films have highly ordered hexagonal (p6 mm), cubic (1 m3 m), or 3-d hexagonal (p6₃/mmc) mesostructures. They are highly ordered and can easily be shear aligned. BET measurements show that the thin films have narrow pore size distributions, pore sizes of 20–120 Å, pore volumes up to 1.7 cm³/g and BET surface areas up to ~1500 m²/g. SEM images of these thin films show a uniformly flat surface. The thickness of the films can be adjusted from 100 nm–1 mm by varying the concentration of the solution, aging time and coating time.

The examples shown above use $PEO_{20}PPO_{70}PEO_{20}$ triblocck copolymer species as the structure-directing agents. Highly ordered, ultralarge mesopore size SBA-15 materials can also be synthesized by using PEO-PPO-PEO block copolymers with different ratios of EO to PO and without adding supplemental organic swelling agents, such as TMB. Table 1 summarizes the physicochemical properties of mesoporous silica prepared by using triblock and reverse triblock copolymers. The d(100)-spacings from X-ray diffraction measurements can be in the range of 74.5–118 Å, with pore sizes of 46–100 Å established by $N_2$ adsorption measurements. The BO/PO ratio and intramolecular distribution and sizes of the corresponding blocks affect the formation of SBA-15. A lower EO/PO ratio with a symmetric triblock PEO-PPO-PEO copolymer architecture favors the formation of p6 mm hexagonal SBA-15. For example, PLURONIC L121, $PEO_5PPO_{70}PEO_5$, at low concentrations (0.5–1 wt %) forms hexagonal SBA-15, while use of higher concentrations of this copolymer (2–5 wt %) leads to an unstable lamellar mesostructured silica phase. Higher EO/PO ratios of the block copolymer, e.g. $PEO_{100}PPO_{39}PEO_{100}$ or $PEO_{80}PPO_{30}PEO_{80}$, yield cubic SBA-15 silica, including an Im3 m morphology. These cubic mesophase materials yield large 54–80 Å mesoscopically ordered pores and high BET surface areas (up to 1000 m²/g). Hexagonal mesoporous silica SBA-15 can also be synthesized by using reverse PPO-PEO-PPO triblock copolymer configuration, for example, $PPO_{19}PEO_{33}PPO_{19}$.

In general, any microphase-separating, domain-partitioning copolymer architecture can be considered promising for the synthesis of such mesostructured materials, according to the specifications imposed by processing conditions and utimately the product properties desired. Additionally, cubic (Pm3 m) and hexagonal (p6 mm) mesostructures can be formed by using Brij 56, $C_{16}H_{33}(OCH_2CH_2)_{10}OH$ ($C_{16}EO_{10}$) surfactant species, with the pore sizes controllable from 25–40 Å and BET surface areas up to 1070 m²/g. Brij 76 ($C_{18}EO_{10}$) yields the three-dimensional hexagonal (P6₃/mmc) and two-dimensional hexagonal (p6 mm) mesostructures with similar pore sizes and surface areas; see Table 2.

Films and monoliths can be produced with several variations of the solution conditions and/or sol-gel parameters, such as the ratio of water to TEOS, aging time, acidity, additives, temperature, and choices of copolymer or nonionic surfactants. Materials for specific applications can be formulated by appropriate modification of these parameters. Heat treatment after gelation can also produce harder materials that are less likely to crack.

We have found that silica-surfactant mesophases and MCM-41-type mesoporous materials can be aligned using liquid crystal processing strategies, including imposition of magnetic, shear, or electric fields. Similarly, polymer processing of the silica-copolymer composites is expected to be equally advantageous for producing aligned ultra large mesopore hydrothermally spH materials. For example, it should be possible to induce orientational ordering of the silica-copolymer composites and resultant mesoporous materials by applying shear to the sol-gel/copolymer system as it dries. Concerning variations on processing SBA-15- copolymer thin films (0.1–100 μm), use of shear alignment strategies, including spin-casting and dip-casting (i.e., drawing a vertical coverslip from a reservoir of the reaction solution), have been shown to induce larger degrees of orientational order than provided by drop-cast preparations. Moreover, guest molecules such as conducting or optically active organic species can be introduced to the reaction solution(s) and incorporated into the silica-copolymer monoliths, films or powders prior to or during processing. We have demonstrated the efficacy of this for the inclusion of conducting polymer moieties, such as poly(3,4-ethylenedioxythiophene) in SBA-15 silica-copolymer monoliths and spin-, drop-, and dip-cast films.

Methods currently available for the preparation of inorganic-organic mesophases or mesoscopically ordered porous materials typically involve one of five pathways that rely on Coulombic or hydrogen-bonding interactions, represented by the shorthand notations $S^+I^-$, $S^+X^-I^+$, $S^-I^+$, $S^-X^+I^-$, or $S^0I^0$. The most popular route used in syntheses of mesoporous materials has been the $S^+I^-$ approach in basic media, but the $S^-I^+$ and $S^-X^+I^-$ syntheses generally yield unstable non-silica based mesoporous materials. Furthermore, the surfactants used as the structure-directing agents in these cases (e.g., alkylammonium, alkylamine) are expensive and/or environmentally noxious. The $S^0I^0$ synthesis route generally yields disordered or worm-like mesoporous solids due to the absence of strong electrostatic or hydrogen bonding interactions. The materials and synthesis method described here are less expensive, non-toxic, and considerably more versatile than the cases described above. They can be used to tune material properties, such as mesoscopic ordering, pore size, hydrothermal stability, monolith shape, orientational alignment, and compatibility with a wide range of guest molecules to a significantly greater extent than possible with the current state-of-the-art.

The ultra large mesopores in calcined SBA-15 materials provide new opportunities in chromatographic separations of large molecules, such as proteins, enzymes, or polymers. In addition, these materials have promise for new applications in environmental remediation, such as the clean up of polycyclic aromatics, porphyrins, other large organics, and heavy metals from process streams or soils. These properties can be enhanced and tailored by functionalizing molecular moieties along the inorganic walls to provide chemical as well as size selective specificity of adsorption interactions.

Figure 14:
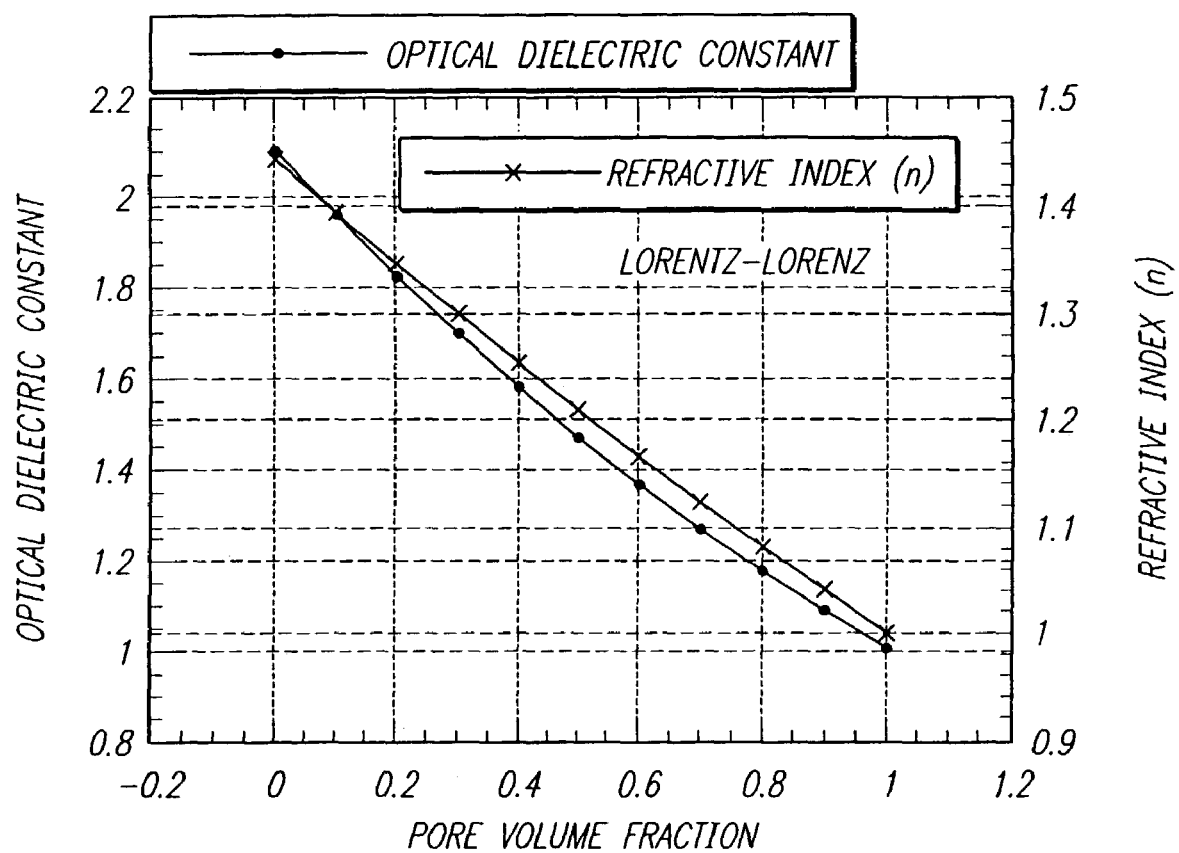
FIG. 14 shows the predicted variation of optical dielectric constant and refractive index as a function of silica porosity.

To the best of our knowledge there have been no reports of mesoscopically ordered silica monoliths or films with large characteristic structural length scales (>50 Å). The large dimensions of the inorganic-copolymer aggregates and large pore sizes of the composite or mesoporous materials detailed herein are superior to conventional mesoporous solids due to their thermal stability, transparency, monolithic form, and ability to incorporate large guest molecules. SBA-15 mesoporous silica also has distinct advantages over dense silica, particularly for applications requiring a lower dielectric constant material. SBA-15 has much lower density, long range mesoscopic order and possibilities for obtaining materials with high degrees of structural anisotropy, compared to dense silica. The improvements substantially exceed those provided by MCM-type materials, as discussed earlier. This has attractive implications for the development of low dielectric constant materials, particularly for reducing the capacitance of interconnects, which are among the most severely limiting factors in improving integrated and optical circuit performance. As shown in FIG. 14, the quest for materials with dielectric constants significantly below 2 appears to be well within reach; calcined SBA-15 materials have been prepared with porosities of 0.6–0.86, which lead to calculated optical dielectric constants of 1.1–1.4. One can produce aligned morphologies or structures with unconnected spherical cavities to eliminate transverse channel connectivities, which are undesirable for dielectric materials applications.

Use of block copolymers with a hydrophobic core also produces the unique ability to stabilize hydrophobic guest molecules that would not otherwise be compatible with the hydrophilic sol-gel reaction, such as some optically active dyes and polymers. Before now all optical moieties incorporated into sol-gel materials were either water soluble or had to be chemically grafted onto a compatible polymer. The inclusion of a hydrophobic region within our silicates, yet still smaller then optical wavelengths, allows an entirely new area of monoliths and coatings to be developed using hydrophobic dyes and optically active organics while retaining optical transparency. Furthermore, inclusion of guest conducting or optically active species, such as polymers and/or metal nanoparticles, in the pores can create quantum-effect materials. The controllability of the SBA-15 pore sizes, inorganic wall composition, organic composition, and guest species composition permit the properties (e.g., optoelectronic, mechanical, thermal, etc.) to be tuned over an enormous range. Indeed, sequential introduction of guest species, for example a conducting polymer coating on the interior of the inorganic wall, followed by a second polymer or metal/semiconductor species in the pore center, could lead to the first mesoscopically ordered arrays of nanosized coaxial quantum wires.

Generalized Block Copolymer Syntheses of Mesoporous Metal Oxides

Mesoporous metal oxides were synthesized at 30–70° C. using poly(alkylene oxide) block copolymers $HO(CH_2CH_2O)_x(CH_2CH(CH_3)O)_y(CH_2CH_2O)_xH$ ($EO_x$-$PO_y$-$EO_x$) or $HO(CH_2CH_2O)_x(CH_2CH(CH_3CH_2)O)_yH$ ($EO_x$-$BO_y$) block copolymers as the structure-directing agents. In a typical synthesis, 1 g of poly(alkylene oxide) block copolymer was dissolved in 10 g of ethanol (EtOH). To this solution, 0.01 mole of the inorganic chloride precursor was added with vigorous stirring. The resulting sol solution was gelled in an open petri dish at 40–60° C. in air. The aging time differs for different inorganic systems. Alternatively, the sol solution can be used to prepare thin films by dip coating. The as-made bulk samples or thin films were then calcined at 400° C. for 5 hours to remove the block copolymer surfactants. For the Al and $Si_{1-x}Al_x$ systems, calcination was carried out at 600° C. for 4 hr. For $WO_3$, calcination at 300° C. is sufficient to yield ordered mesoporous oxides.

X-ray diffraction (XRD) is an important technique for characterizing these metal oxide mesostructures. Table 3 summarizes the synthetic conditions, including the inorganic precursors and aging temperatures and times for the mesostructured inorganic/copolymer composites (before calcination) using $EO_{20}PO_{70}EO_{20}$ as the structure-directing agent. A broad array of mesostructured composites have been successfully prepared, covering the first-, second- and third-row transition metals and some main group elements as well. The ordering lengths shown in Table 3 correspond to the largest d value observed from the low-angle XRD patterns; it ranges from 70 to 160 Å for the different systems. High-order low-angle diffractions are also observed for most of these systems. Quantitative elemental chemical analysis suggests that the frameworks of these mesostructured composites are made up of metal-oxygen-chlorine networks.

Upon calcination, mesoporous $TiO_2$, $ZrO_2$, $Nb_2O_5$, $Ta_2O_5$, $Al_2O_3$, $WO_3$, $SiO_2$, $SnO_2$, $HfO_2$, and mixed oxides $Si_{1-x}Ti_xO_y$, $Zr_{1-x}Ti_xO_y$, $Al_{1-x}Ti_xO_y$, $Si_{1-x}Al_xO_y$ are obtained. X-ray diffraction, transmission and scanning electron microscopy imaging (TEM & SEM), and nitrogen adsorption/desorption are three crucial techniques for characterization of these materials. Table 4 summaries the analysis results, including the ordering length, pore size, wall thickness, wall structure, porosity and Brunauer-Emmet-Teller (BET) surface area.

Figure 15:
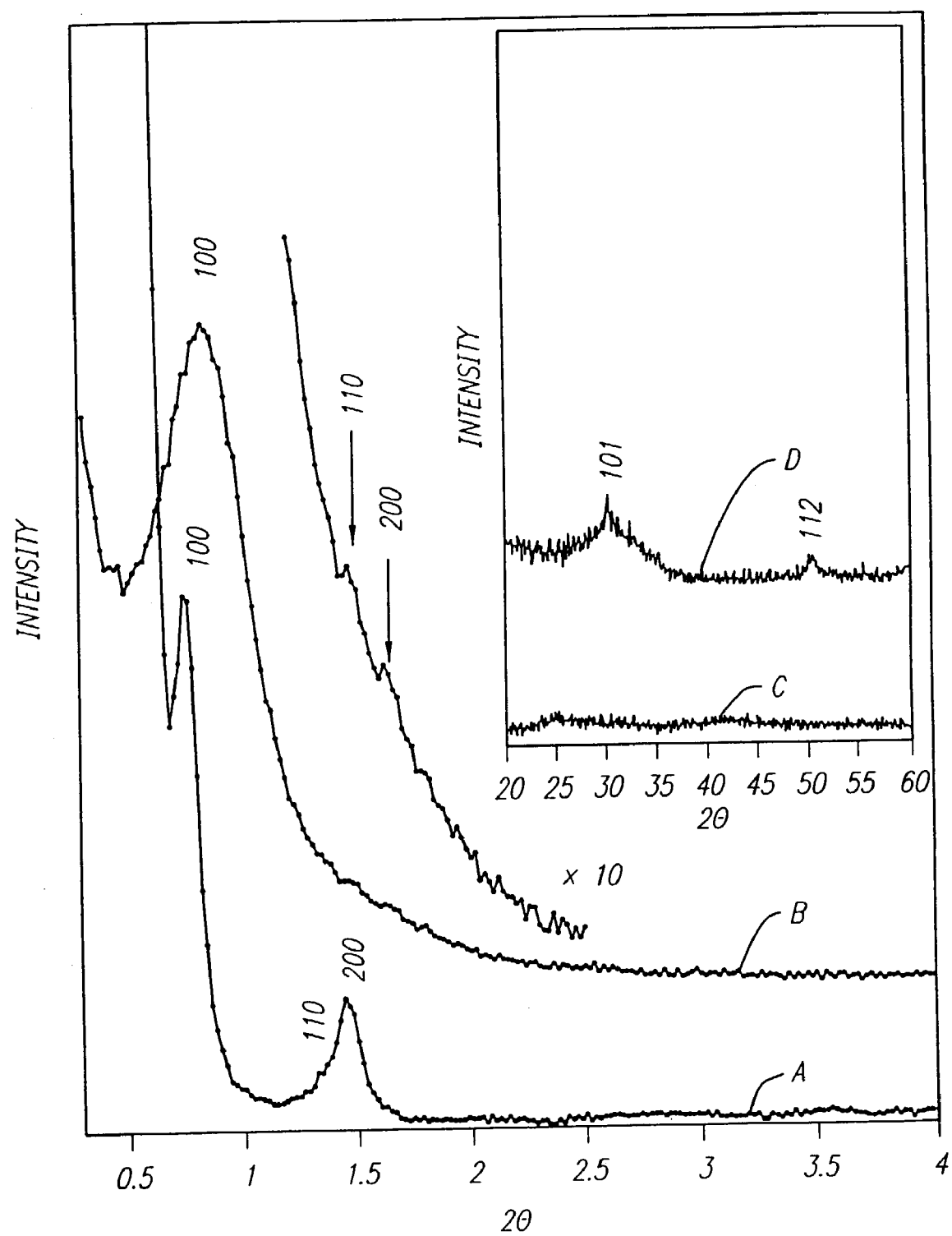
FIG. 15 shows low-angle and wide-angle X-ray diffraction (XRD) patterns of (a, c), as-made zirconium/$EO_{20}PO_{70}EO_{20}$ composite mesostructure and (b, d) calcined mesoporous $ZrO_2$. The XRD patterns were obtained with a Scintag PADX diffractometer using Cu Kα radiation.
Figure 16A:
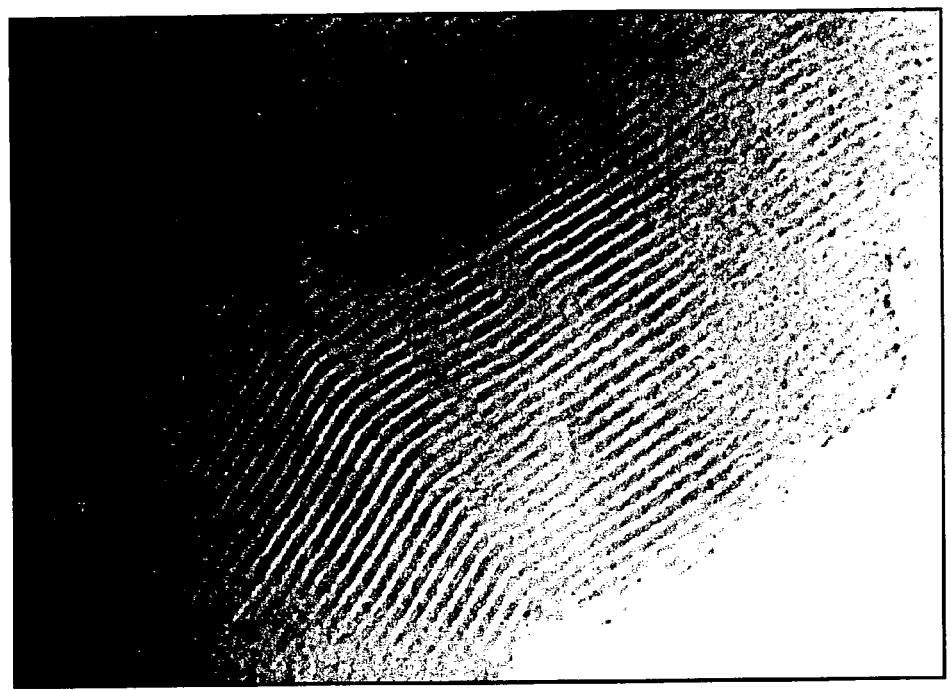
FIG. 16 shows TEM micrographs of 2-dimensional hexagonal mesoporous $ZrO_2$. (a) and (b) are recorded along the [110] and [001] zone axes, respectively. Inset in (b) is the selected-area electron diffraction pattern obtained on the image area. The images were recorded with a 200 kV JEOL transmission electron microscope. All samples were calcined at 400° C. for 5 hr to remove the block copolymer surfactant species.
Figure 16B:
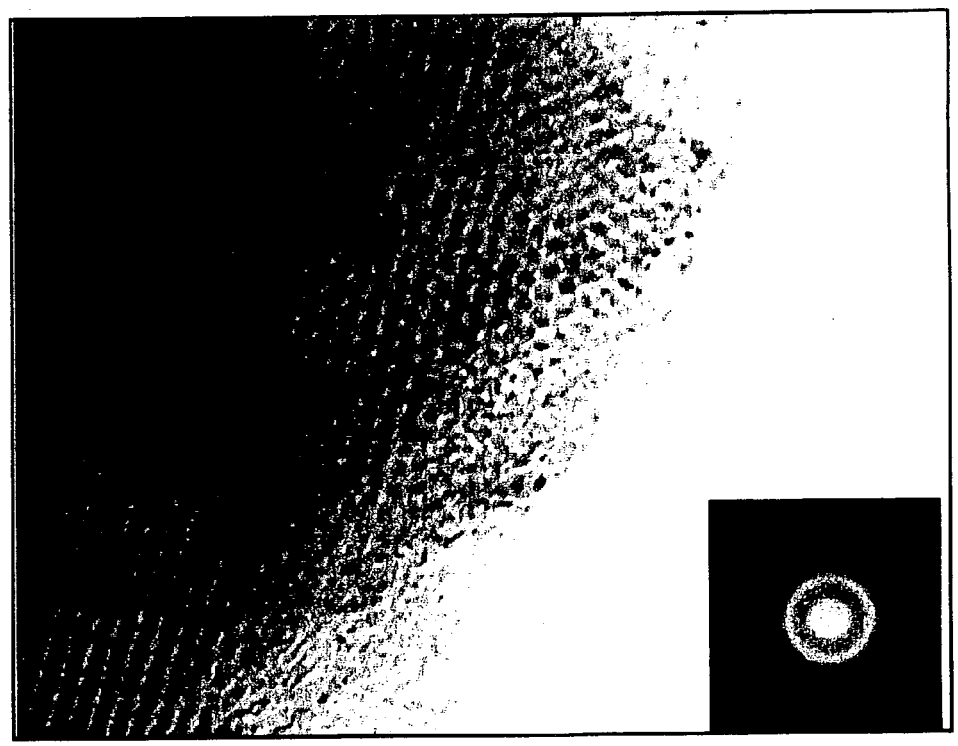
Figure 18A:
FIG. 18 shows TEM micrographs of 2-dimensional hexagonal mesoporous $SnO_2$. (a) and (b) are recorded along the [110] and [001] zone axes, respectively. Inset in (a) is selected-area electron diffraction pattern obtained on the image area.
Figure 18B:
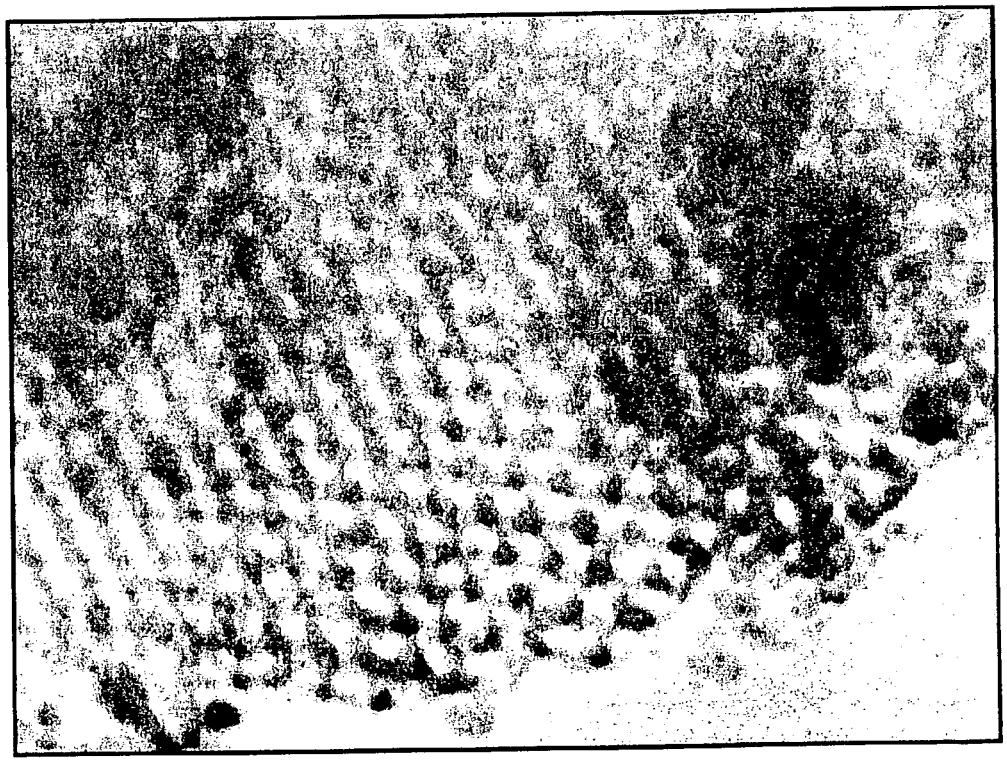
Figure 21:
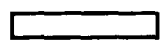
FIG. 21 shows TEM micrographs of 2-dimensional hexagonal mesoporous $Ta_2O_5$ recorded along the [001] zone axis.
Figure 26:
FIG. 26 shows TEM micrograph of 2-dimensional hexagonal mesoporous $ZrTiO_4$ recorded along the [001] zone axes.
Figure 29:
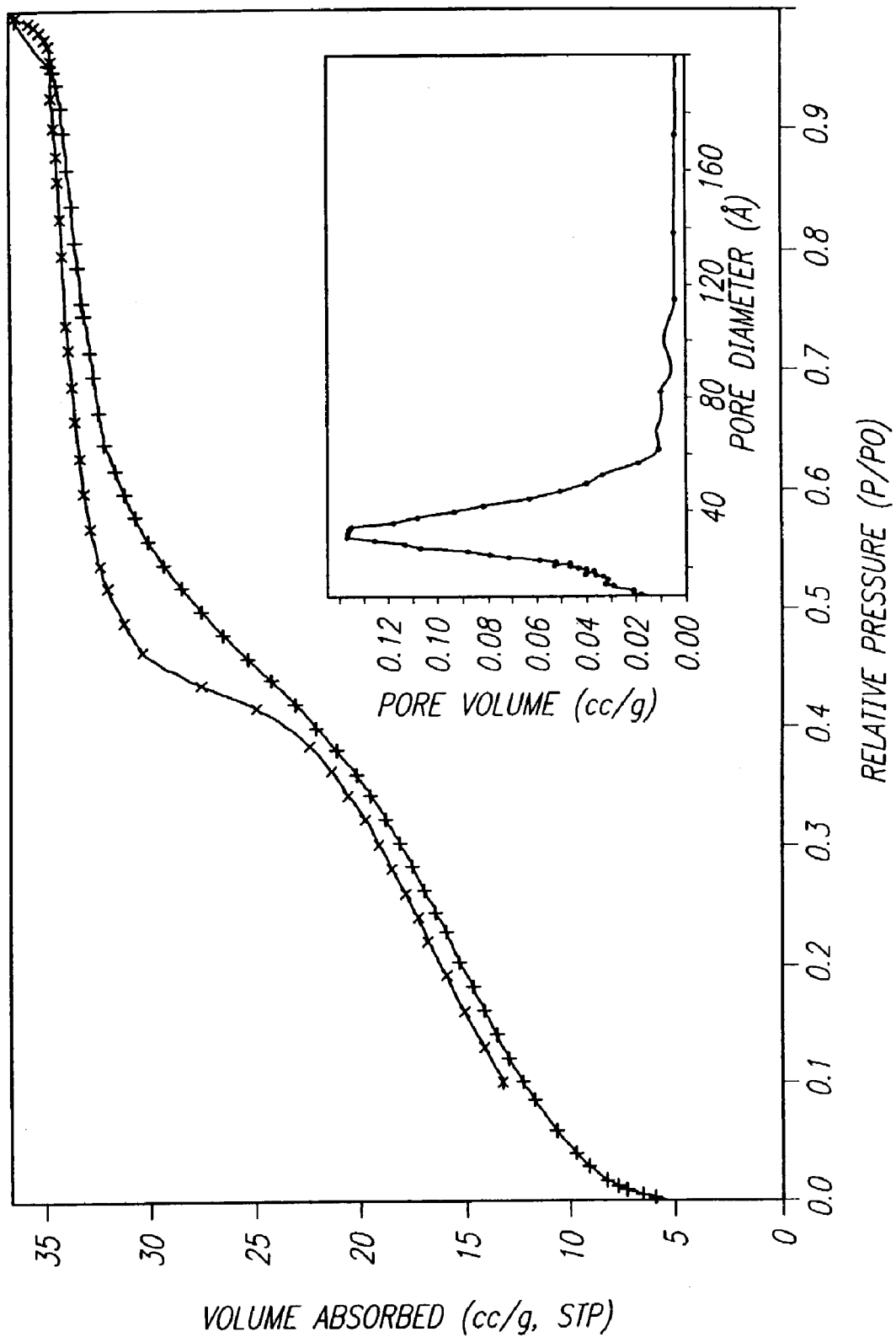
FIG. 29 shows nitrogen adsorption-desorption isotherms and pore size distribution plots (inset) calculated using BJH model from the adsorption branch isotherm for calcined $ZrO_2$. The isotherms were measured using a Micromeritics ASAP 2000 system. The samples were outgassed overnight at 200° C. before the analyses.
Figure 30A:
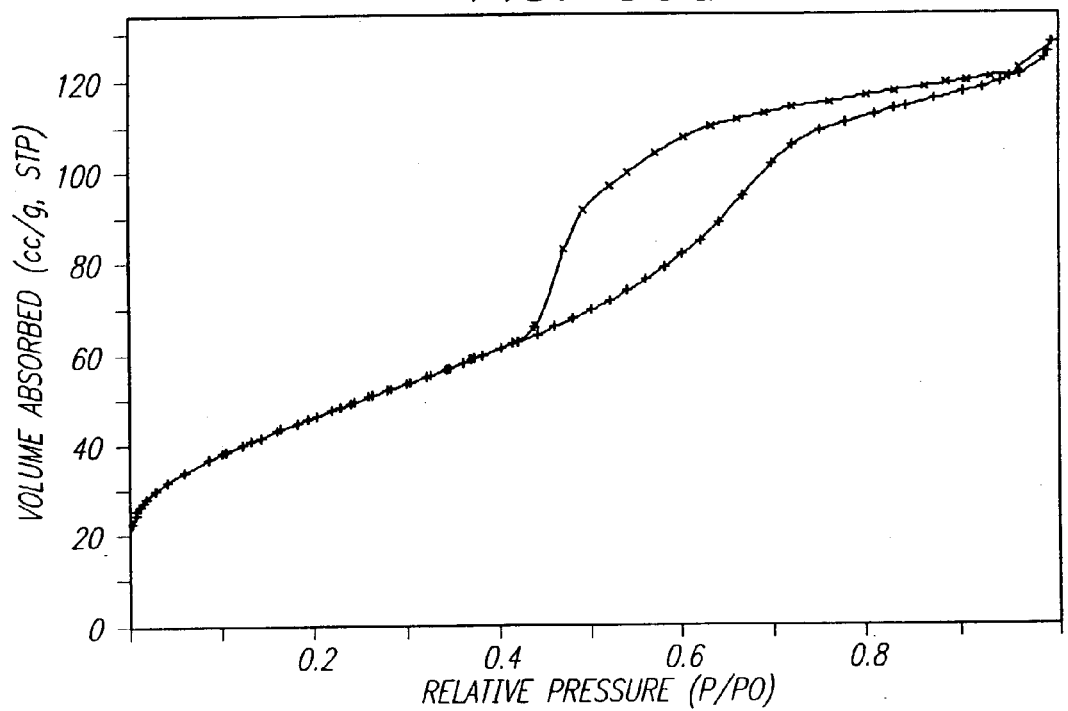
FIG. 30 shows nitrogen adsorption-desorption isotherms (a) and pore size distribution plots (b) calculated using BJH model from the adsorption branch isotherm for calcined $TiO_2$. Inset in (b) is the EDX spectrum obtained on the mesoporous samples.
Figure 30B:
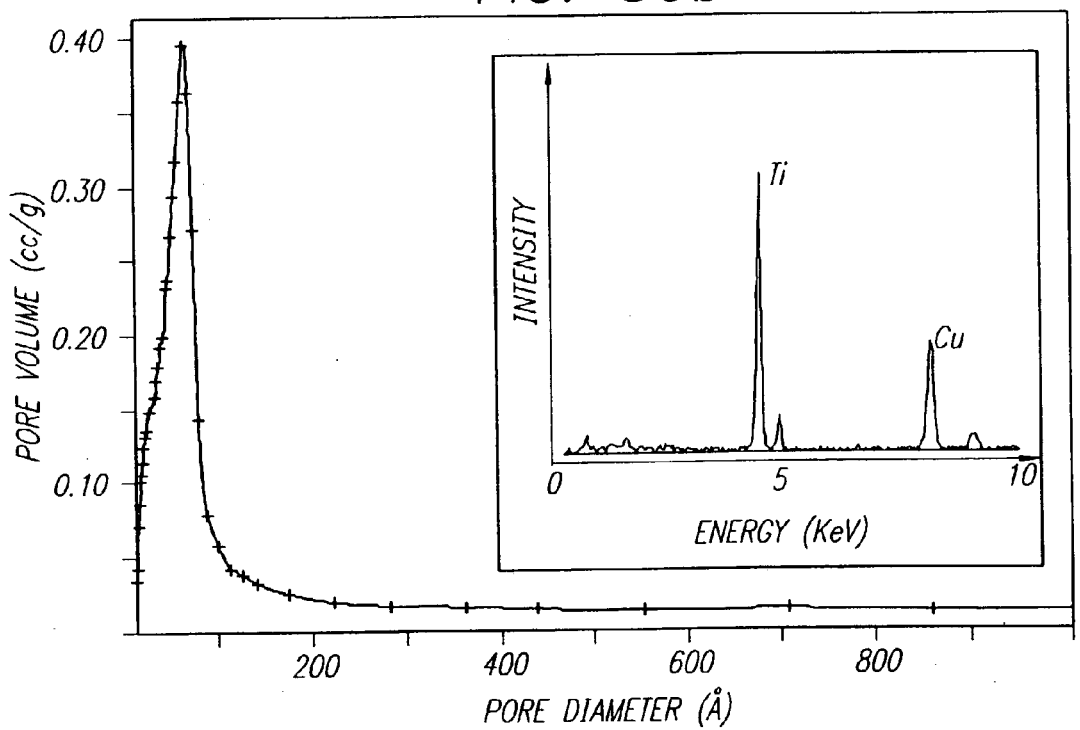
Figure 31:
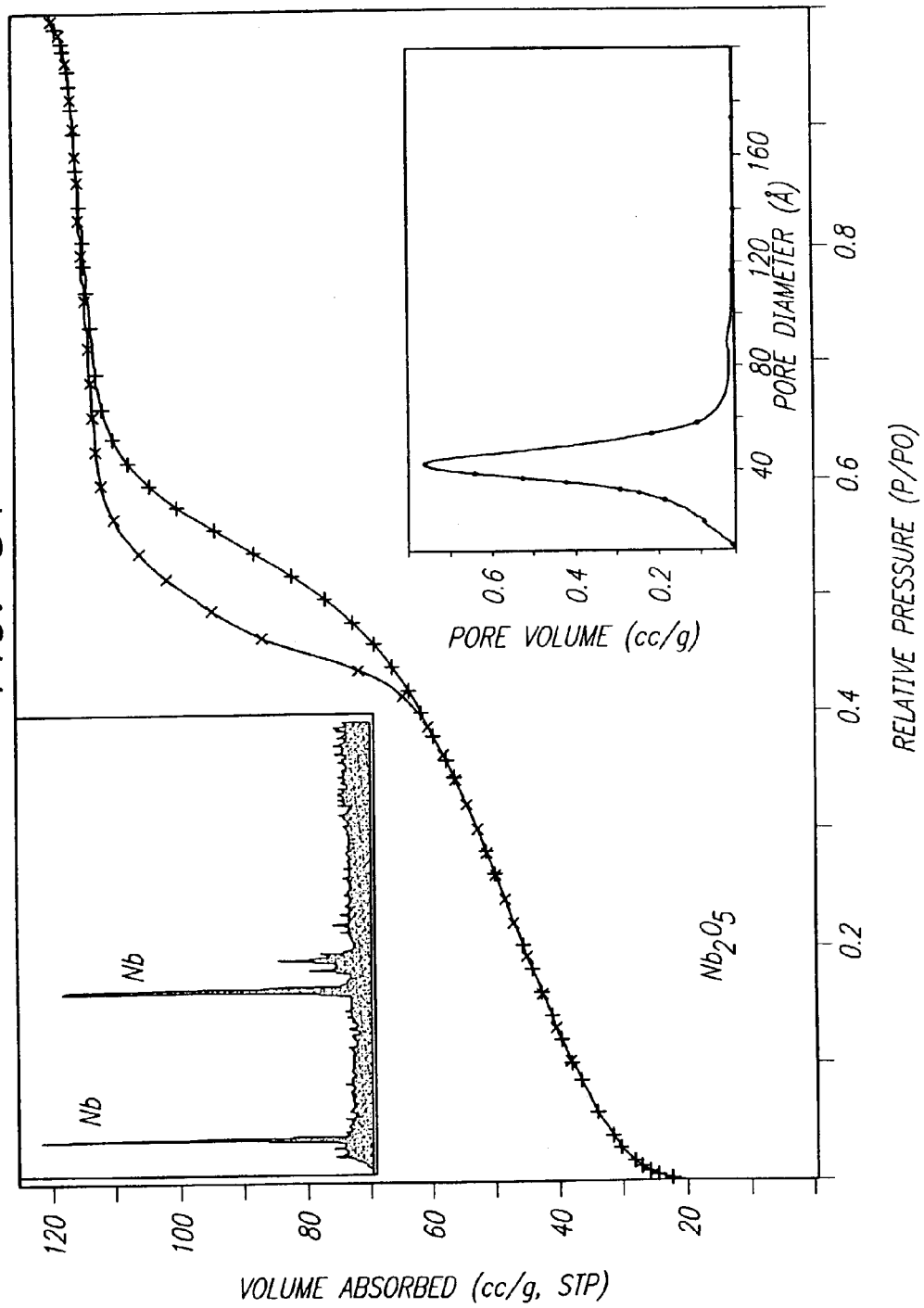
FIG. 31 shows nitrogen adsorption-desorption isotherms and pore size distribution plots (lower inset) calculated using BJH model from the adsorption branch isotherm for calined $Nb_2O_5$. EDX spectrum obtained on the mesoporous samples is shown in the upper inset.
Figure 32:
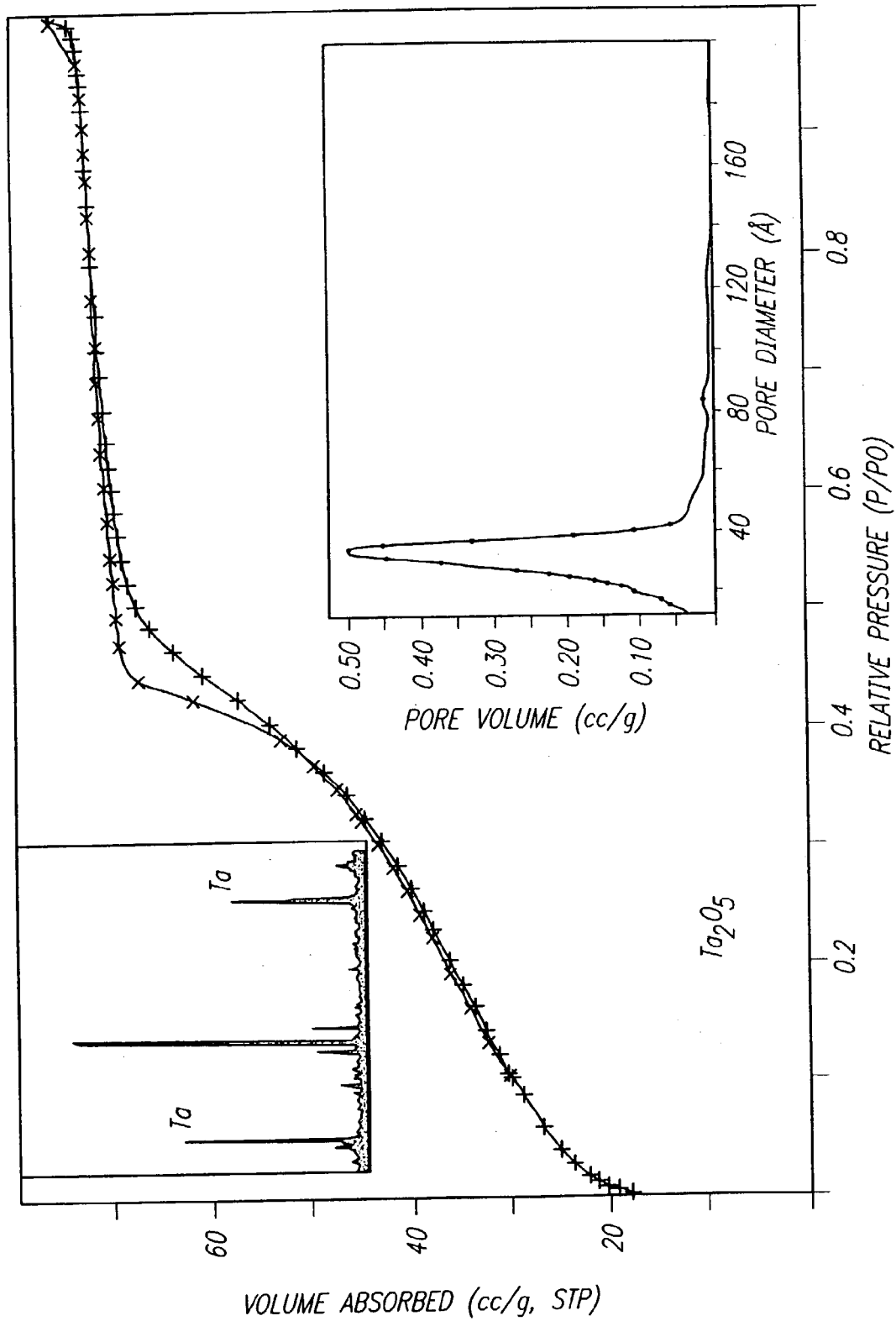
FIG. 32 shows nitrogen adsorption-desorption isotherms and pore size distribution plots (lower inset) calculated using BJH model from the adsorption branch isotherm for calcined $Ta_2O_5$. EDX spectrum obtained on the mesoporous samples is shown in the upper inset.
Figure 33:
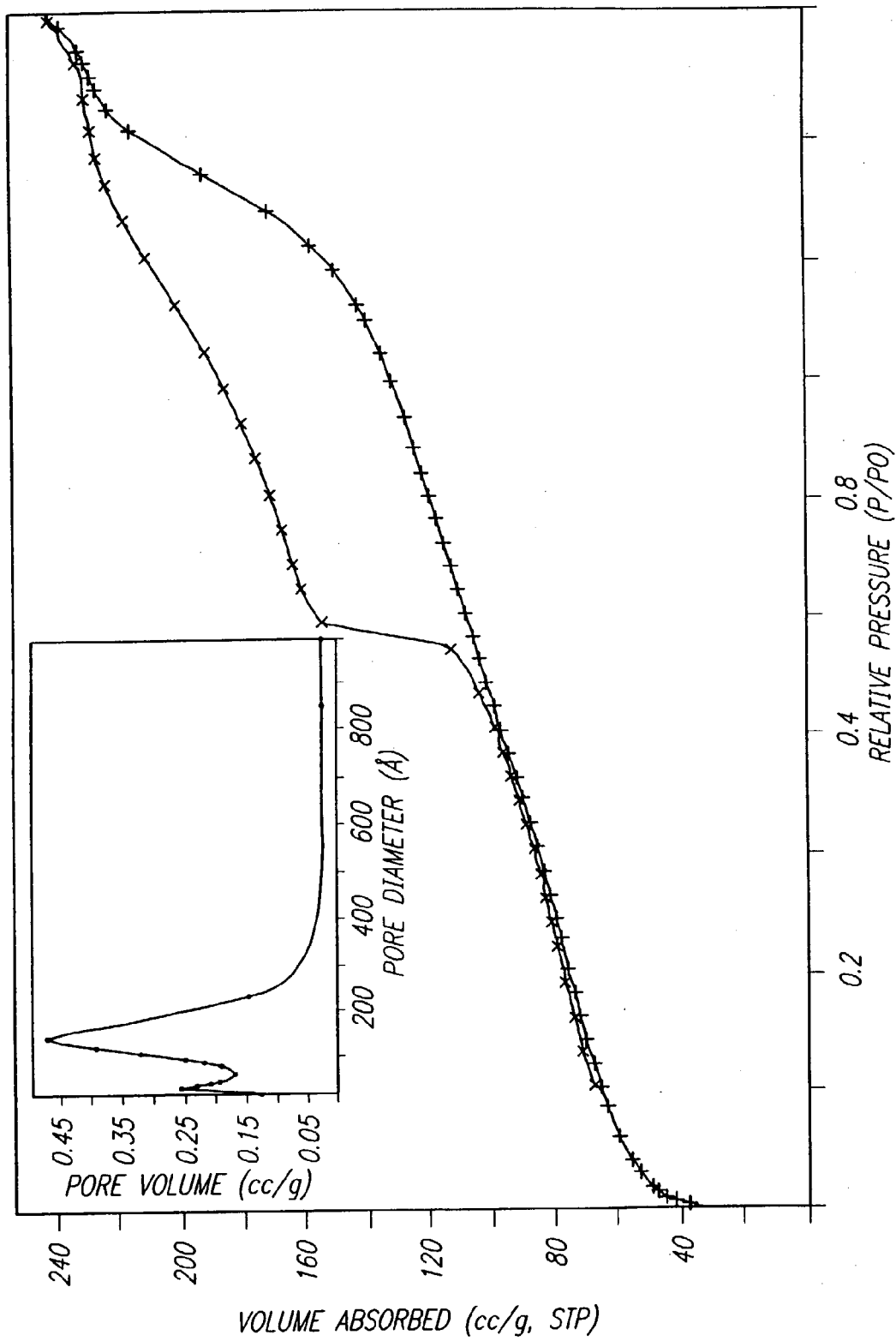
FIG. 33 shows nitrogen adsorption-desorption isotherms and pore size distribution plots (inset) calculated using BJH model from the adsorption branch isotherm for calcined $Al_2O_3$.
Figure 34:
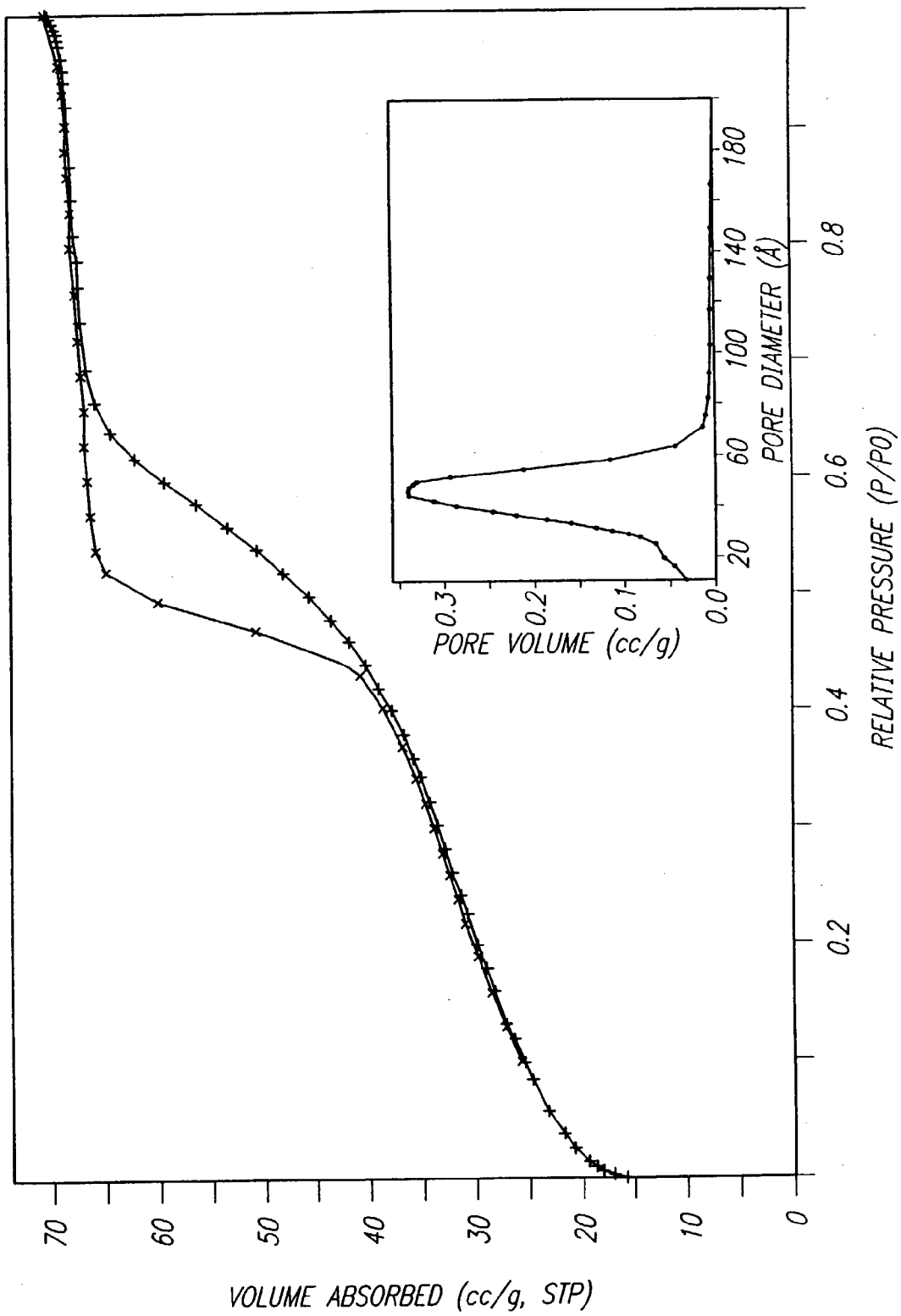
FIG. 34 shows nitrogen adsorption-desorption isotherms and pore size distribution plots (inset) calculated using BJH model from the adsorption branch isotherm for calcined $WO_3$.

FIG. 15 shows typical XRD patterns for mesostructured zirconium oxides prepared using $EO_{20}PO_{70}EO_{20}$ as the structure-directing agent before and after calcination. The as-made zirconium inorganic/polymer mesostructure (FIG. 15a) shows three diffraction peaks with d=115, 65, and 59 Å. After calcination, the diffraction peaks appear at higher 2θ angles with d=106, 60, and 53 Å (FIG. 15b). Both sets of diffraction peaks can be indexed as the (100), (110), and (200) reflections from 2-dimensional hexagonal mesostructures with lattice constants $a_0$=132 and 122 Å, respectively. Similar XRD results are obtained in other mesoporous metal oxides. The ordering lengths of these mesoporous metal oxides (Table 4) are substantially larger than those of materials previously reported.

Thermogravimetric experiments indicate that the block copolymer is completely removed upon calcination at 400° C. The appearance of low-angle diffraction peaks indicates that mesoscopic order is preserved in the calcined metal oxide materials. This is confirmed by TEM images obtained from mesoporous samples. As examples, FIGS. 16–26 show TEM images of mesoporous $ZrO_2$, $TiO_2$, $SnO_2$, $WO_3$, $Nb_2O_5$, $Ta_2O_5$, $Al_2O_3$, $HfO_2$, $SiTiO_4$, $SiAlO_{3.5}$, and $ZrTiO_4$ recorded along the [110] and [100] zone axes of the 2-dimensional hexagonal mesostructures. In each case, ordered large channels are clearly observed to be arranged in hexagonal arrays. The pore/channel walls are continuous and have thicknesses of ~3.5–9 nm. They are substantially thicker than those typical of metal oxides prepared using alkyammonium ion surfactant species as the structure-directing agents. In addition, energy dispersive X-ray spectroscopy (EDX) measurements made on the calcined samples show the expected primary metal element signals with trace of Cl signal, which confirms that the inorganic walls consist predominantly of metal-oxygen networks.

Furthermore, selected area electron diffraction patterns (ED) recorded on mesoporous $ZrO_2$, $TiO_2$, $SnO_2$, and $WO_3$ show that the walls of these materials are made up of nanocrystalline oxides that show characteristic diffuse electron diffraction rings (FIGS. 16–18 and 20 insets). Wide-angle X-ray diffraction studies of calcined samples also clearly show broad peaks that can be indexed according to the corresponding oxide crystalline phase. FIG. 15d shows a wide-angle diffraction pattern for the calcined $Zro_2$ sample. The sizes of the nanocrystals in the calcined materials are estimated to be ~2 nm using the Scherrer formula. In addition, bright-field and dark-field (BF/DF) TEM imaging were employed to study the distribution of these nanocrystals. FIGS. 27 and 28 show such images recorded on same area of one thin mesoporous $TiO_2$ and $ZrO_2$ sample. As can be seen in the dark field image (FIGS. 27b, 28b), the oxide nanocrystals (~2 nm) are uniformly embedded in a continuous amorphous inorganic matrix to form semicrystalline wall structures. This is the first time that the combination of electron diffraction, X-ray diffraction, and bright field/dark field TEM imaging has been used to conclusively demonstrate that our mesoporous metal oxides have nanocrystalline framework.

FIGS. 29–36 show BET isotherms that are representative of mesoporous hexagonal $ZrO_2$, $TiO_2$, $Nb_2O_5$, $Ta_2O_5$, $Al_2O_3$, $WO_3$, $SiTiO_4$, and $ZrTiO_4$. Barrett-Joyner-Halenda (BJH) analyses show that the calcined hexagonal mesoporous metal oxides exhibit pore sizes of 35–140 Å, BET surface areas of 100–850 $M^2/g$, and porosities of 40–60%. The pore sizes are again substantially larger than the previous reported values. For most of the isotherms obtained on these metal oxides, three well-distinguished regions of the adsorption isotherm are evident: (1) monolayer-multi layer adsorption, (2) capillary condensation, and (3) multilayer adsorption on the outer particle surfaces. In contrast to $N_2$ adsorption results obtained for mesoporous metal oxides prepared using low-molecular-weight surfactants with pore sizes less than 4 nm, large hysteresis loops that resemble typical $H_1$- and $H_2$-type isotherms are observed for these mesoporous metal oxides.

Figure 35A:
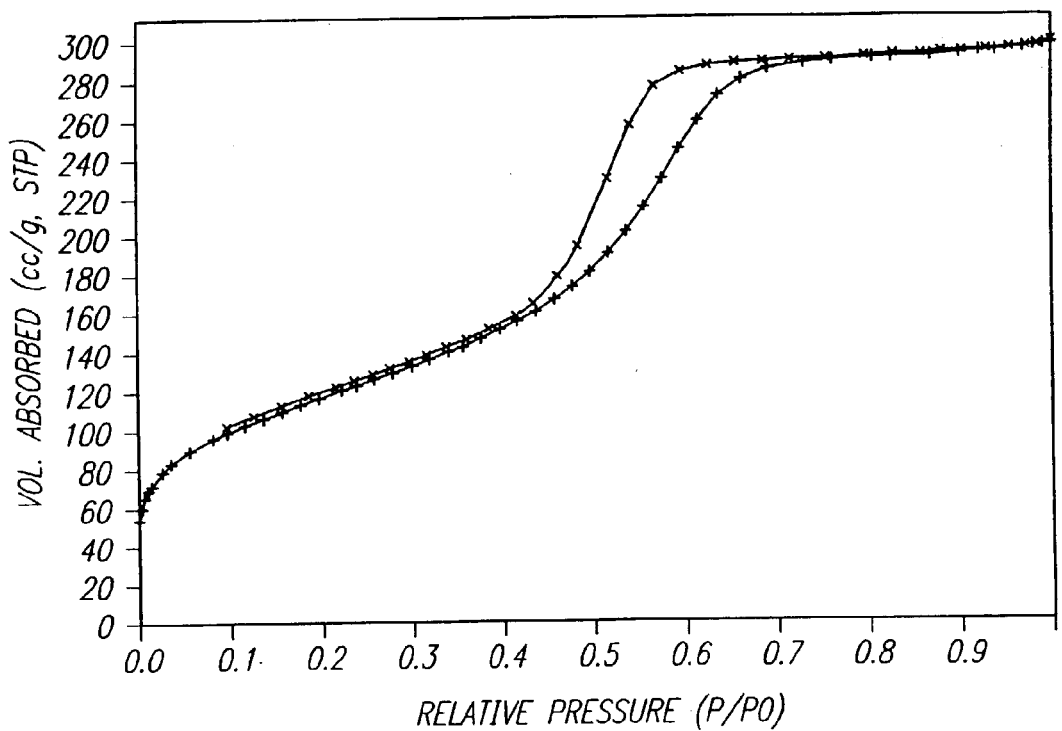
FIG. 35 shows nitrogen adsorption-desorption isotherms (a) and pore size distribution plots (b) calculated using BJH model from the adsorption branch isotherm for calcined $SiTiO_4$.
Figure 35B:
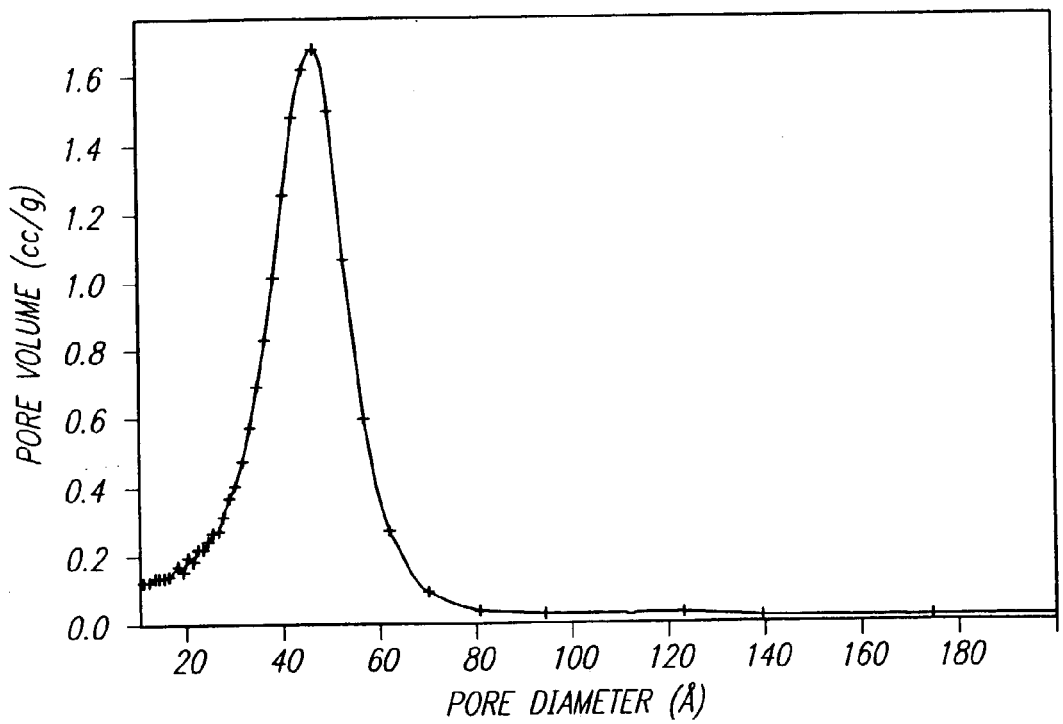
Figure 36A:
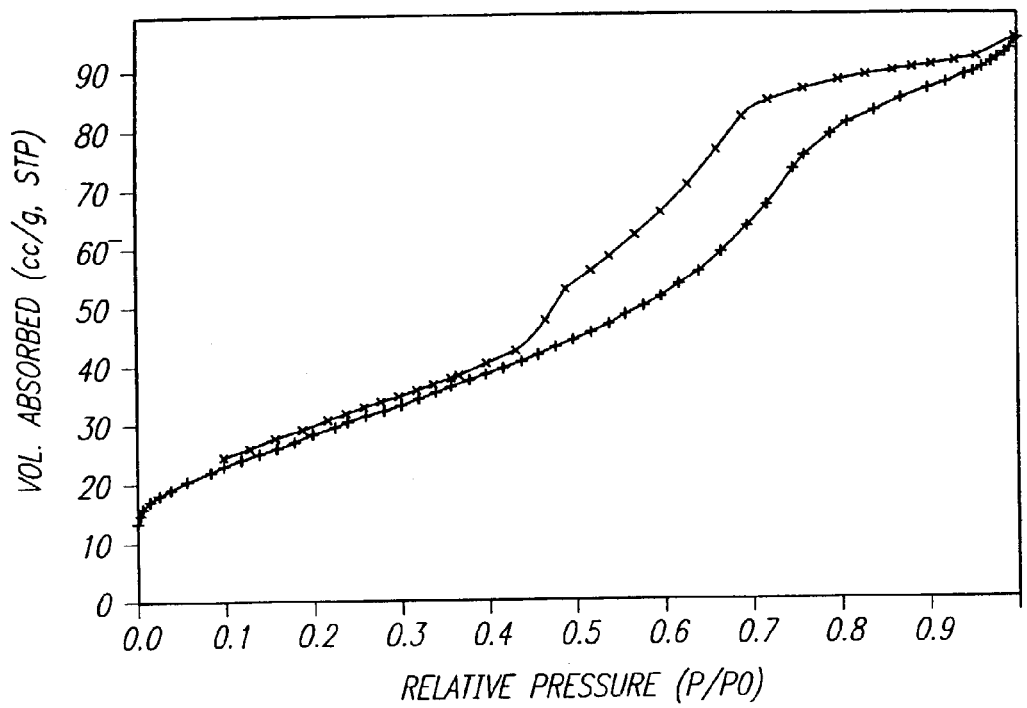
FIG. 36 shows nitrogen adsorption-desorption isotherms (a) and pore size distribution plots (b) calculated using BJH model from the adsorption branch isotherm for calcined $ZrTiO_4$.
Figure 36B:
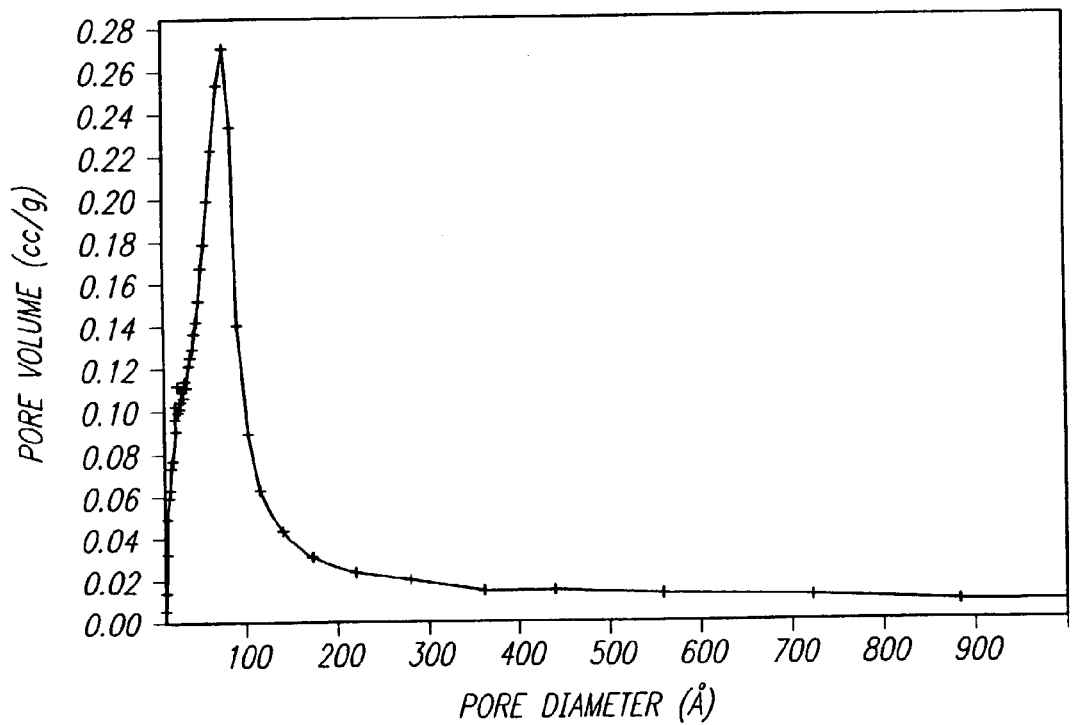
Figure 37:
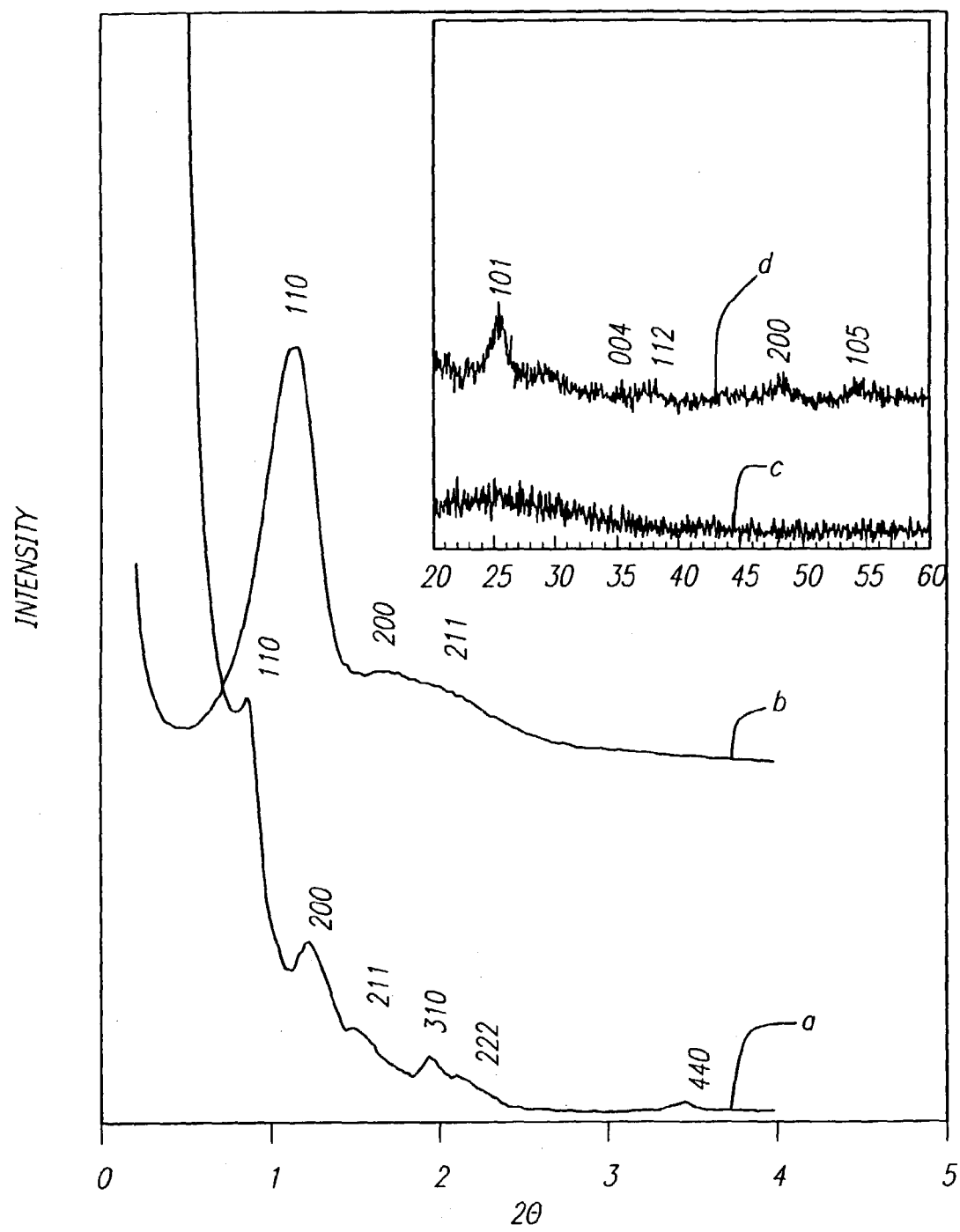
FIG. 37 shows low-angle and wide-angle X-ray diffraction (XRD) patterns of (a, c), as-made titanium/$EO_{20}BO_{75}$ composite cubic mesostructure and (b, d) calcined mesoporous $TiO_2$.

The foregoing examples used $EO_{20}PO_{70}EO_{20}$ copolymer species as the structure-directing agent. Mesoporous metal oxides with other mesostructures can be synthesized by using $EO_x$-$PO_y$-$EO_x$ or $EO_x$-$BO_y$ block copolymers with different ratios of EO to PO or BO. For example, when $EO_{75}BO_{25}$ copolymer is used as the structure-directing agent, mesoporous $TiO_2$ with cubic mesostructure can be prepared. FIG. 37 shows typical XRD patterns for mesostructured titanium oxides prepared using $EO_{75}BO_{70}$ as the structure-directing agent, before and after calcination. The as-made titanium inorganic/polymer mesostructure (FIG. 35a) shows six diffraction peaks with d=100, 70, 58, 44, 41, 25 Å, which can be indexed as (110), (200), (211), (310), (222), (440) reflections of an lm3 m mesophase. After calcination, the diffraction peaks appear at higher 2θ angles with d=76, 53, and 43 Å (FIG. 35b). These diffraction peaks can be indexed as the (110), (200), and (211) reflections from lm3 m mesostructures. The cubic mesostructure is confirmed by the TEM imaging (FIGS. 38 39).

Films and monoliths (FIG. 40) can be produced by varying such synthetic conditions as the solvent, the ratio of inorganic/polymer, aging temperature, aging time, humidity, and choice of the block copolymer. Liquids that are common solvents for inorganic precursors and the block copolymers (e.g. methanol, ethanol, propanol, butanol) can be used during the synthesis. The temperature, the amount of water added, and the pH can adjusted to control formation of the mesostructures. Materials for specific applications can be formulated by appropriate modification of these parameters.

The advantages and improvements over existing practice can be summarized as follows:
(1) Robust, thick channel walls (35–90 Å) which give enhanced thermal and chemical stabilities.
(2) Very large pore sizes (3.5–14 nm)
(3) Use of low-cost inorganic precursors
(4) Versatile synthetic methodology using non-aqueous media that can be generally applied to vastly different compositions, among which mesoporous $SnO_2$, $WO_3$, and mixed oxides $SiTiO_4$, $ZrTiO_4$, $Al_2TiO_5$ are synthesized for the first time.
(5) For the first time, conclusive demonstration of the nanocrystallinity of the framework in mesoporous $Zro_2$, $TiO_2$, $SnO_2$, $WO_3$ using XRD, ED and BFIDF TEM imaging
(6) Mesoporous metal oxides with various physical properties including semiconducting, low dielectric-constant, high dielectric-constant, and negative thermal expansion.

Crystallization of inorganic species during cooperative inorganic/organic self-assembly can lead to macroscopic phase separation of the inorganic and organic components. This is because crystallization energies often dominate the interaction energies that stabilize the inorganic-organic interface, thereby disrupting the establishment of mesostructural order. This is particular the case for non-lamellar phases. In the present invention, this situation is successfully circumvented by using conditions that initially produce a mesoscopically ordered material with an amorphous inorganic wall structure (FIGS. 15c and 35c) within which a high density of nanocrystals can subsequently be nucleated upon calcination. The thick wall and the noncrystallized inorganic matrix prevent this partially crystalline structure from collapsing by effectively sustaining the local strain caused by the nucleation of the nanocrystals. The coexistence of mesoscopic ordering and framework nanocrystallinity is extremely important for catalysis, sensor, and optoelectronic applications.

To the best of our knowledge, there has been no previous report of mesoporous metal oxide synthesis with such simplicity and versatility. The formation, with such unprecedented simplicity and generality, of large-pore mesoscopically ordered metal oxides suggests that the same general inorganic/block polymer assembly mechanisms may be operating. In fact, it is well documented that alkylene oxide segments can form crown-ether type complexes with many inorganic ions, through weak coordination bonds. The multivalent metal species (M) can associate preferentially with the hydrophilic PEO moieties, as indicated in Scheme 1, because of their different binding capabilities with poly (ethylene oxide) (PEO) and poly(propylene oxide) (PPO). The resulting complexes then self-assemble according to the mesoscopic ordering directed principally by the microphase separation of the block copolymer species, and subsequently cross-link and polymerize (Scheme 1) to form the mesoscopically ordered inorganic/polymer composites.

Scheme 1

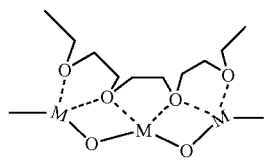

The proposed assembly mechanism for these diverse mesoporous metal oxides uses PEO-metal chelating interactions in conjunction with electrostatics, van der Waals forces, etc., to direct mesostructure formation.

A unique feature of the current synthetic methodology is use of inorganic precursors in non-aqueous media. Because of the lower electronegativies of the transition metals compared to silicon, their alkoxides are much more reactive towards nucleophilic reactions such as hydrolysis and condensation. There has been some work on the nonhydrolytic sol-gel chemistry of inorganic oxides, a non-hydrolytic route involving carbon-oxygen bond cleavage instead of the metal-oxygen bond which has a general tendency to delay crystallization of the metal oxides, a very important for the first step of our inorganic-copolymer cooperative self-assembly process. In addition, the hydrolytic route to metal oxides often leads to difficulties in controlling stoichiometry and homogeneity. Homogeneity depends on the rate of homocondensation (i.e. formation of M-O-M and M'-O-M') versus the rate of heterocondensation, which can be hardly controlled in the hydrolytic process because of the different reactivities of the various precursors towards hydrolysis and condensation. However, in principle, the non-hydrolytic process should favor the formation of homogeneous binary oxides from different metal precursors because of the decreased difference in hydrolysis and condensation rates for different inorganic sources in non-aqueous media. This has been successfully demonstrated in the mesoporous mixed oxides syntheses using the methods of this invention.

This utilization of block copolymer self-assembly in conjunction with chelating complexation for inorganic/organic cooperative assembly in the non-aqueous media make it possible to synthesize mesoporous materials with vastly different compositions exemplified in Table 4.

Cooperative Multiphase Assembly of Meso-macro Silica Membranes

Here we describe a novel procedure for the synthesis of artificial coral silica membranes with 3-d meso-macro structures. This process utilizes multiphase media while including microphase separation block copolymer/silica composite and macrophase separation between strong electrolytes and the composite in a single step. We find that strong electrolytes such as NaCl, LiCl, KCl, $NH_4Cl$, $KNO_3$, or even transition metal cationic salts such as $NiSO_4$, can be used to prepare meso-macro silica membranes that are formed at the interface of droplets of these inorganic salt solution. It is well known that in nature, macroscopic ordered silica structure such as diatom and coral are grown through a protein modified process in the ocean environments that are rich in inorganic salts such as NaCl. The process used in this study may be significant in understanding the formation of diatom and coral in nature which also can be considered as a 3-phase media process: the environment of the cell, the cell membrane and the aqueous media within the cell.

The silica membranes (size ~4 cm×4 cm, thickness ~5 mm) with 3-d meso-macro silica network structures that we have prepared show oriented continuous rope, tyroid, and grape vine or dish pinwheel, and gyroid, morphologies depended on the electrolyte strength of the inorganic salts or amphiphilic block copolymer templates. The macropore size (0.5–100 μm) can be controlled by inorganic salts and evaporation rate of the solvent. The mesoscopic structures can be highly ordered 2-d honeycomb (pore size 40~90 Å) or 3-d cubic packing, and controlled by the amphiphilic block copolymer templates. These artificial coral meso-macro silica membranes are thermally stable and exhibit a large surface areas up to 1000 $cm^2$ μg and pore volumes up to 1.5 $cm^3$/g.

The silica membranes were prepared by the use of two-step sol-gel chemistry. First oligomeric silica sol-gel was obtained by pre-hydrolysizing of tetraethoxysiliane (TEOS) in ethanol solution by an acid-catalyzed process. Second, the oligomeric silica sol-gel was added into a mixture solution of poly(ethylene oxide)-block-ploy(propylene oxide)-block-poly(ethylene oxide) (PEO-PPO-PEO) triblock copolymer and inorganic salts in water and ethanol. The final composition of this mixture was range of 1 TEOS: $(6.8~34)\times10^{-3}$ copolymer 0.51~3.0 inorganic salt: $18~65H_2O$: 0.002~0.04 HCl: 11~50 EtOH. The silica membranes with 3-d meso-macro structures were obtained after drying at room temperature, washing with water to remove the inorganic salts, and calcination to completely remove the organic block copolymer.

In a typical synthesis, 2.08 g TEOS (Aldrich) were added to 5 g ethanol, 0.4 g water and 0.4 g (0.1 M) of HCl solution with stirring at room temperature for 0.5 h, then heated at 70° C. without stirring for 1 h. After cooling to room temperature, 1 g $EO_{20}PO_{70}EO_{20}$ (PLURONIC P123, Aldrich/BASF, average molecular weight 5800), 1 g NaCl, 10 g ethanol and 10 g water were added to this solution with stirring at room temperature for 1 h. The resultant solution was transferred into an open petri dish, allowed to evaporate at room temperature. After complete drying, the solid membrane was removed from the dish, 20 g water added and then heated in a sealed container at 100° C. for 3 days to dissolve the inorganic salts. After cooling to room temperature, the solid silica membranes were washed with de-ionized water and dried at room temperature. The as-synthesized silica membranes were calcined at 500° C. for 6 h in air to completely remove all organic block copolymers.

FIG. 41 shows several representative scanning electron microscope (SEM) images, obtained on a JEOL 6300-F microscope, of the silica membranes and inorganic salt (NaCl) crystal co-grown with the membranes by sol-gel chemistry. The silica membranes prepared from NaCl solution show 3-d macroscopic network structures and a coral-like morphology (FIG. 41a). The reticular 3-d network (thickness of ~1 μm) of the silica membrane is made up of continuous rope-like silica which exhibits highly mesoscopic ordering (see below). The silica membranes can be as large as ~4 cm×4 cm depended on the size of the container that is used. The thickness of the silica membranes can be varied from 10 μm to 5 mm.

Figure 41A:
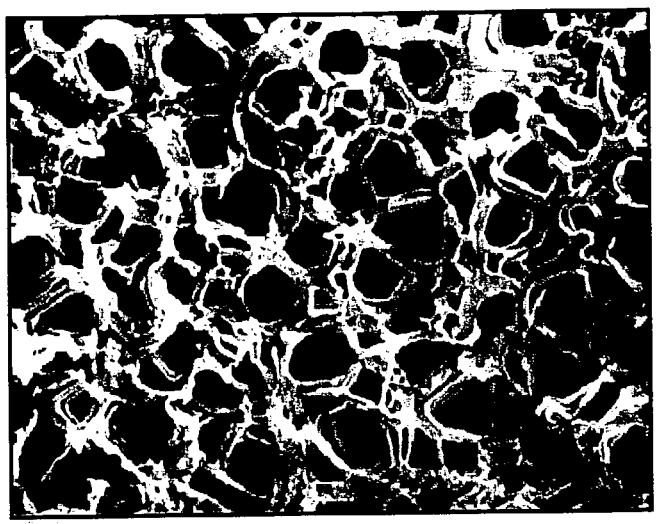
FIG. 41 shows scanning electron micrographs (SEM) of (a, b) as-synthesized meso-macro silica membranes prepared by using P123 block copolymer ($EO_{20}PO_{70}EO_{20}$) in NaCl solution after washing out NaCl with de-ionic water; (c), small macropore size silica membrane prepared by adding a little amount ethylene glycol in P123 block copolymer and NaCl solution; (d), silica membrane prepared with fast evaporation by using P123 block copolymer in NaCl solution. (e), silica membrane with grape vine morphology prepared with high concentration of NaCl; (f), inorganic salt NaCl crystals co-grown with the silica membrane.
Figure 41B:
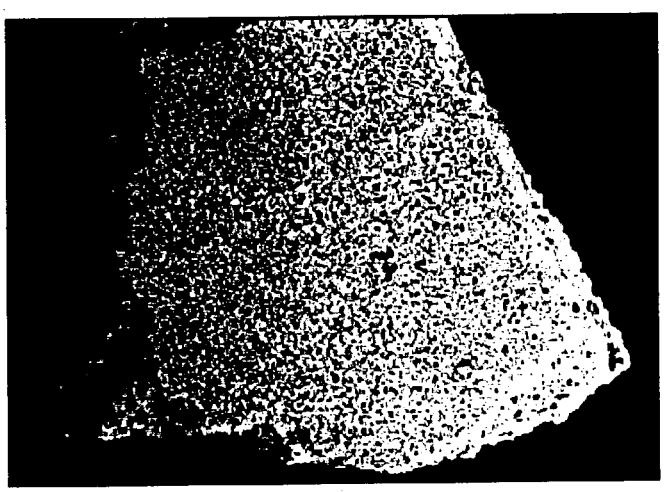
Figure 41C:
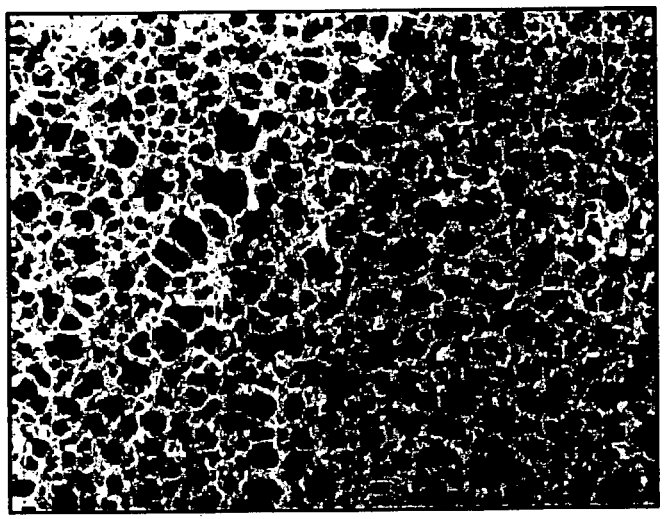
Figure 41D:
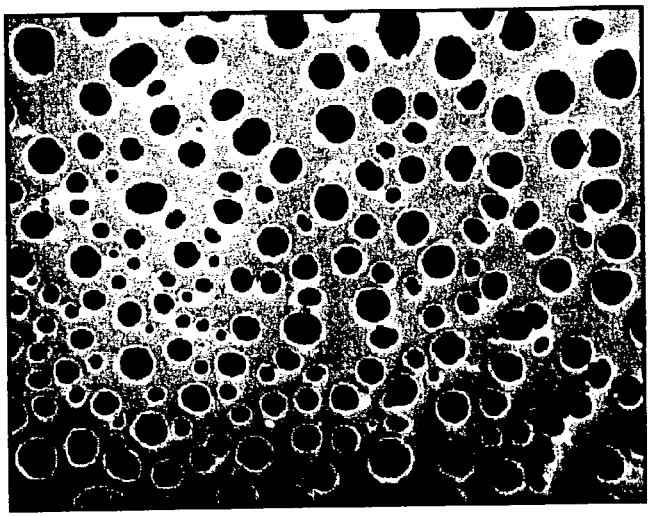

As shown in FIG. 41b, the whole silica membrane shows similar local macroscopic structure that is not long-range ordering. The average macropore size of the silica membranes is about ~2 μm (±0.4) (FIG. 41a) and can be varied from ~0.5 μm to ~100 μm by changing the evaporation rate or the electrolyte strength of the inorganic salts. For example, when a small amount of ethylene glycol is added into the sol-gel solution to slow the evaporation rate, a small macropore size (~0.5 μm) is obtained as shown in FIG. 41c. Of interest is finding that when the evaporation rate is low, the thickness of the silica network is decreased several hundreds nanometer as shown in FIG. 41c. When the evaporation rate is high, the macropore size of the silica membranes can be as large as ~10 μm, the framework thickness is increased (as shown in FIG. 41d) and the macroscopic structure of the silica membranes is changed to a 2-d honey comb channel structure.

Figure 41E:
Figure 41F:
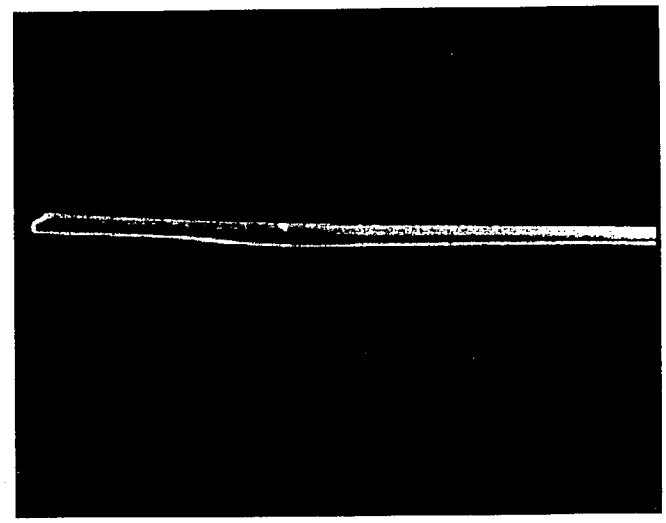

The electrolyte strength of the inorganic salts also can be used to control the macropore size. By using stronger electrolytes, for example, $MgSO_4$, the macropore size can be as much as ~20 μm. In addition, the morphology of the silica membrane can be modified through changing the concentration of inorganic salts. Low concentrations of the inorganic salts result in an inhomogeneous silica membrane. While high concentrations, result in the grape vine morphology that makes up the silica membrane as shown in FIG. 41e.

The morphologies of the inorganic salt crystals are also affected by the organic block copolymer. For example, without the amphiphilic block copolymer, cubic crystals of NaCl as large as ~100 μm can be grown in the solution of water and ethanol, however, in the presence of the surfactant under our synthesis conditions, most NaCl crystals show an acicular (~1 μm in diameter) morphology (FIG. 41f, with a length of as much as 1 cm. When $NiSO_4$ is used as the inorganic salts in our synthesis condition, a disk-like morphology of $NiSO_4$ crystal is observed at the bottom of the silica membranes. This suggests that the crystallization of the inorganic salts can also be directed by block copolymers.

Besides NaCl, other inorganic salts such as LiCl, KCl, $NH_4Cl$, $Na_2SO_4$, $MgSO_4$, $NiSO_4$, $MgCl_2$, chiral $NaClO_3$, and organic acids such as, malic acid, can be used to form the silica membranes. FIG. 42 shows several representative scanning electron microscope (SEM) images of the meso-macroporous silica membranes prepared by using block copolymer P123 (a–c), or P65 (d) in different inorganic salt solutions. The morphology of the silica membranes is dependent on the electrolyte strength of the inorganic salts. For example, when LiCl, KCl, and $NH_4Cl$ are used, with electrolyte strengths comparable to that for NaCl, a similar coral-like morphologies (FIGS. 42a, b, c) are observed, although the network morphology of the silica membranes is somewhat different. However, when the inorganic salts with stronger electrolyte strengths such as $Na_2SO_4$, $MgSO_4$, are used in the synthesis, the macroscopic structures consist silica networks made up of toroid, pinwheel, dish, and gyroid morphologies (FIG. 43).

Figure 42A:
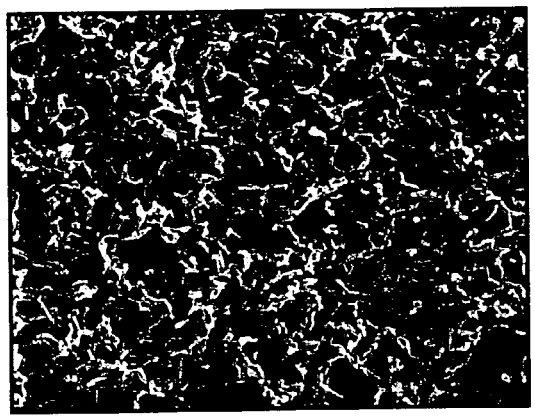
FIG. 42 shows scanning electron micrographs (SEM) of (a, b, c) as-synthesized meso-macro silica membranes prepared by using P123 block copolymer ($EO_{20}PO_{70}EO_2O$) in (a), KCl; (b), $NH_4Cl$; (c), $NaNO_3$ solution after washing out inorganic salts with de-ionic water. (d), large macropore size silica membrane prepared by using P65 block copolymer ($EO_{26}$, $PO_{39}EO_{26}$) in NaCl solution.
Figure 42B:
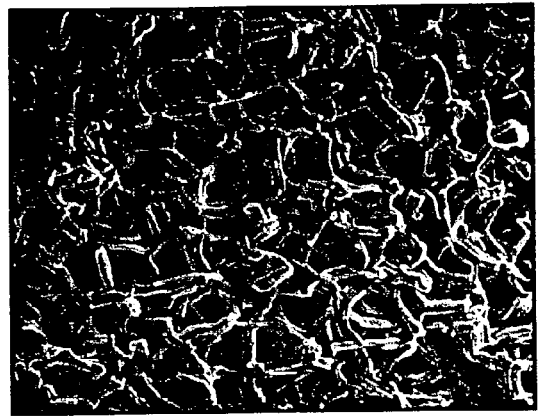
Figure 42C:
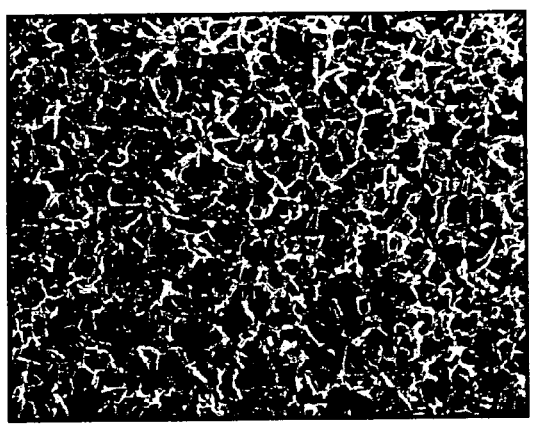
Figure 42D:
Figure 43A:
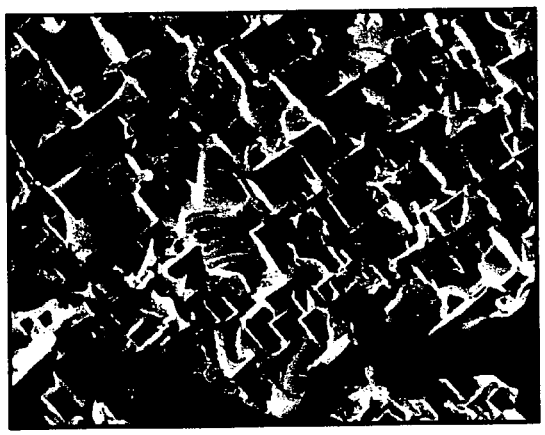
FIG. 43 shows SEM images of as-synthesized silica membranes after washed with water prepared by (a), using F127 block copolymer ($EO_{106}PO_{70}OE_{106}$) in NaCl solution; (b, c, d), using P123 block copolymer in (b), $MgSO_4$ solution; (c), $MgCl_2$ solution; (d), $Na_2SO_4$ solution.
Figure 43B:
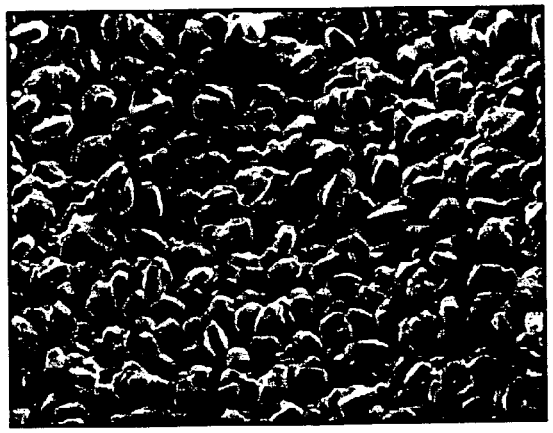
Figure 43C:
Figure 43D:
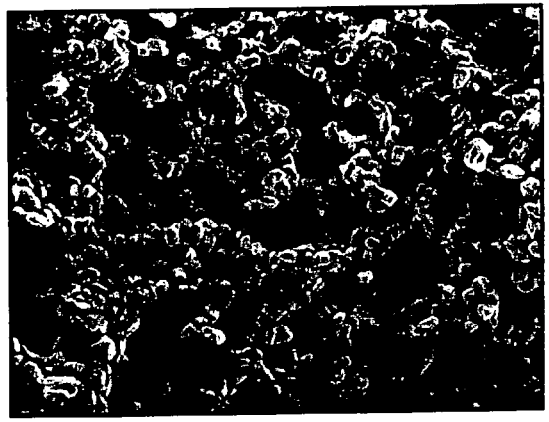

The macroscopic structure is also affected by the block copolymer. When higher aver-age molecular weight block copolymers such as PLURONIC F127 ($EO_{106}PO_{70}EO_{106}$) is used, cubic morphology is observed by SEM (FIG. 43a). This morphology results from silica grown around cubic NaCl crystals, suggesting a macroscopic inorganic crystal templating process for the mesoporous silica growth. When block copolymers such as PLURONIC P65 ($EO_{26}PO_{39}EO_{26}$) is used, the silica membrane with large macropore size is obtained (FIG. 42d).

Figure 44A:
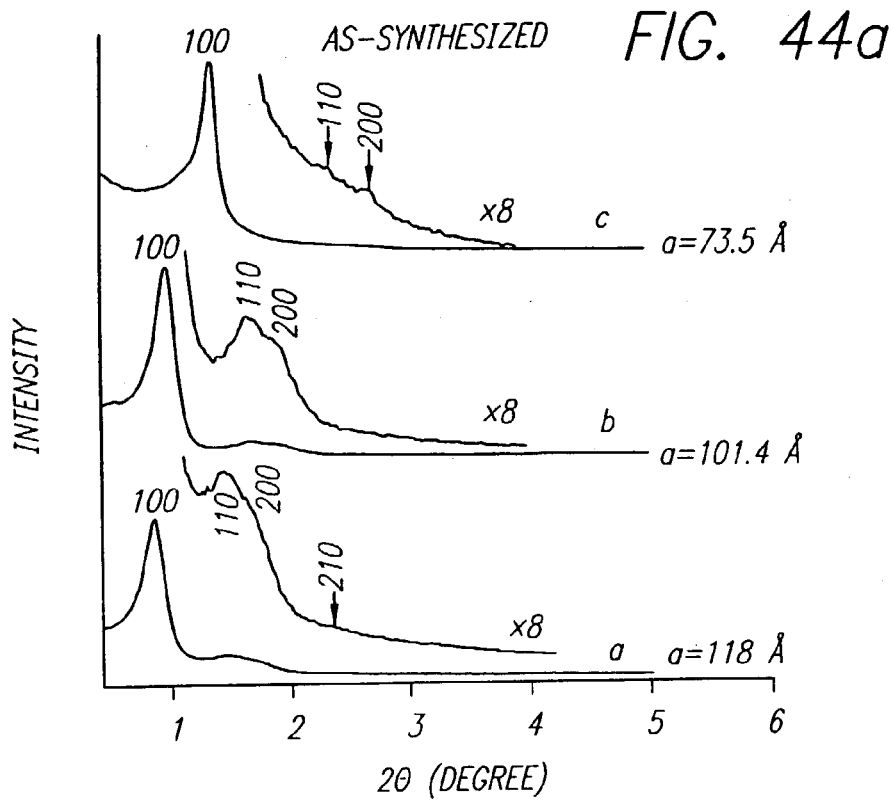
FIG. 44 shows powder X-ray diffraction (XRD) patterns of as-synthesized and calcined mesomacro silica membranes prepared using the amphiphilic polyoxyalkylene block copolymer (a), P123, $EO_?PO_{70}EO_{20}$; (b), P103, $EO_{17}PO_{74}EO_{17}$; (c); P65, $EO_{26}PO_{39}EO_{26}$. The chemical composition of the reaction mixture was 1 g copolymer: 0.017 mol NaCl: 0.01 mol TEOS: $4 \times 10^{-5}$ mol HCl: 0.72 mol $H_2O$: 0.33 mol EltOH.
Figure 44B:
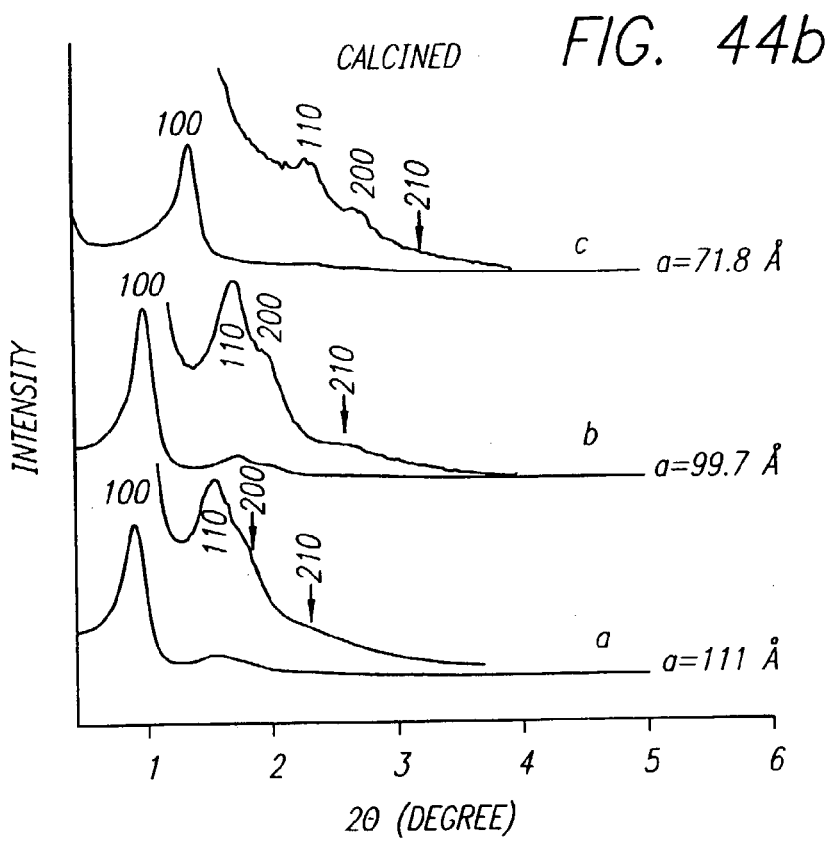

The mesoscopic ordering in these silica membranes formed by the cooperative self-assembly of inorganic silica species/amphiphilic block copolymer is mainly controlled by the block copolymer while can be characterized by the low-angle X-ray diffraction patterns (FIG. 44) and transmission electron microscope (TEM) (FIG. 45). The XRD patterns of FIG. 44 were acquired on a Scintag PADX diffractometer using Cu Kα radiation. For the TEM of FIG. 45 measurements, the sample was prepared by dispersing the powder products as a slurry in acetone and subsequently deposited and dried on a holey carbon film on a Cu grid. As shown in FIG. 44a, the coral-like silica membranes synthesized by using P123 triblock copolymer after removal of NaCl by washing, shows a typical hexagonal (p6 mm) XRD pattern for mesoporous materials with four diffraction peaks (a=118 Å), which is similar to that of SBA-15 described above. After calcination at 500° C. in air for 6 h, the four-peak XRD pattern is also observed and the intensity of the diffraction peaks is increased, suggesting that the p6 mm mesoscopic ordering is preserved and thermally stable, although the peaks appear at slightly larger 2θ values, with a=111 Å. The cell parameters of mesoscopic ordering on the silica membranes can be varied by using different triblock copolymers. For example, a=101 Å for PLURONIC P103 ($EO_{17}PO_{85}EO_{17}$) (FIG. 44b) and a=73.5 Å for PLURONIC P65 ($EO_{26}PO_{39}EO_{26}$) (FIG. 44c), these materials have 2D hexagonal (p6 mm) mesoscopic highly ordered structures.

Figure 45A:
FIG. 45 shows transmission electron micrographs (TEM) (a, b) of calcined silica membrane prepared using the block copolymer P 123 in NaCl solution recorded in (a), (100); (b), (110) zone axes; (c, d) of calcined silica membrane prepared by adding a little amount of ethylene glycol. TEM were taken on a 2000 JEOL electron microscope operating at 200 kV.
Figure 45B:
Figure 45C:
Figure 45D:

These results suggest that the presence of the inorganic salts such as NaCl does not greatly effect the cooperative self-assembly of block copolymer/silica to form highly ordered mesostructure. FIGS. 45a,b show TEM images of calcined silica membranes prepared by using P123 block copolymer in NaCl solution at different orientations, confirming that silica network of the membranes is made up of a 2-d p6 mm hexagonal mesostructure, with a well-ordered hexagonal array and one-dimensional channel structure. TEM images (FIG. 45c, d) of the silica membranes with small macropore size (~0.5 μm from SEM) prepared by adding a small amount of ethylene glycol show that the rope-like networks of the silica membranes is made up of loop-like mesoscopic silica with oriented 1-d channel arrays parallel to the long axis. These rope-like silicas form a 3-d network macroporous structure. It should be noted that when higher molecular weight block copolymer F127 is used as the mesoscopic structure-directing agents, a silica membrane with cubic mesostructure (a=217 Å) can be obtained, based on XRD and TEM results.

Figure 46A:
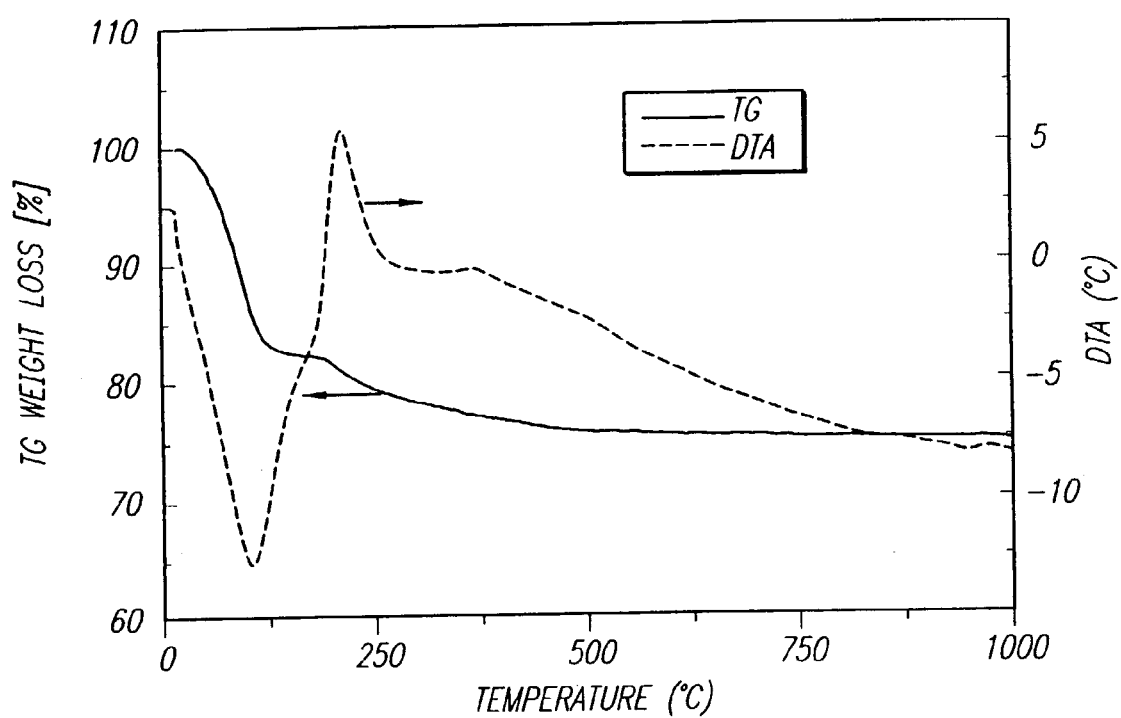
FIG. 46 shows thermogravimetric analysis (TGA) and differential thermal analysis (DTA) traces for the as-synthesized meso-macroporous silica membranes prepared by using the block copolymer P123 ($EO_{20}PO_{70}EO_{20}$) in NaCl solution, (top) after removal NaCl by washing with water; (bottom), without removal NaCl.
Figure 46B:
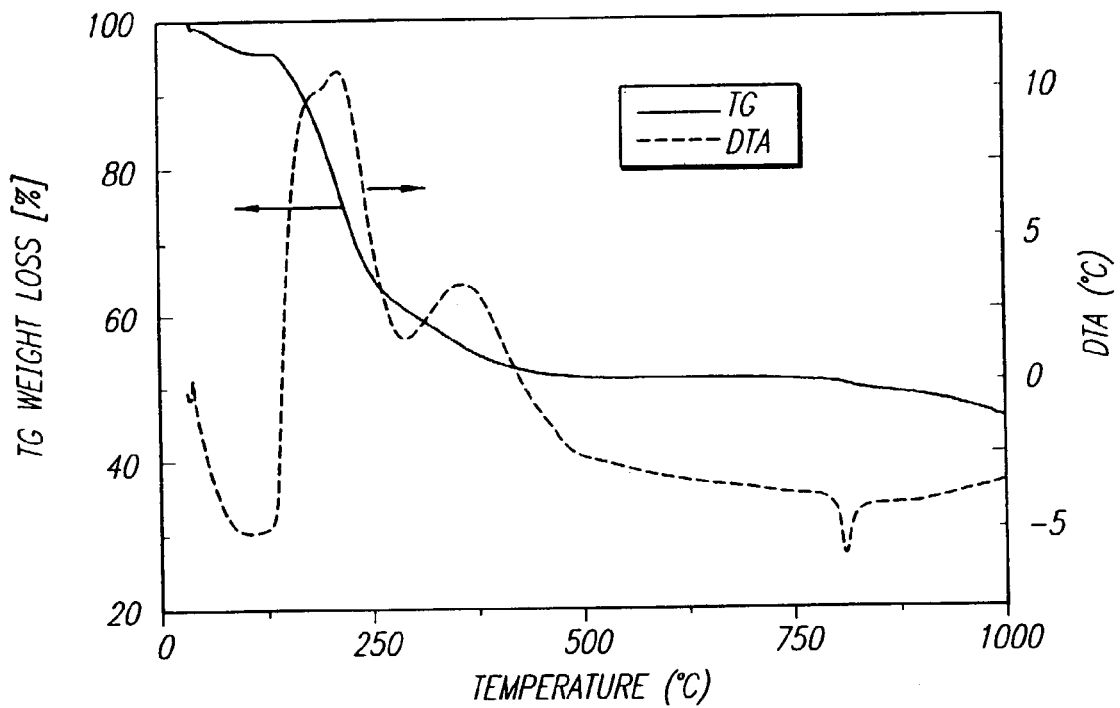

SEM images of the silica membranes after calcination at 500° C. in air show that the coral-like macrostructure is retained, demonstrating that the coral-like meso-macro silica membranes prepared with inorganic salts are thermally stable. Thermal gravimetric and differential thermal analyses (TGA and DTA) (FIG. 46) in air of the silica membranes prepared by using P123 block copolymer in NaCl solution after removal of the inorganic salts, show total weight losses of only 24 weight % (FIG. 46 top). A Netzsch Thermoanalyzer STA 409 was used for thermal analysis of the solid products, simultaneously performing TGA and DTA with heating rates of 5 $Kmin^{-1}$ in air. At 100° C. TGA registers a 18 weight % loss accompanied by an endothermic DTA peak caused from desorption of water, this is followed by a 6 weight % TGA loss at 190° C. which coincides with an exothermic DTA peak associated with decomposition of the organic block copolymer. By comparison, the silica membranes obtained without removed the inorganic salts show total weight losses of 50 weight % (FIG. 46 bottom). At 100° C. TGA registers a 4 weight % loss from physical adsorption, of water, followed by a 46 weight % TGA loss at 200° C. from decomposition of the organic block copolymer.

Figure 47A:
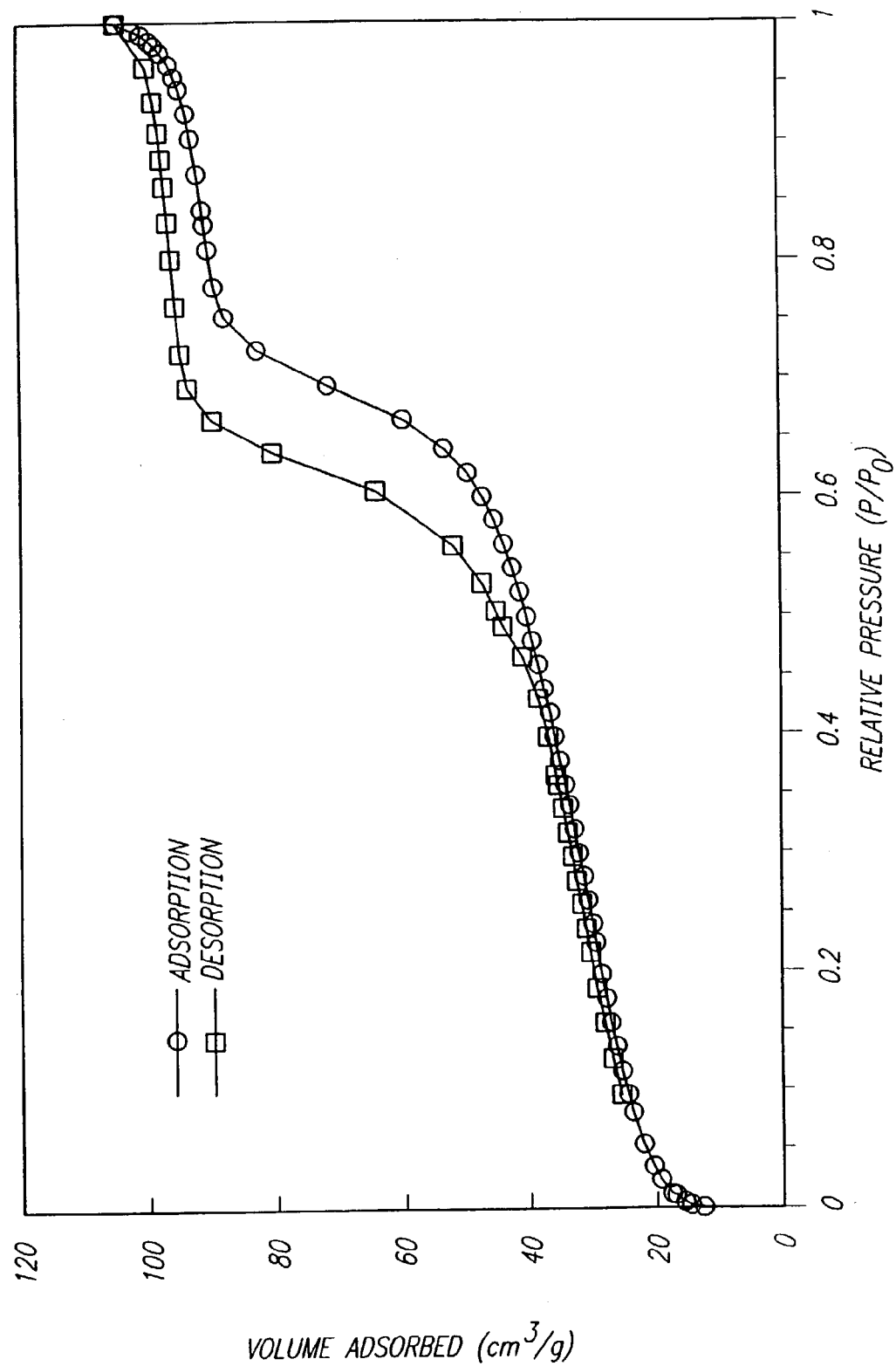
FIG. 47 shows nitrogen adsorption/desorption isotherm plots (a) and pore size distribution curves (b) for mesomacro silica membranes prepared using block copolymer P123 in NaCl solution without removal inorganic salt NaCl.
Figure 47B:
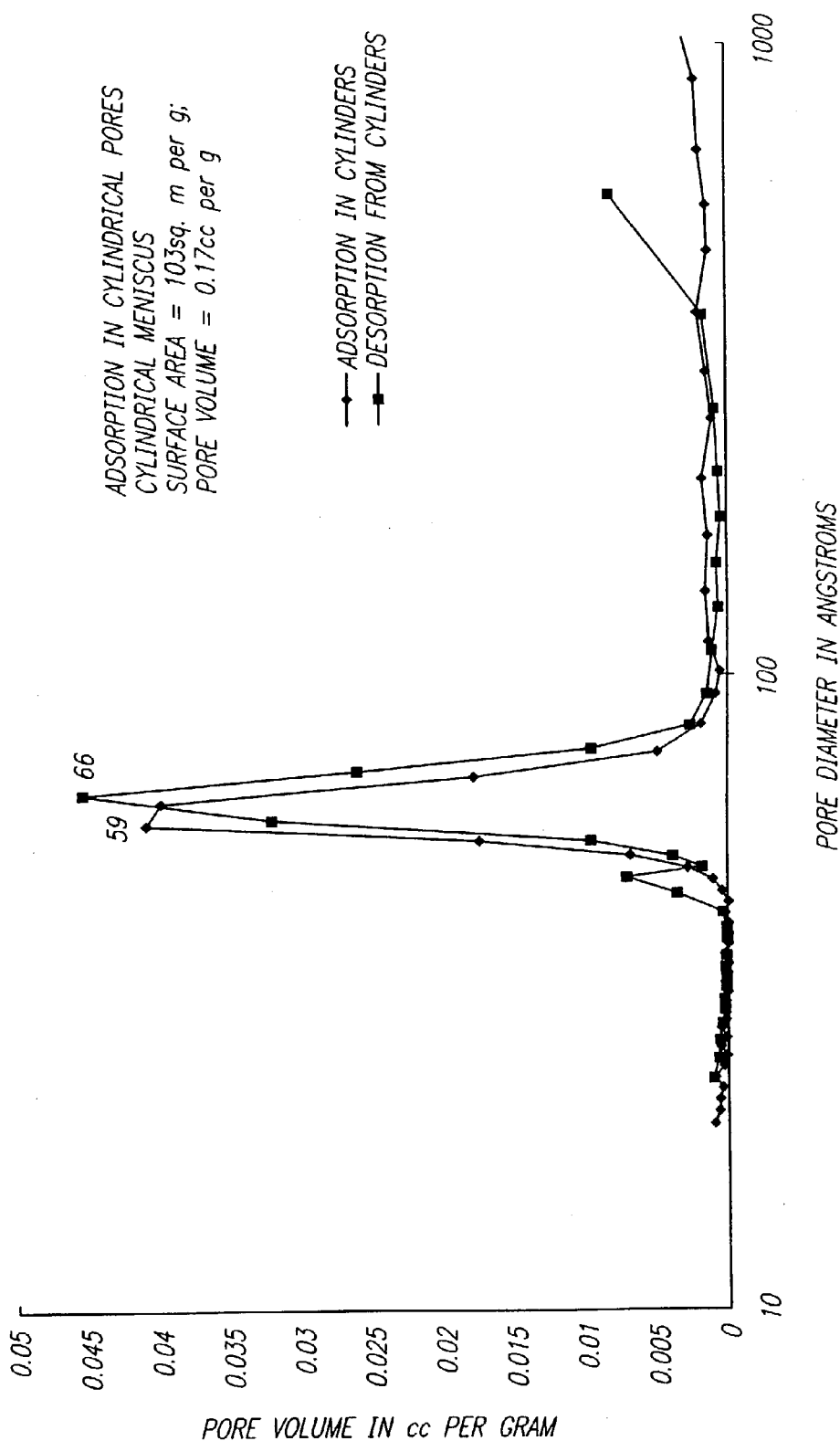

The above observations confirm that the interaction between silica species and block copolymer species is weak, and after washing with water 84 weight % of the block copolymer in the silica membranes is removed. After washing by water and without calcination, these silica membranes already show similar nitrogen sorption behavior to that for calcined silica membranes, (FIG. 47a, b) so that after washing, both macroporous (~2 μm) and mesoporous (60 Å) channels are already accessible. The isotherms of FIG. 47 were measured using a Micromeritics ASAP 2000 system. Data were calculated by using the BdB (Broekhoff and de Boer) model. The pore size distribution curve was obtained from an analysis of the adsorption branch of the isotherm. The pore volume was taken at $P/P_0$=0.985 signal point. The BET sample was pretreated at 200° C. overnight on the vacuum line.

Figure 48A:
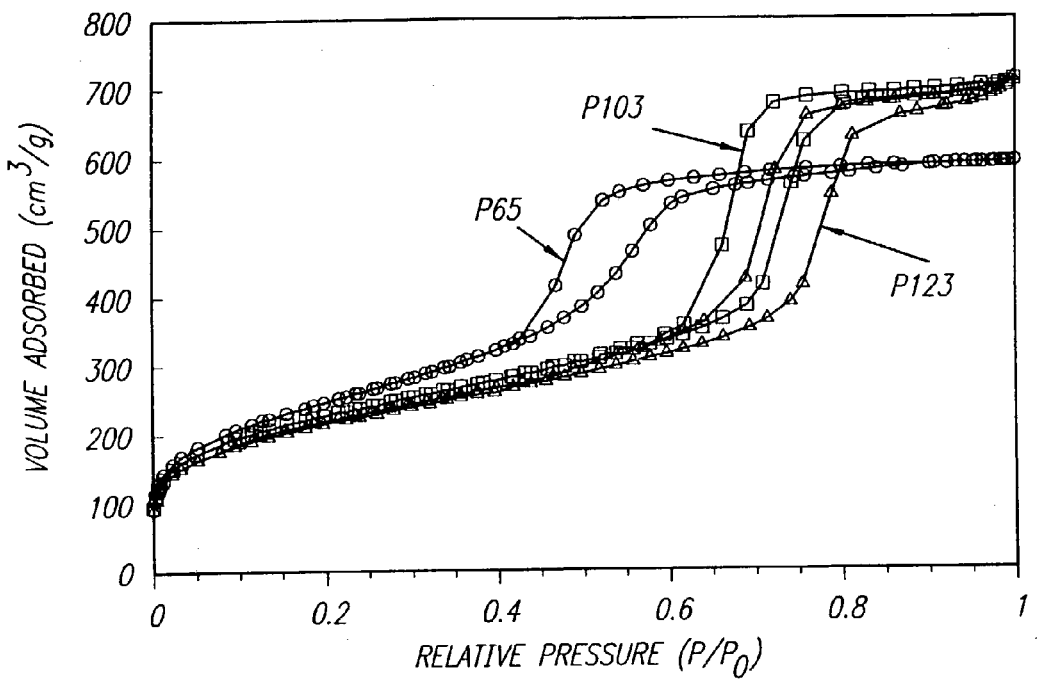
FIG. 48 shows nitrogen adsorption-desorption isotherm plots (top) and pore size distribution curves (bottom) for calcined meso-macro silica membranes prepared in NaCl solution using different block copolymers.
Figure 48B:
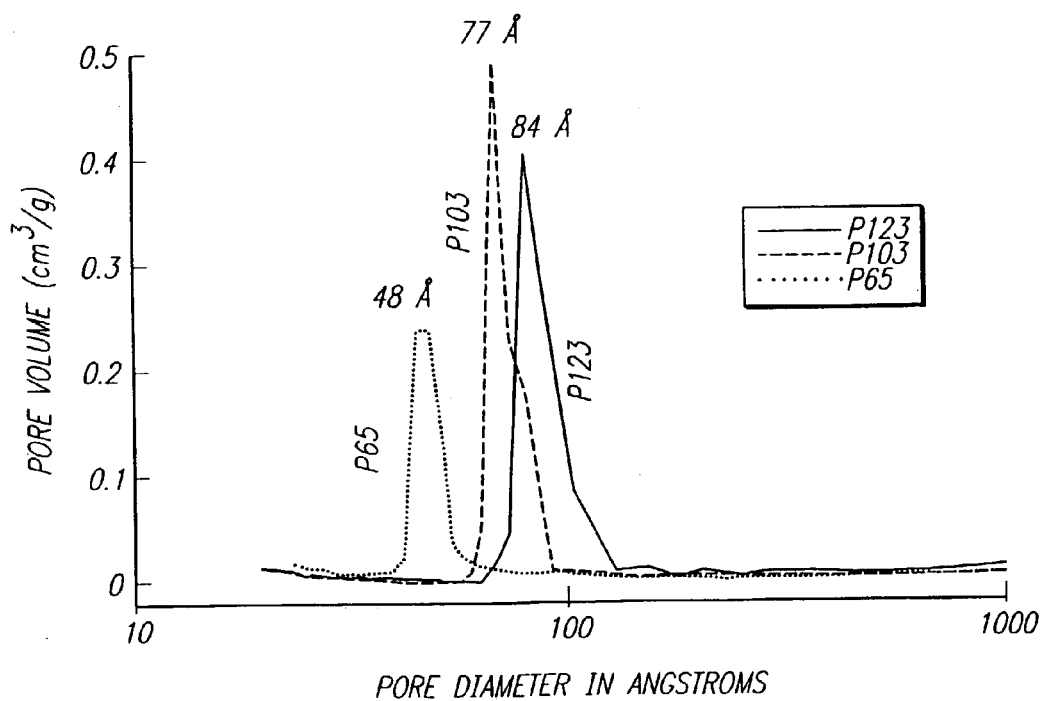
Figure 49A:
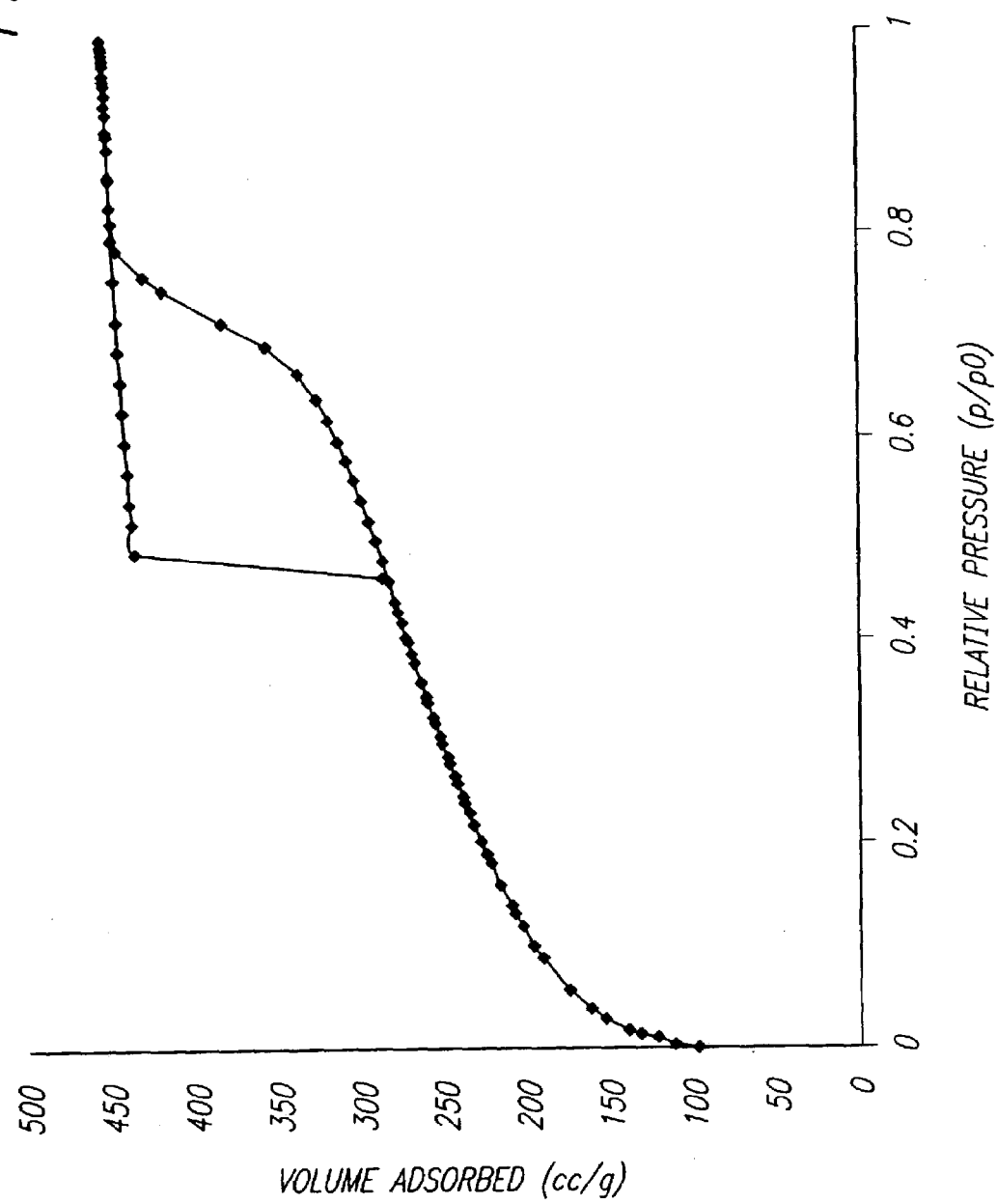
FIG. 49 shows nitrogen adsorption/desorption isotherm plots (a) and pore size distribution curves (b) for calcined meso-macro silica membranes prepared using block copolymer F127 in NaCl solution.
Figure 49B:
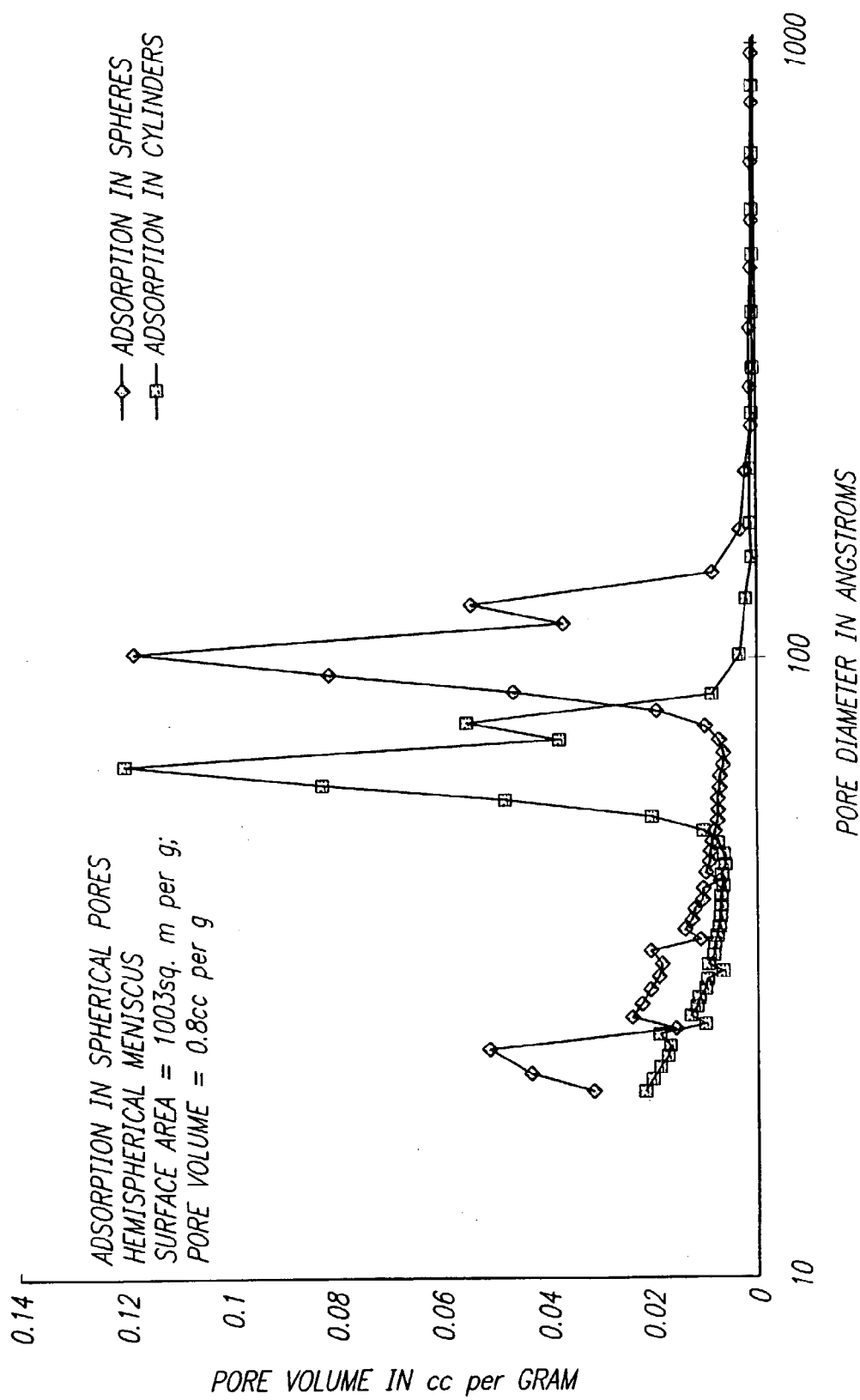
Figure 50A:
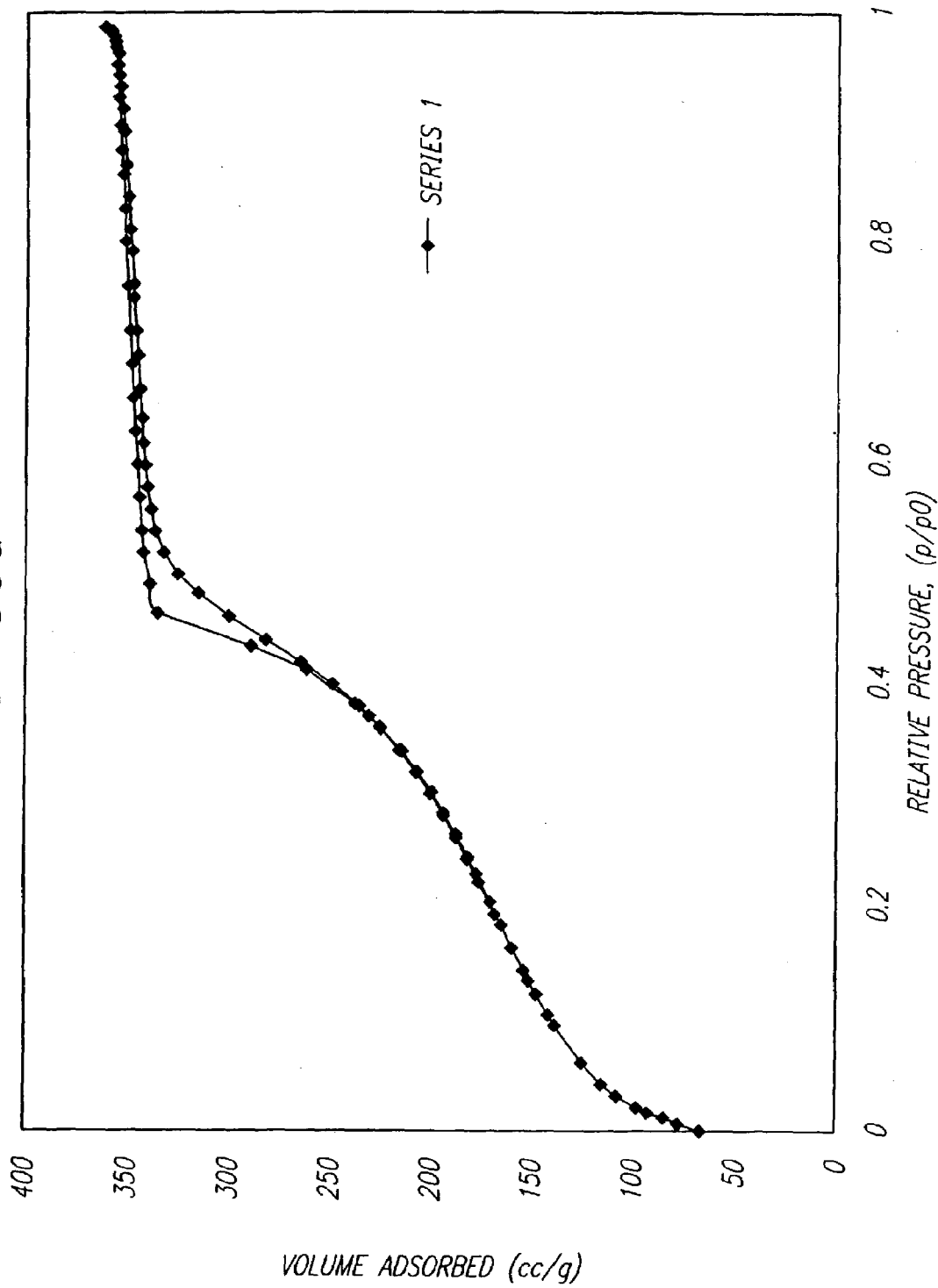
FIG. 50 shows nitrogen adsorption/desorption isotherm plots (a) and pore size distribution curves (b) for calcined meso-macro silica membranes prepared using non-ionic oligomeric surfactant Brij 76 ($C_{18}H_{17}EO_{10}OH$) in NaCl solution.
Figure 50B:
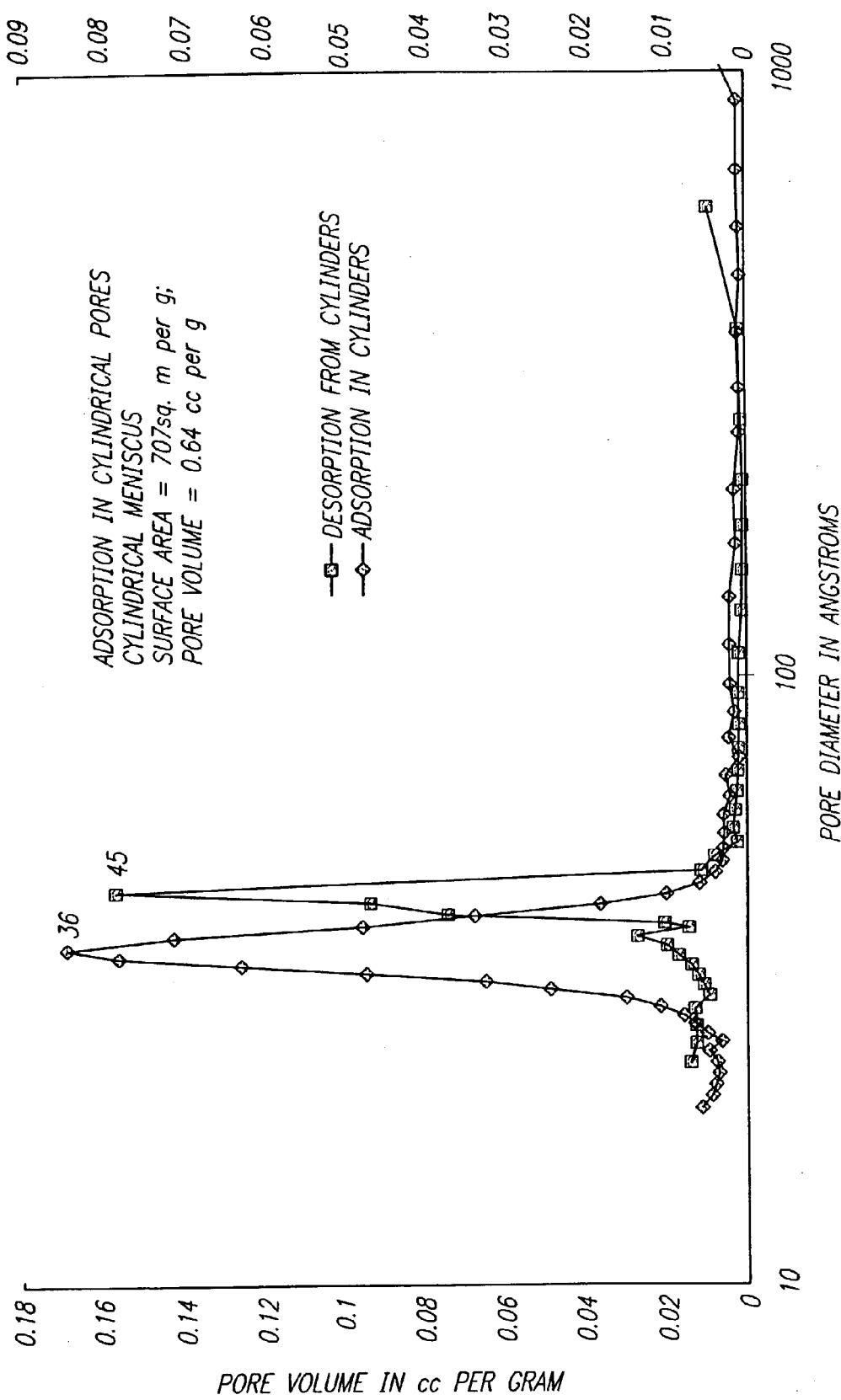

The representative nitrogen adsorption/desorption isotherms and the corresponding pore size distribution calculated by using Broekhoff and de Boer's model are shown in FIG. 48. The isotherms of FIG. 48. The isotherms were measured using a Micromeritics ASAP 2000 system. Data were calculated by using the BdB (Broekhoff and de Boer) model. The pore size distribution curve was obtained from an analysis of the adsorption branch of the isotherm. The pore volume was taken at $P/P_0$=0.985 signal point. The BET sample was pre-treated at 200° C. overnight on the vacuum line. The coral-like silica membranes prepared using P123 block copolymers in a NaCl solution show a typical isotherm (type IV) of cylindrical channel mesoporous materials with $H_1$-type hysteresis, and exhibit a narrow pore size distribution at the mean value of 84 Å. This material has a Brunauer-Emmett-Teller (BET) surface area of 660 $m^2/9$, and a pore volume of 1.1 $cm^3/g$. The mesoscopic pore size of the silica membranes prepared in NaCl solution depended on the amphiphilic block copolymer, for example, the materials prepared by using P103 and P65 show similar isotherms and exhibit pore sizes of 77 and 48 Å, BET surface areas of 720 and 930 $m^2/g$, and pore volumes of 1.12 and 0.99 $cm^3/g$ respectively (FIG. 48). When large molecular weight F127 block copolymer is used as the templates, the silica membrane with cubic mesoscopic structure shows the isotherms with a large $H_2$-type hysteresis (FIG. 49a) much different with that for hexagonal mesoscopic array silica membranes and does not fits to cylinders model by using BdB model to calculate the pore size distribution. (FIG. 49b) However, using spheres model, it shows quite narrow pore size distribution at a mean of 10.5 nm, and exhibit a BET surface area of 1003 $m^2/g$, pore volume of 0.8 $cm^3/g$ (FIG. 49b). The silica membranes prepared by using nonionic oligomeric surfactant $C_{16}H_{33}EO_{10}$ also high BET surface area of 710 $m^2/g$ and pore volume of 0.64 $cm^3/g$, but slight smaller a mean pore size of 3.6 nm (FIGS. 50a,b).

Figure 51A:
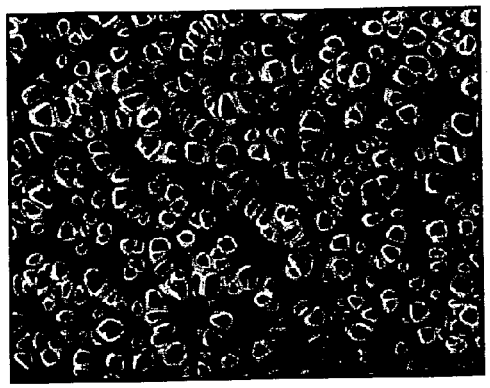
FIG. 51 shows SEM images of (a)–(d), as-synthesized silica membranes prepared by using P123 block copolymer in LiCl solution without washing recorded at different region, (a), top region; (b) middle region; (c), same (b) with large magnification; (d), bottom region of the membrane. (e)–(h) as-synthesized silica membranes prepared by using P123 block copolymer in $NiSO_4$ solution without washing recorded at different region, (a), top region; (b) same (a) with large magnification; (c) bottom region of the membrane; (d), disk-like $NiSO_4$ crystal.
Figure 51B:
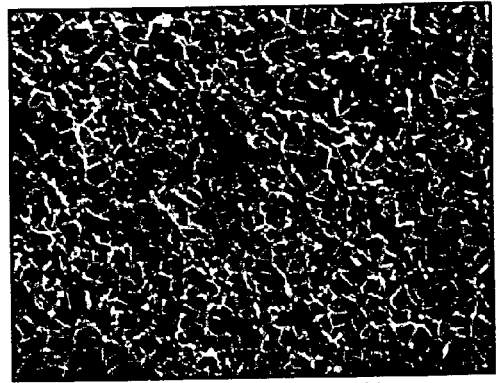
Figure 51C:
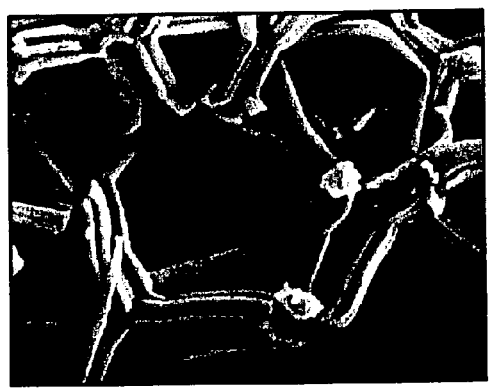
Figure 51D:
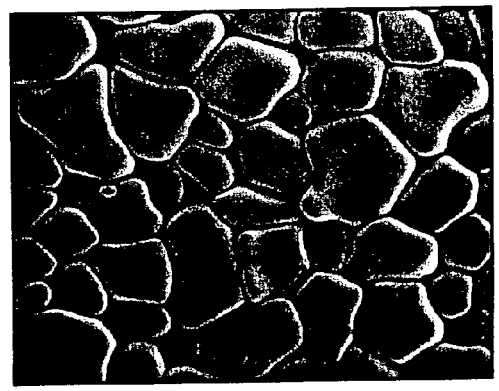
Figure 51E:
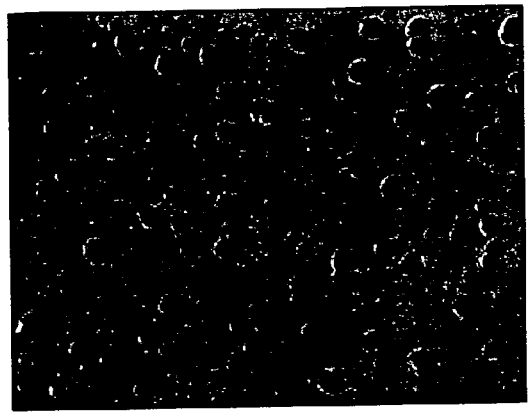
Figure 51F:
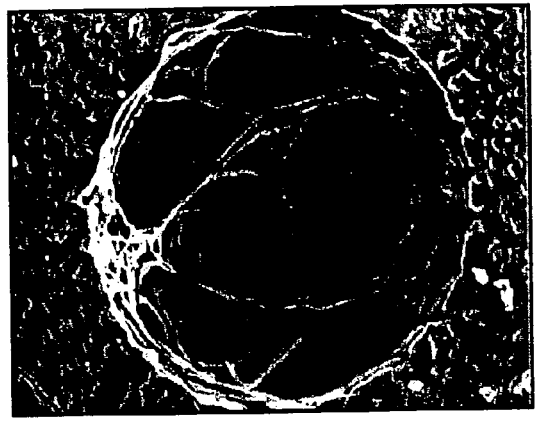
Figure 51G:
Figure 51H:
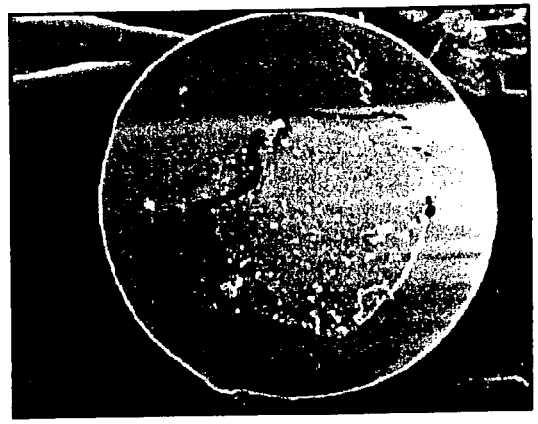

In order to understand the formation of the coral-like meso-macro silica membranes, we have carefully investigated the macroscopic structures in different areas (FIG. 51) of the as-made silica membranes prior to washing. As shown in FIGS. 51a–d, without washing out the inorganic salt (LiCl) the macroscopic coral-like structures of the membrane have been already formed in the middle region of the silica membrane. On the other hand, the image recorded in the top region of the silica membrane is quite different than that from the middle region and show disordered pillow windows that have similar average macro-window size compared that in the middle region. These results suggest that the silica membrane grown at the air interface is different than that water interface. FIG. 51d shows the SEM image of the silica membrane prepared by LiCl recorded at the bottom region, suggesting that the mosaic-like inorganic salt LiCl crystals, which are confined by XRD and chemical analysis, are formed in the bottom of the silica membranes. The shape of the pillow-like LiCl crystals is somewhat similar to the fenestrated morphology observed at the top region of the silica membrane. SEM images of the silica membrane prepared by using NiS04 as the inorganic salt recorded on the top, middle, bottom regions of the membrane are shown in FIGS. 51e–h. Without washing out the inorganic salt ($NiSO_4$) (FIGS. 51e,f) SEM images reveal a disk-like window morphology at the top of the membrane, while inside this window, a coral-like morphology can be seen (FIG. 46f). However, at the bottom of the membrane, grape vine-like silica macrostructures with disk-like inorganic salt $NiSO_4$ crystals are observed (FIG. 51g, h). The size of disk-like $NiSO_4$ crystals is the same as the window size of the silica membrane at the top. These results are consist with initial phase separation between the coral-like silica macrostructure and inorganic salts, followed by formation of the silica macrostructure above the inorganic salts.

Figure 52:
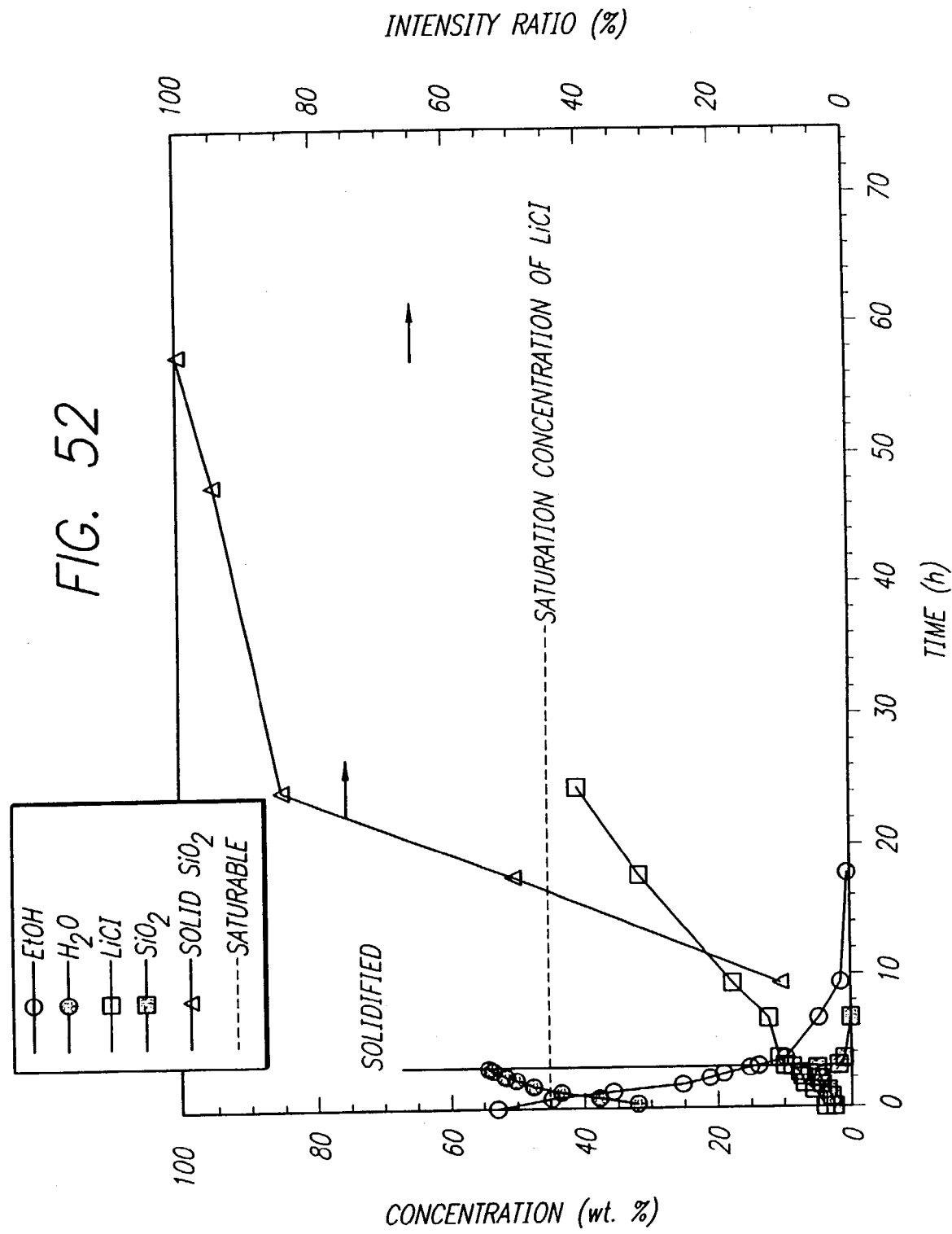
FIG. 52 shows the change of the compositions of the reaction mixture functioned with evaporation time. Change of the concentration in liquid phase of ethanol (open circle); water (solid circle); LiCl (open square); $SiO_2$ (solid square); Intensity ratio for (100) diffraction of silica-block copolymer mesophase (open triangle) and for (110) diffraction of LiCl crystal (solid triangle) at d spacing of 3.59 Å determined by XRD in solid phase.

In order to further confirm the formation of the materials, we investigate the change of composition as a function of the evaporation time (FIG. 52). The chemical composition of the starting reaction mixture was 1 g P123 block copolymer 0.0 1 mol TEOS: 1 g LiCl: $4\times10^{-5}$ mol HCl: 0.55 mol $H_2O$: 0.33 mol ETOH. As shown in FIG. 52, in the beginning, the concentration (weight %) of ethanol is decreased rapidly, and the concentration of water and $SiO_2$ and inorganic salt LiCl are increased since a large amount of ethanol is evaporated. After about 3 h, silica-block copolymer gel starts to form, in liquid phase, the concentration of silica is rapidly decreased and the concentration of LiCl is rapidly increased. When the silica mesostructure is formed as determined by XRD, almost all the ethanol has evaporated (in liquid phase, a concentration lower than 1%) and only a trace amount of silica is found in the liquid phase, suggesting that the silica/organic block copolymer composition has been already solidified at this time at the interface with salt water. When the concentration of salt LiCl is near saturation concentration (45%), the crystallization of the inorganic salt LiCl occurs. At this time, the formation of mesostructured silica has been almost completed. These results further indicate that the macroscopic silica structure is formed first at the interface of inorganic salt water, and sequentially, when the solution of the inorganic salt reaches saturation concentrations, crystal of inorganic salts are formed in the bottom of the membrane.

Figure 53:
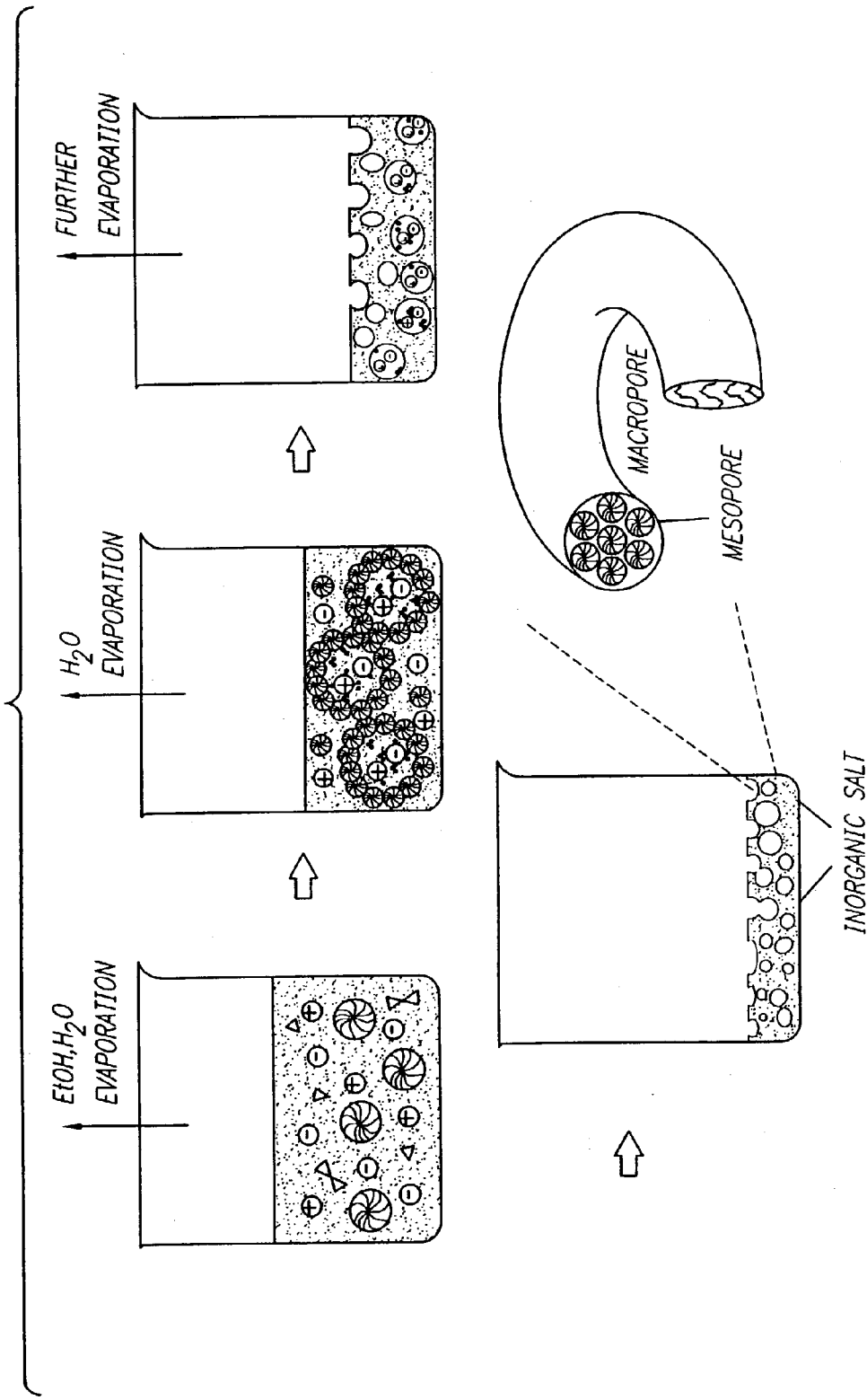
FIG. 53 shows a schematic diagram of the simple procedure used to prepare coral-like mesomacro silica membranes.

Based on above results, we postulate that macroscopic silica structure is formed around a droplet of inorganic salt solution as illustrated in Scheme A (FIG. 53). Ethanol is first evaporated, then, water. As the inorganic salt solution becomes more concentrated, two domains are formed, one a water-rich domain, where most inorganic salt is located, another a water-poor domain, where silica and block copolymer compositions are located. The formation of two domains results in tri-phase separation, a droplet of inorganic salt solution phase separated by silica-block copolymer gel. The droplet of the solution serves as a template for the growth of silica-block copolymer composites. Once the macrostructure is rigidified, the inorganic salt solution approaches to the bottom of the container progressively. The cooperative self-assembly of silica/block copolymer occurs at the interface of the droplet, and results in coral-like mesomacroscopic silica structure. On the other hand, when the silica is formed at the interface of air and salt water, the droplet of the salt solution becomes flatters, resulting in the fenestrated membrane at the top.

Figure 54A:
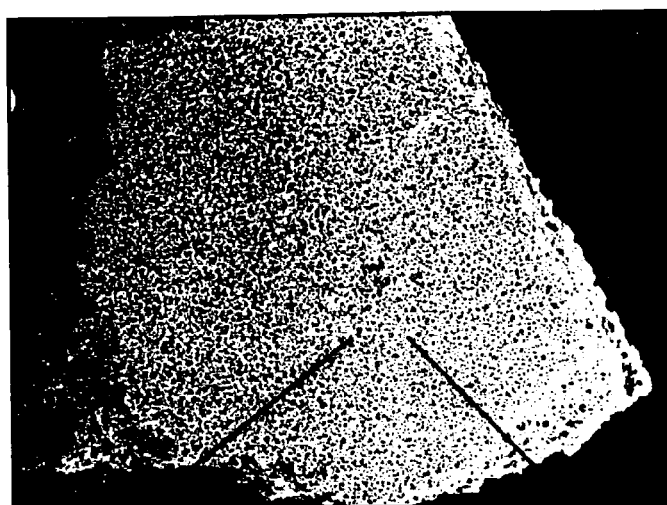
FIG. 54 shows progressively higher magnifications of a section of a meso-macro silica membrane made in accordance with this invention.
Figure 54B:
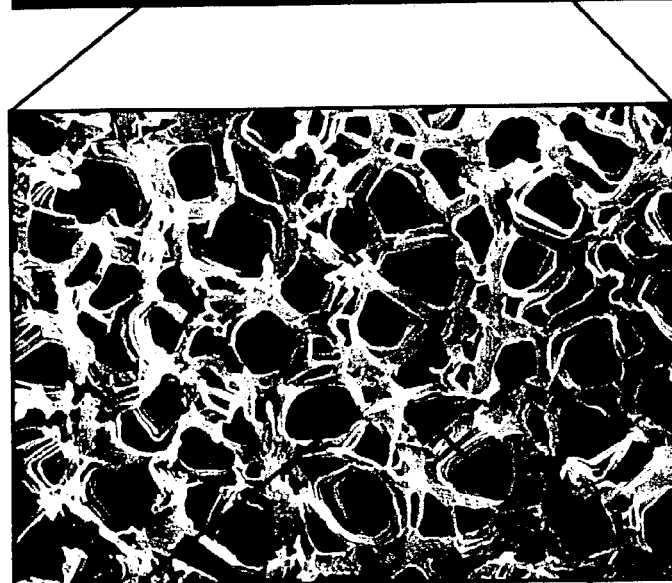
Figure 54C:
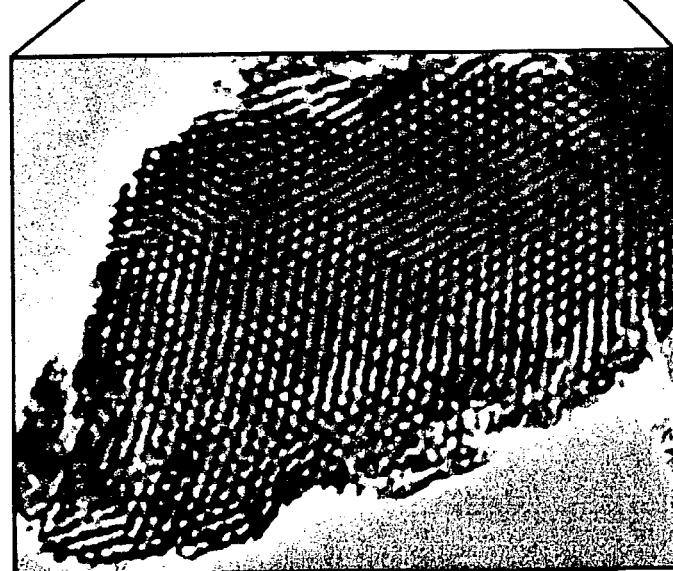

Referring to FIG. 54, progressively higher magnifications are shown of a section of a meso-macro silica membrane made in accordance with this invention. The membrane is shown in FIG. 54a which has a macropore structure, as shown in FIG. 54b. However the walls defining the macropores have a mesoporous structure.

In summary, artificial coral silica membranes with 3-d meso-macro structures have been synthesized by a novel process of an acidic catalyzed silica sol-gel chemistry in the present of inorganic salts. Inorganic salts play an important role on the formation of meso-macro silica membranes that are grown at the interface of a droplet of inorganic salt solution. The results are of general important for understanding multiphase processes such as the formation of diatoms coral silica structures in nature. The silica membranes (size—4 cm×4 cm, thickness—5 mm) with 3-d meso-macro silica network structures show oriented continuous rope, toroid, and grape vine, or dish, pinwheel, gyroid, and cubic cage morphologies depending on the electrolyte strength of the inorganic salts or amphiphilic block copolymer templates. The macropore size (0.5~100 μm) can be controlled by inorganic salts and the evaporation rate of the solvent. The mesoscopic structures can be highly ordered 2-d honeycomb (pore size 40–90 Å) or 3-d cubic packing and are controlled by the amphiphilic block copolymer templates. The coral-like mesomacro silica membranes are thermally stable and exhibit large surface areas (to 1000 cm$^2$/g) and pore volume (to 1.1 cm$^3$/g). We anticipate that these new process ceramics material with structure and design on multiple length scales will have many applications in the areas, including separation, sorption, medical implant, catalysis, and sensor array applications.

The example shown above in forming meso-macro silica membranes used PLURONIC P123 block copolymer, $EO_{20}PO_{70}EO_{20}$ as the template to control mesoscopic ordering of the silica membranes. Besides P123, other surfactants can also be used in the synthesis. For example, one could use:

(1) a diblock copolymer, poly(ethylene oxide)-block-poly(propylene oxide); poly(ethylene oxide)-block-poly(butylene oxide) (Dow Company); B50-6600, BL50-1500;

(2), a triblock copolymer, poly(ethylene oxide)-block-poly(propylene oxide)-block poly(ethylene oxide); (BASF) poly(ethylene oxide)-block-poly(butylene oxide)-block poly(ethylene oxide) (Dow Company); such as PLURONIC L64, L121, L122, P65, P85, P103, P104, P123, PF20, PF40, PF80, F68, F88, F98, F108, F127;

(3) a reversed triblock copolymer PLURONIC 25R8, 25R4, 25R2

(4) a star di-block copolymer (BASF), TETRONIC 901, 904, 908; and (5) a reversed star di-block copolymer TETRONIC 90R1, 90R4, 90R8.

The inorganic salts can be electrolyte, such as KCl, NaCl, LiCl, $NH_4Cl$, $MgCl$, $MgSO_4$, $KNO_3$, $NaClO_3$, $Na_2SO_4$, $NiSO_4$, $CoCl_2$, water organic acid, such as DL tartaric acid, citric acid, malic acid. We claim that dissolvable alkali salts, alkaline earth salts, transition metal, sulfate, nitrate, halide, chlorate, per chlorate.

The preparation of meso-macro silica membrane are emulsion chemistry latex sphere template; phase separation and solvent exchanged; inorganic salts templating which was developed by ourselves here. This discovery should have great signification for understanding the formation of the diatom and coral in nature, The macromesoporous materials would have many applications in the areas of sorption, catalysis, separation, sensor arrays, optoelectionic devices. The materials and synthesis method described here are very versatile in that they can be used for many fields of application and for synthesis of any inorganic-surfactant composites, for example, aluminophosphate-based, $TiO_2$, $ZrO_2$, $Al_2O_3$, $Nb_2O_5$, $Ta_2O_5$, $Cr_2O_3$, $Fe_2O_3$, $ZrTiO_4$, $Al_2SiO_5$, $HfO_2$, meso-macroporous silica membranes. These materials would have many applications on sorption, catalysis, separation, sensor arrays, optoelectionic devices.

TABLE 1

Physicochemical Properties of Mesoporous Silica (SBA) prepared using Polyoxyalkylene Block Copolymers.

| Block Copolymer | Formal | Mesophase | d(Å)[a] | BET surface area (m$^2$/g) | pore size[b] (Å) | pore volume(m$^3$/g) | Wall[c] thickness (Å) |
|---|---|---|---|---|---|---|---|
| Pluronic L121 | PEO$_5$PPO$_{70}$PEO$_5$ | lamellar | 116 | | | | |
| Pluronic L121 | PEO$_5$PPO$_{70}$PEO$_5$ | hexagonal | 118(117) | 633 | 100 | 1.04 | 35 |
| Pluronic F127 | PEO$_{106}$PPO$_{70}$PEO$_{106}$ | cubic | 124(118 | 742 | 54 | 0.454 | |
| Pluronic F88 | PEO$_{100}$PPO$_{39}$PEO$_{100}$ | cubic | 118(101) | 696 | 35 | 0.363 | |
| Pluronic F68 | PEO$_{80}$PPO$_{30}$PEO$_{80}$ | cubic | 91.6(88.9) | | | | |
| Pluronic P123 | PEO$_{20}$PPO$_{70}$PEO$_{20}$ | hexagonal | 104(95.7) | 692 | 47 | 0.557 | 64 |
| Pluronic P123 | PEO$_{20}$PPO$_{70}$PEO$_{20}$ | hexagonal | 105(97.5)*[d] | 780 | 60 | 0.795 | 53 |
| Pluronic P123 | PEO$_{20}$PPO$_{70}$PEO$_{20}$ | hexagonal | 103(99.5)*[e] | 820 | 77 | 1.03 | 38 |
| Pluronic P123 | PEO$_{20}$PPO$_{70}$PEO$_{20}$ | hexagonal | 108(105)*[f] | 920 | 85 | 1.23 | 36 |
| Pluronic P123 | PEO$_{20}$PPO$_{70}$PEO$_{20}$ | hexagonal | 105(104)*[g] | 850 | 89 | 1.17 | 31 |
| Pluronic P103 | PEO$_{17}$PPO$_{85}$PEO$_{17}$ | hexagonal | 97.5(80.6) | 768 | 46 | 0.698 | 47 |
| Pluronic P65 | PEO$_{20}$PPO$_{30}$PEO$_{20}$ | hexagonal | 77.6(77.6) | 1003 | 51 | 1.26 | 39 |

TABLE 1-continued

Physicochemical Properties of Mesoporous Silica (SBA) prepared using Polyoxyalkylene Block Copolymers.

| Block Copolymer | Formal | Mesophase | d(Å)[a] | BET surface area (m$^2$/g) | pore size[b] (Å) | pore volume(m$^3$/g) | Wall[c] thickness (Å) |
|---|---|---|---|---|---|---|---|
| Pluronic P85 | PEO$_{26}$PPO$_{39}$PEO$_{26}$ | hexagonal | 92.6(88.2) | 962 | 60 | 1.08 | 42 |
| Pluronic L64 | PEO$_{13}$PPO$_{70}$PEO$_{13}$ | hexagonal | 80.6(80.5) | 950 | 59 | 1.19 | 34 |
| Pluronic 25R4 | PEO$_{19}$PPO$_{33}$PEO$_{19}$ | hexagonal | 74.5(71.1) | 1040 | 48 | 1.15 | 34 |
| Tetronic 908 | | cubic | 101(93.6) | 1054 | 30 | 0.692 | |
| Tetronic 901 | | cubic | 73.9(70.1) | | | | |
| Tetronic 90R4 | | cubic | 7.39(68.5) | 1020 | 45 | 0.910 | — |

[a] d(100) spacing or d value of characteristic reflection of the as-synthesized products and the value inside brackets is the d value after calcination at 500° C. for 6 h;
[b] calculated from adsorption branch;
[c] calculated by a$_o$-pore size (a$_o$ = 2 × d(100)/√3).
*reaction at 35° C. for 20 h, then heating: (d) at 80° C. for 24 h; (e) at 80° C. for 48 h; (f) at 90° C. for 24 h; (g) at 100° C. for 24 h.

TABLE 2

Physicochemical Properties of Mesoporous Silica (SBA) Prepared Using Nonionic Alkyl Polyethylene Oxide Surfactants.

| Surfactant | Reaction Temperature | Mesophase | d(Å)[a] | BET surface area (m$^2$/g) | pore size[b] (Å) | pore volume (m$^3$/g) |
|---|---|---|---|---|---|---|
| C$_{14}$EO$_2$ | RT | lamellar | 64.3 | | | |
| C$_{12}$EO$_4$ | RT | cubic | 45.3(44.7) | 665 | 22 | 0.375 |
| C$_{12}$EO$_4$ | RT | lamellar (La) | 45.7 | 570 | | |
| C$_{12}$EO$_4$ | 60° C. | lamellar | 42.4 | 606 | 24 | 0.392 |
| C$_{16}$EO$_{10}$ | RT | cubic | 56.6(47.6) | 1070 | 25 | 0.678 |
| C$_{16}$EO$_{10}$ | 100° C. | hexagonal | 64.1(62.8) | 910 | 35 | 1.02 |
| C$_{16}$EO$_{20}$ | RT | cubic | 73.7(49.6) | 602 | 22 | 0.291 |
| C$_{18}$EO$_{10}$ | RT | P6$_3$/mmc | 63.5(51.0) | 1150 | 31 | 0.826 |
| C$_{18}$EO$_{10}$ | 100° C. | hexagonal | 77.4(77.0) | 912 | 40 | 0.923 |
| C$_{18}$H$_{35}$EO$_{10}$ | RT | P6$_3$/mmc | 49.1(47.7) | 1004 | 27 | 0.587 |
| C$_{12}$EO$_{23}$ | RT | cubic | 64.8(43.3) | 503 | 16 | 0.241 |
| Tween 20 | RT | cubic | 55.1(46.8) | 795 | 19 | 0.370 |
| Tween 40 | RT | cubic | 52.4(49.6) | 704 | 20 | 0.363 |
| Tween 60 | RT | cubic | 62.4(54.4) | 720 | 24 | 0.516 |
| Tween 60 | RT | lamellar | 28.7 | | | |
| Tween 80 | RT | cubic | 62.2(53.9) | 712 | 25 | 0.431 |
| Span 40 | RT | lamellar | 55.5 | | | |
| Triton X100 | RT | cubic | 41.8(35.5) | 776 | 17 | 0.353 |
| Triton X114 | RT | cubic | 42.2(36.7) | 989 | 16 | 0.453 |
| Teritor TMN 6 | RT | cubic | 44.3(39.9) | 1160 | 23 | 0.568 |
| Teritor TMN 10 | RT | cubic | 42.3(36.5) | 804 | 20 | 0.379 |

[a] d(100) spacing or d value of characteristic reflection of the as-synthesized products and the number inside brackets is the d value after calcination at 500° C. for 6 h.
[b] calculated from adsorption branch.

TABLE 3

| System | Inorganic Precursor | Aging Temperature, ° C. | Aging time (day) | d (Å) |
|---|---|---|---|---|
| Zr | ZrCl$_4$ | 40 | 1 | 125 |
| Ti | TiCl$_4$ | 40 | 7 | 123 |
| Al | AlCl$_3$ | 40 | 2 | 130 |
| Si | SiCl$_4$ | 40 | 2 | 171 |
| Sn | SnCl$_4$ | 40 | 2 | 124 |
| Nb | NbCl$_5$ | 40 | 2 | 106 |
| Ta | TaCl$_5$ | 40 | 2 | 110 |
| W | WCl$_8$ | 60 | 15 | 126 |
| Hf | HfCl$_4$ | 40 | 1 | 124 |
| Ge | GeCl$_4$ | 40 | 15 | 146 |
| V | VCl$_4$ | 60 | 7 | 111 |
| Zn | ZnCl$_2$ | 60 | 30 | 120 |
| Cd | CdCl$_2$ | 40 | 7 | 111 |
| In | InCl$_3$ | 60 | 30 | 124 |
| Sb | SbCl$_5$ | 60 | 30 | 93 |
| Mo | MoCl$_5$ | 60 | 7 | 100 |
| Re | ReCl$_5$ | 60 | 7 | 121 |
| Ru | RuCl$_3$ | 40 | 3 | 95 |
| Ni | NiCl$_2$ | 40 | 2 | 100 |
| Fe | FeCl$_3$ | 40 | 7 | 116 |
| Cr | CrCl$_3$ | 40 | 4 | 117 |
| Mn | MnCl$_2$ | 40 | 7 | 124 |
| Cu | CuCl$_2$ | 40 | 7 | 98 |
| SiAl | AlCl$_3$/SiCl$_4$ | 40 | 2 | 120 |
| Si$_2$Al | AlCl$_3$/SiCl$_4$ | 40 | 2 | 120 |
| ZrTi | ZrCl$_4$/TiCl$_4$ | 40 | 2 | 110 |
| Al$_2$Ti | AlCl$_3$/TiCl$_4$ | 40 | 7 | 112 |
| SiTi | SiCl$_4$/TiCl$_4$ | 40 | 3 | 103 |
| ZrW$_2$ | ZrCl$_4$/WCl$_6$ | 40 | 3 | 140 |
| SnIn | SnCl$_4$/InCl$_3$ | 40 | 30 | 83 |

TABLE 4

| Oxide | $d_{100}$ (Å) | Wall Structure | Wall Thickness (Å) | Nanocrystal Size (Å) | Pore Size (Å) | BET Surface Area (m²/g) | Porosity | Physical Properties |
|---|---|---|---|---|---|---|---|---|
| $ZrO_2$ | 106 | Tetra.$ZrO_2$ | 65 | 15 | 58 | 150 | 0.43 | dielectric |
| $TiO_2$ | 101 | Anatase | 51 | 24 | 65 | 205 | 0.46 | semicond. |
| $Nb_2O_5$ | 75 | $Nb_2O_5$ | 40 | <10 | 45 | 196 | 0.50 | dielectric |
| $Ta_2O_5$ | 68 | $Ta_2O_5$ | 40 | <10 | 35 | 165 | 0.50 | dielectric |
| $WO_3$ | 95 | $WO_3$ | 50 | 30 | 50 | 125 | 0.48 | semicond. |
| $SnO_2$ | 106 | Cassiterite | 50 | 30 | 68 | 180 | 0.52 | semicond. |
| $HfO_2$ | 105 | amorphous | 50 | — | 70 | 105 | 0.52 | dielectric |
| $Al_2O_3$ | 186 | amorphous | 35 | — | 140 | 300 | 0.61 | dielectric |
| $SiO_2$ | 198 | amorphous | 86 | — | 120 | 810 | 0.63 | dielectric |
| $SiAlO_{3.5}$ | 95 | amorphous | 38 | — | 60 | 310 | 0.59 | dielectric |
| $Si_2AlO_{5.5}$ | 124 | amorphous | 40 | — | 100 | 330 | 0.55 | dielectric |
| $Al_2TiO_5$ | 105 | amorphous | 40 | — | 80 | 270 | 0.59 | dielectric |
| $ZrTiO_4$ | 103 | amorphous | 35 | — | 80 | 130 | 0.46 | dielectric |
| $SiTiO_4$ | 95 | amorphous | 45 | — | 80 | 495 | 0.63 | dielectric |
| $ZrW_2O_8$ | 100 | amorphous | 45 | — | 50 | 170 | 0.51 | NTE |

The invention claimed is:

1. A method of forming a mesoscopically structured material comprising the step of combining an amphiphilic block copolymer with an inorganic species in a solvent, wherein the block copolymer and the inorganic species are assembled and then the assembled inorganic species are polymerized to form a mesoscopically structured inorganic-organic composite.

2. The method of claim 1, wherein said inorganic species is tetraethoxysilane which has a molecular formula of $Si(OC_2H_5)_4$.

3. A mesoscopically structured material that was formed by combining an amphiphilic block copolymer with an inorganic species in a solvent, wherein the block copolymer and the inorganic species are assembled and then the assembled inorganic species are polymerized to form a mesoscopically structured inorganic-organic composite.

4. The mesoscopically structured material of claim 3, wherein said inorganic species is tetraethoxysilane which has a molecular formula of $Si(OC_2H_5)_4$.

* * * * *